United States Patent [19]

Nakao et al.

[11] Patent Number: 5,691,330
[45] Date of Patent: Nov. 25, 1997

[54] CONDENSED THIOPHENE COMPOUND AND PHARMACEUTICAL USE THEREOF

[75] Inventors: Tohru Nakao; Yuji Ono; Masahiro Bougauchi, all of Fukuoka; Yasuto Morimoto, Osaka, all of Japan

[73] Assignee: Yoshitomi Pharmaceutical Industries, Ltd., Osaka, Japan

[21] Appl. No.: 478,843

[22] Filed: Jun. 7, 1995

Related U.S. Application Data

[60] Division of Ser. No. 272,320, Jul. 8, 1994, Pat. No. 5,532,240, which is a continuation-in-part of Ser. No. 107,564, filed as PCT/JP92/01695 Dec. 24, 1992, abandoned.

[30] Foreign Application Priority Data

Dec. 26, 1991 [JP] Japan .............................. HEI3-359547
Oct. 23, 1992 [JP] Japan .............................. HEI4-309388

[51] Int. Cl.$^6$ .................. A61K 31/55; C07D 487/04; C07D 473/18
[52] U.S. Cl. ............................ 514/215; 540/523
[58] Field of Search ........................ 514/215; 540/523

[56] References Cited

U.S. PATENT DOCUMENTS

| | | | |
|---|---|---|---|
| 4,352,811 | 10/1982 | Strupczewski et al. | 424/267 |
| 4,414,225 | 11/1983 | Sauter et al. | 424/274 |
| 4,458,076 | 7/1984 | Strupczewski | 546/199 |
| 4,482,559 | 11/1984 | Schneider et al. | 424/256 |
| 4,524,206 | 6/1985 | New et al. | 544/230 |
| 4,735,940 | 4/1988 | Fischer et al. | 514/212 |
| 4,812,461 | 3/1989 | Antoku et al. | 514/278 |
| 4,937,249 | 6/1990 | Antoku et al. | 514/321 |
| 5,173,490 | 12/1992 | Peglion et al. | 514/254 |
| 5,532,240 | 7/1996 | Nakao et al. | 514/254 |

FOREIGN PATENT DOCUMENTS

| | | |
|---|---|---|
| A 58341 | 8/1982 | European Pat. Off. . |
| A 150034 | 7/1985 | European Pat. Off. . |
| A0465254 | 1/1992 | European Pat. Off. . |
| B46-39350 | 11/1971 | Japan . |
| A48-57994 | 8/1973 | Japan . |

OTHER PUBLICATIONS

Chemical Abstracts, vol. 55, col. 23488 (1961).
Chemical Abstracts, vol. 59, col. 3862 (1963).
Chemical Abstracts, vol. 64, col. 586 (1966).
Chemical Abstracts, vol. 69, 18565x (1968).
J. Heterocyclic Chem., vol. 13, pp. 1347–1349 (1976) (with English Summary).

*Primary Examiner*—Mukund J. Shah
*Assistant Examiner*—Pavanaram K. Sripada
*Attorney, Agent, or Firm*—Sughrue, Mion, Zinn, Macpeak & Seas, PLLC

[57] ABSTRACT

A condensed thiophene compound represented by general formula:

$$
\begin{array}{c}
R^2 \quad A-(CH_2)_m \\
\diagdown \quad \diagup \\
N \\
| \\
B \\
\diagdown \\
(CH_2)_n - D
\end{array}
\quad\quad
\begin{array}{c}
R^1 \\
S \\
G-Q-T
\end{array}
\quad\quad (I)
$$

or a pharmaceutically acceptable salt thereof, wherein ring S represents a thiophene ring; $R^1$ represents hydrogen, halogen, alkyl, etc.; $R^2$ represents hydrogen, alkyl, acyl, etc.; G represents —$CH_2$—, —CH(OH)—, —CO—, etc.; Q represents alkylene; T represents —N(Rb)(Rc) (wherein Rb, Rc represents each alkyl etc.; or alternatively Rb and Rc are combined together to form cyclic amino); D represents —$CH_2$— or —S—; A and B represent each carbonyl or thiocarbonyl, or are null; and m and n represent each 0, 1 to 4, provided that m+n represents an integer of 4 or less.

This compound is useful as an antipsychotic drug having a reduced extrapyramidal side effect.

7 Claims, No Drawings

CONDENSED THIOPHENE COMPOUND AND PHARMACEUTICAL USE THEREOF

This is a divisional of application Ser. No. 08/272,320 filed Jul. 8, 1994 now U.S. Pat. No. 5,532,240, which is a continuation-in-part of prior application Ser. No. 08/107,564 filed Aug. 18, 1993 (abandoned), which is a continuation-in-part of PCT/JP92/0695 filed Dec. 24, 1992.

FIELD OF THE INVENTION

The present invention relates to novel and pharmaceutically useful condensed thiophene compounds or salts thereof and pharmaceutical uses thereof, and further synthetic intermediates for said condensed thiophene compounds.

BACKGROUND OF THE INVENTION

The following compounds and the method of preparation thereof are disclosed in (1) Chemical Abstracts, vol. 55, column 23488 (1961), (2) Nippon Kagaku Zassi, vol: 83-3, pp. 343–347 (1962), [Chemical Abstracts, vol. 59, column 3862 (1963)], (3) Chemical Abstracts, vol. 64, column 586 (1966), (4) Chemical Abstracts, vol. 69, 18565x (1968), (5) U.S. Pat. No. 4,735,940, column 39, lines 50–51 and (6) Journal of Heterocyclic Chemistry, vol. 13, pp. 1347–1349 (1976).

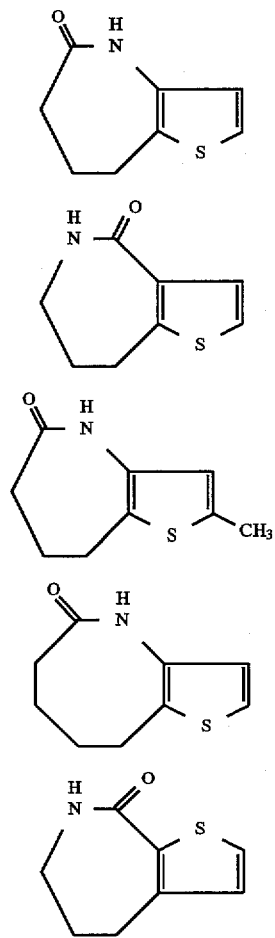

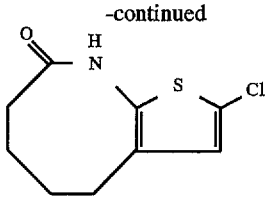

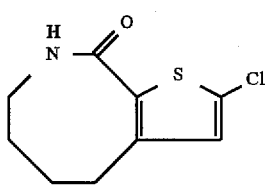

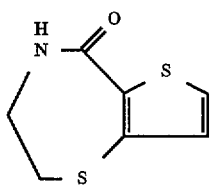

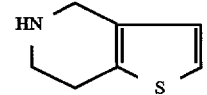

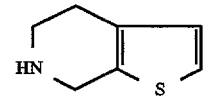

On the other hand, compounds having antipsychotic activity are known by patent publications such as JP-A S60-84282, JP-A S59-227882, JP-A S58-90583, JP-A S63-132887, JP-A S63-183576, JP-A H1-199967 and JP-A H4-308584.

Antipsychotic drugs introduced in 1950's have been played a large role in treating schizophrenia.

In 1960's "dopamine hypothesis" concerned with schizophrenia has been suggested (Carlsson, A. et al, Acta. Pharmacol. Toxicol. 20, 140–144 (1963)) and the strong correlation between the affinity of antipsychotic drugs for $D_2$ receptors in striatum and the average clinical dose hive been reported (Seeman, P. et al, Nature, 261,717–719 (1976), Creese, I. et al, Science, 192,481–483 (1976)). After that, the concept of the development of anti psychotic drugs was the blockade of $D_2$ receptors. However, typical antipsychotic drugs are effective for the treatment of the positive symptoms such as hallucination and delusions, but not effective for that of the negative symptoms such as apathy and social withdrawal (Zubin, J. et al, Comprehensive Psychiatry, 26, 217–240 (1985)). And the extrapyramidal side-effect (EPS: dystonia, akathidia, tardive dyskinesia) and the elevation in the level of serum prolactin in the acute and chronic treatment of typical antipsychotic drugs are the serious problems for patients.

From these points of view, the development of atypical antipsychotic drugs, produce fewer EPS and are more effective than typical antipsychotic drugs in treating schizophrenia, is desired.

The profile of atypical antipsychotic drug are as follows.
1) It is effective for both positive and negative symptoms.
2) It produces fewer EPS.
3) It has no side-effect of internal secretion.

1. Merits by addition of 5-HT$_2$ receptor antagonistic activity:

In clinical study, it has been reported that the selective 5-HT$_2$ antagonist ritanserin ameliorates negative symptoms and reduces the incidence of EPS caused by typical antipsychotic drug therapy (Bersani, G. et al, Curr. Ther. Res., 10, 492–499 (1986)). And in preclinical study, it has also been reported that 5-HT$_2$ antagonists reduced catalepsy induced by haloperidol (Hicks, P. B., Life Sci., 47, 1609–1615 (1990)). On the other hand, syndrome malin induced by neuroleptics is the unbalance of dopaminergic and serotonergic activity in the center of the regulation of temperature has been proposed (Yamawaki, N., Sinkeiseisinyakuri, 11, 17–24 (1989). Therefore, it is expected that additional 5-HT$_2$ receptor antagonism reduces the syndrome malin.

Risperidone has extremely potent 5-HT$_2$ and potent D$_2$ receptor antagonistic properties (Janssen, P. A. J. et al, J. Pharmacol. Exp. Ther. 244, 685–693 (1988)), and has revealed a clinical profile that is distinct from that of existing neuroleptics. Risperidone proved to be an effective antipsychotic, with low EPS liability and with beneficial effects on the negative symptoms of schizophrenia (The 1st International Risperidone Investigator's Meeting (Conference Review), Paris (France), Mar. 9–10, 1992), but it has not a character of atypical antipsychotic drug yet because EPS is appeared in high dose of risperidone and it has side-effect of internal secretion yet.

2. Merits by addition of 5-HT$_{1A}$ agonist:

5-HT$_{1A}$ agonist has been reported to be possible to make up for the disadvantage of typical antipsychotic drugs, because 5-HT$_{1A}$ agonist buspirone improved the depression and EPS caused by haloperidol therapy in clinical study (McMillen, B. A. et al, J. Pharma. Pharmacol., 40, 885–887 (1988)). And, it is supported to the above mentioned possibility that 5-HT$_{1A}$ agonist 8-OH DPAT and buspirone reverse catalepsy induced by haloperidol in preclinical study (Golf, D. C. et al, J. Clin. Psychopharmacol. 11, 193–197 (1991)), Invernizzi, R. W. et al, Neuropharmacology, 27, 515–518 (1988)). And then, amplification of antipsychotic effect by additional 5-HT$_{1A}$ agonistic activity is expected, because administration of 8-OH DPAT with D$_2$ antagonist inhibit conditioned avoidance response (CAR) more potent than that of D$_2$ antagonist only (Wadenberg, M. L. et al, J. Neural. Transm. 83, 43–53 (1991)).

3. The functional relationships of 5-HT$_{1A}$ receptors and 5-HT$_2$ receptors:

By the study of electrical physiology and biochemistry, it has been revealed that 5-HT$_{1A}$ and 5-HT$_2$ receptors regulate the serotonergic activity through the K channel (second messenger system in cell) (Bobker, H. H. et al, Trends Neurosci., 13, 169–173 (1990)). Stimulation of 5-HT$_{1A}$ receptor makes a hyperpolarization, and stimulation of 5-HT$_2$ receptor makes a depolarization. Therefore, both 5-HT$_{1A}$ agonist and 5-HT$_2$ antagonist inhibit the serotonergic activity, and the inhibition of serotonergic activity is amplified if 5-HT$_{1A}$ agonistic and 5-HT$_2$ antagonistic activities are occurred at the same time. This is supported by the preclinical pharmacological data that anxiolitic and antidepressant effects of 5-HT$_{1A}$ agonist are reinforced by addition of 5-HT$_2$ antagonist (Millan, M. J. et al, J. Neural. Transm. 83, 43–53 (1991)).

As mentioned above, it has been reported that the disadvantages of typical antipsychotic drugs are improved by addition of 5-HT$_2$ antagonistic and 5-HT$_{1A}$ agonistic activities to the typical antipsychotic drugs (D$_2$ antagonists). Especially, negative symptoms must be distinguished from depression, but in either symptoms the desired pharmacological effect is activation, and it is suggested that the addition of 5-HT$_{1A}$ agonistic activity, that improves the depression, improves the negative symptoms like 5-HT$_2$ antagonistic activity.

As mentioned above, the amplificational effect of serotonergic activity are expected by addition of both 5-HT$_{1A}$ agonist and 5-HT$_2$ antagonist, therefore it is expected that the addition of both 5-HT$_{1A}$ agonist and 5-HT$_2$ antagonist to D$_2$ antagonist is more effective to the negative symptoms than the addition of either of them to it.

SUMMARY OF THE INVENTION

The present inventors have found that novel condensed thiophene compounds have D$_2$, 5-HT$_2$ antagonistic and 5-HT$_{1A}$ agonistic activities and are useful as potent antipsychotic drugs according with the above-mentioned purposes, and completed the present invention.

DETAILED DESCRIPTION

The present invention provides:

1. a condensed thiophene compound of the formula:

$$R^2\diagdown N(B)\diagup A\text{—}(CH_2)_m\diagdown \text{ring}\diagup R^1, G\text{—}Q\text{—}T \quad (CH_2)_n\text{—}D \tag{I}$$

or a pharmaceutical acceptable salt thereof.

In the above formula, the ring S means following condensed thiophenes.

[Four condensed thiophene ring structures shown with substituents $R^1$ and G—Q—T at various positions on the thiophene rings]

$R^1$ is hydrogen, halogen, alkyl, acyl or hydroxyalkyl.

$R^2$ is hydrogen, alkyl, acyl, carbamoyl, substituted carbamoyl, aryl or arylalkyl.

G is —CH$_2$—, —CH(OR$^3$)— (R$^3$ is hydrogen, alkyl or acyl), —CO—, or —S(O)t- (t is 0, 1 or 2).

Q is straight alkylene or branched chain alkylene.

T is a tertiary amino.

D is —CH$_2$— or —S(O)u- (u is 0, 1 or 2).

A and B are (i) one is absent and the other is carbonyl or thiocarbonyl, or (ii) both absent.

When A, B are the case of above-mentioned (i), m is 0 or 1, and n is 0, 1 or 2: When A, B are the case of above-mentioned (ii), m and n are the same or different and each is 0 or an integer of 1 to 4 with the proviso that m+n is an integer of below 4;

2. the compound of the above-mentioned item 1 or a pharmaceutically acceptable salt thereof, wherein T is a tertiary amino of —N(Rb)(Rc), wherein Rb and Rc are the same or different and each is alkyl, or Rb and Rc together with the adjacent nitrogen atom form a cyclic amino group of the formula:

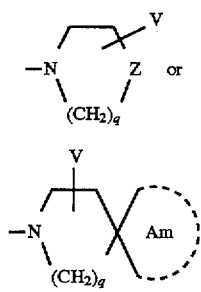

wherein q is an integer of 1 to 4, Z is methylene, or N-$R^5$ ($R^5$ is aryl, diarylalkyl, heteroaryl or heteroarylalkyl), substituent V is hydrogen, hydroxyl, heteroaryl, heteroarylalkyl or bisarylmethylene and the number of V is 1 to 4. Cyclic amino group of formula (1) may contain carbonyl group in the cycle and further may be condensed with aryl or heteroaryl. Ring Am of formula (2) contain amido bond in the cycle and further may contain oxygen atom, sulfur atom, carbonyl and/or N-$R^6$ ($R^6$ is hydrogen, alkyl or phenyl).

3. preferable compound of the above-mentioned item 1 selected from the group consisting of:
2-(2-(4-(6-fluoro-1,2- benzisoxazol-3-yl)piperidin-1-yl)ethyl)-4,6,7,8-tetrahydro-5H- thieno[3,2-b]azepin-5- one,
3-(2-(4-(6- fluoro-1,2-benzisoxazol-3-yl)piperidin-1-yl)ethyl)-2-methyl-4,6,7,8-tetrahydro-5H- thieno[3,2-b]azepin-5- one,
2-(2-(4-(6-fluoro-1,2-benzisoxazol-3-yl)piperidin-1-yl)ethyl)-4,5,6,7-tetrahydro-8 H-thieno[2,3-c]azepin-8-one,
2-(4-(6-fluoro-1,2-benzisoxazol-3-yl)piperidin-1-yl)butyryl)-4,5,6,7-tetrahydro-8H- thieno[2,3-c]azepin-8-one,
6-acetyl-3-(2-(4-(6-fluoro-1,2- benzisoxazol-3-yl)piperidin-1-yl)ethyl)-4,5,6,7-tetrahydro-2-methylthieno[2,3-c]pyridine,
6-acetyl-2-ethyl-3-(2-(4-(6-fluoro-1,2-benzisoxazol-3-yl)piperidin-1-yl)ethyl)-4,5,6,7-tetrahydrothieno[2,3-c]pyridine,
6-acetyl-2-(2-(4-(6-fluoro-1,2- benzisoxazol-3-yl)piperidin-1-yl)ethyl)-4,5,6,7-tetrahydro-3-methylthieno[2,3-c]pyridine,
6-acetyl-2-(4-(4-(6-fluoro-1,2-benzisoxazol-3-yl)piperidin-1-yl)butyryl)-4,5,6,7-tetrahydrothieno[2,3-c]pyridine,
3-(2-(4-(6-fluoro-3,2-benzisoxazol-3-yl)piperidin-1-yl)ethyl)-4,5,6,7-tetrahydro-2- methyl-6-propionylthieno[2,3-c]pyridine
6-cyclopropylcarbonyl-3-(2-(4-(6-fluoro-1,2-benzisoxazol-3-yl)piperidin-1-yl)ethyl)-4,5,6,7-tetrahydro-2-methylthieno[2,3-c]pyridine,
3,6-diacetyl-2-(2-(4-(6-fluoro-1,2-benzisoxazol-3-yl)piperidin-1-yl)ethyl)-4,5,6,7-tetrahydrothieno[2,3-c]pyridine,
6-acetyl-3-(2-(4-(6-fluorobenzo(b)thiophen-3-yl)piperidin-1-yl)ethyl)-4,5,6,7-tetrahydro-2-methyelthieno[2,3-c]pyridine,
6-acetyl-3-ethyl-2-(2-(4-(6-fluorobenzo(b)thiophen-3-yl)piperidin-1-yl)ethyl)-4,5,6,7-tetrahydrothieno[2,3-c]pyridine,
6-acetyl-3-ethyl-2-(2-(4-(6-fluorobenzo(b)furan-3-yl)piperidin-1-yl)ethyl)-4,5,6,7-tetrahydrothieno[2,3-c]pyridine, and
6-acetyl-3-ethyl-2-(2-(4-(6-fluoro-1,2-benzisothiazol-3-yl)piperidin-1-yl)ethyl)-4,5,6,7-tetrahydrothieno[2,3-c]pyridine
or a pharmaceutically acceptable salt thereof;

4. Preferable compound of the above-mentioned item 1 selected from the group consisting of:
6-acetyl-3-ethyl-2-(2-(4-(5-methylbenzo(b)furan-3-yl)piperidin-1-yl)ethyl)-4,5,6,7-tetrahydrothieno[2,3-c]pyridine,
2-(2-(4-(6-fluorobenzo(b)furan-3-yl)piperidin-1-yl)ethyl)-4,6,7,8-tetrahydro-5H- thieno[3,2-b]azepin-5-one,
2-(2-(4-(5-methylbenzo(b)furan-3-yl)piperidin-1-yl)ethyl)-4,6,7,8-tetrahydro-5H-thieno[3,2-b]azepin-5-one,
6-acetyl-3-ethyl-2-(2-(4-(5,6-dimethylbenzo(b)furan-3-yl)piperidin-1-yl)ethyl)-4,5,6,7-tetrahydrothieno[2,3-c]pyridine,
3-ethyl-2-(2-(4-(6-fluorobenzo(b)furan-3-yl)piperidin-1-yl)ethyl)-5,6,7,8-tetrahydrothieno[3,2-c]azepin-4-one,
7-acetyl-3-ethyl-2-(2-(4-(6-fluorobenzo(b)furan-3-yl)piperidin-1-yl)ethyl)-4,5,6,7-tetrahydro-8H-thieno[2,3-c]azepine,
6-acetyl-3-ethyl-2-(4-(4-(6-fluorobenzo(b)furan-3-yl)piperidin-1-yl)butyryl)-4,5,6,7-tetrahydrothieno[2,3-c]pyridine,
6- acetyl-3-ethyl-2-(2-(4-(6-methylbenzo(b)furan-3-yl)piperidin-1-yl)ethyl)-4,5,6,7-tetrahydrothieno[2,3-c]pyridine,
6-acetyl-3-ethyl-2-(2-(4-(7-methylbenzo(b)furan-3-yl)piperidin-1-yl)ethyl)-4, 5,6,7-tetrahydrothieno[2,3-c]pyridine,
2-(2-(4-(6-fluorobenzo(b)furan-3-yl)piperazin-1-yl)ethyl)-4,6,7,8-tetrahydro-5H-thieno[3,2-b]azepin-5-one,
2-(2-(4-(4-methylbenzo(b)furan-3-yl)piperazin-1-yl)ethyl)-4,6,7,8-tetrahydro-5H-thieno[3,2-b]azepin-5-one,
2-(2-(4-(6-methylbenzo(b)furan-3-yl)piperazin-1-yl)ethyl)-4,6,7,8-tetrahydro-5H- thieno[3,2-b]azepin-5- one,
2-(2-(4-(6-methylbenzo(b)thiophen-3-yl)piperazin-1-yl)ethyl)-4,6,7,8-tetrahydro-5H-thieno[3,2 -b]azepin-5- one,
6-acetyl-3-ethyl-2-(2-(4-(5- methylbenzo(b)thiophen-3-yl)piperidin-1-yl)ethyl)-4,5,6,7-tetrahydrothieno[2,3-c]pyridine,
6-acetyl-3-ethyl-2-(2-(4-(6- methylbenzo(b)thiophen-3-yl)piperidin-1-yl)ethyl)-4,5,6,7-tetrahydrothieno[2,3-c]pyridine,
6-acetyl-3-ethyl-2-(2-(4-(6-fluorobenzo(b)furan-3-yl)piperazin-1-yl)ethyl)-4,5,6,7-tetrahydrothieno[2,3-c]pyridine,
6-acetyl-3-ethyl-2-(2 -(4-(4-methylbenzo(b)furan-3-yl)piperazin-1-yl)ethyl)-4,5,6,7-tetrahydrothieno[2,3-c]pyridine,
6-acetyl-3-ethyl-2-(2-(4-(6-methylbenzo(b)furan-3-yl)piperazin-1-yl)ethyel)-4,5,6,7-tetrahydrothieno[2,3-c]pyridine,
6-acetyl-3- ethyl-2-(2-(4-(6-methylbenzo(b)thiophen-3-yl)piperazin-1-yl)ethyl)-4,5,6,7-tetrahydrothieno[2,3-c]pyridine,
2-(2-(4-(6-fluorobenzo(b)thiophen-3-yl)piperidin-1-yl)ethyl)-4,6,78-tetrahydro-5H-thieno[3,2 -b]azepin-5-one,
2-(2-(4-(6-fluorobenzo(b)thiophen-3-yl)piperidin-1-yl)ethyl)-4,5,6,7-tetrahydro-8H-thieno[2,3-c]azepin-8-one,
2-(2-(4-(6-fluorobenzo(b)furan-3-yl)piperidin-1-yl)ethyl)-4,5,6,7-tetrahydro-8H-thieno[2,3 -c]azepin-8-one,
2-(2-(4-(5-methylbenzo(b)furan-3-yl)piperidin-1-yl)ethyl)-4,5,6,7-tetrahydro-8H-thieno[2,3-c]azepin-8-one,
2-(2-(4-(6-methylbenzo(b)furan-3-yl)piperidin-1-yl)ethyl)-4,5,6,7-tetrahydro-8H- thieno[2,3-c]azepin-8-one
or a pharmaceutically acceptable salt thereof;

5. a condensed thiophene compound of the formula:

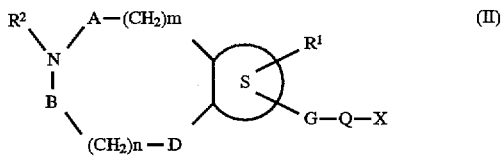

wherein X is hydroxyl, or a reactive atom or group derived from hydroxyl (halogen, methanesulfonyloxy, p-toluenesulfonyloxy and so on), and other symbols are as defined in the above-mentioned item 1;

6. a pharmaceutical composition comprising a compound of the above-mentioned item 1 and pharmaceutical additives;

7. an antipsychotic drug containing a compound of the above-mentioned item 1 as an effective ingredient.

In the definitions of the above symbols and in the present specification, halogen means chlorine, bromine, fluorine, iodine; alkyl means, for example, methyl, ethyl, propyl, isopropyl, butyl, isobutyl, tert-butyl, pentyl, hexyl, heptyl, octyl, decyl, hexadecyl or octadecyl; arylalkyl means, for example, benzyl, 1-phenylethyl, 2-phenylethyl, 3-phenylpropyl, 4-phenylbutyl, naphthylmethyl, 2-naphthylethyl, 3-naphthylpropyl, 4-naphthylbutyl, diphenylmethyl or bis(4-fluorophenyl)methyl; acyl means, for example, alkanoyl such as formyl, acetyl, propionyl, butyryl, isobutyryl, pentanoyl, hexanoyl or octanoyl, aroyl such as benzoyl or naphthoyl, heteroarylcarbonyl such as nicotinyl, thenoyl or furoyl, or cycloalkylcarbonyl such as cyclopropylcarbonyl, cyclopentylcarbonyl, cyclohexylcarbonyl or cycloheptylcarbonyl; hydroxyalkyl means, for example, hydroxymethyl, 1- or 2-hydroxyethyl, 1-, 2- or 3-hydroxypropyl or 1-, 2-, 3- or 4-hydroxybutyl; aryl means, for example, phenyl or naphthyl; substituted carbamoyl means, for example, methylcarbamoyl, ethylcarbamoyl, dimethylcarbamoyl, diethylcarbamoyl, cyclohexylcarbamoyl or piperidinocarbonyl; straight alkylene means, for example, methylene, ethylene, trimethylene, tetramethylene, pentamethylene, hexamethylene, heptamethylene, octamethylene or decamethylene; branched chain alkylene means, for example, alkylene substituted by at least one, preferably 1 to 4 alkyl(s) such as propylene, 1-methyltrimethylene, 3-methyltrimethylene, 1- methyl-tetramethylene, 4-methyltetramethylene, 1,4-dimethyltetramethylene, 6-methylhexamethylene or 4,4-dimethyltetramethylene.

In the formula (I), T is a tertiary amino of —N(Rb)(Rc). Wherein Rb and Rc are the same or different and each is alkyl (same as the above), and —N(Rb)(Rc) is exemplified by dialkylamino (e.g. dimethylamino, diethylamino, dipropylamino, diisoproylamino, dibutylamino, dihexylamino, dioctylamino), or Rb and Rc together with the adjacent nitrogen atom form a cyclic amino of the formula:

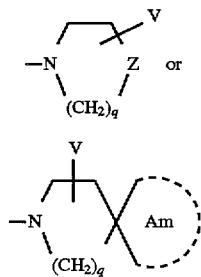

wherein q is an integer of 1 to 4, Z is methylene or N-R⁵. Substituent V is hydrogen, hydroxyl, heteroaryl (e.g. pyridyl, thienyl, furyl, pyrimidinyl, 1,2-benzoisothiazol-3-yl, 1,2-benzisoxazol-3-yl, benzothiophen-2- or 3-yl, benzofuran-2- or 3-yl, quinolyl, isoquinolyl, benzoxazol-2-yl, pyrazinyl, pyridazinyl, imidazolyl, 1H-indazol-3-yl, thieno[3,2-c]pyridin-4-yl, furo[3,2-c]pyridin-4-yl, 2-oxo-1-benzimidazolyl, 2-thioxo-1,-benzimidazolyl, 2,4-dioxohexahydro-pyrimidin-1-yl, hydantoin-1-yl), heteroarylalkyl (which may optionally be hydrogenated and is exemplified by pyridylmethyl, furylmethyl, thienylmethyl or (1,4-benzodioxan-2-yl)methyl), or bisarylmethylene (e.g. bis(4-fluorophenyl)methylene, his(4-chlorophenyl)-methylene) and the number of V is 1 to 4.

R⁵ of N-R⁵ is aryl (same as the above), diarylalkyl (e.g. diphenylmethyl, bis(4-fluorophenyl)methyl, 2,2-diphenylethyl, 2,2-bis(4-fluorophenyl)-ethyl), heteroaryl (same as the above), or heteroarylalkyl (same as the above).

Cyclic amino group of formula (1) may contain carbonyl group in the cycle and further may be fused with aryl (e.g. benzene, naphthalene) or heteroaryl (e.g. furan, thiophene, pyridine, quinoline) to form fused cyclic amino such as 1,2,3,4-tetrahydroisoquinolin-2-yl or phthalimido. Ring Am of formula (2) contain amido bond in the cycle and further may contain oxygen atom, sulfur atom, carbonyl and/or N-R⁶ (R⁶ is hydrogen, alkyl or phenyl). The ring Am having amido bond in the cycle includes, for example, thiazolidinone, imidazolidinone, pyrazolidinone or pyrrolidinone.

In the above definitions, the aryl and heteroaryl may optionally be substituted by 1 to 3 substituents (e.g. halogen, nitro, amino, cyano, haloalkyl, hydroxyl, alkyl, alkoxy or alkenyl) on the aromatic ring.

Preferable embodiments of T are the group represented by the formula:

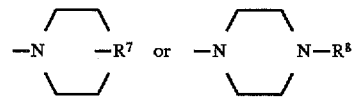

wherein R⁷ is 1,2-benzisoxazol-3-yl, 1,2-benzisothiazol-3-yl, benzo(b)furan-3-yl, benzo(b)thiophen-e3-yl, 1,1-dioxobenzo(b)thiophen-3-yl or 1H-indazol-3-yl, which may have 1 or 2 substituents selected from the group consisting of halogen, $C_{1-4}$ alkyl (e.g., methyl, ethyl), $C_{1-4}$ alkoxy (e.g., methoxy, ethoxy), $C_{2-4}$ alkanoyl (e.g., acetyl, propionyl) and 4-fluorophenyl; benzoyl which may have 1 to 3 substituents selected from the group consisting of halogen, hydroxy, $C_{1-4}$ alkyl and $C_{1-4}$ alkoxy; or bis(4-fluorophenyl)methylene; R⁸ is 1,2-bezisoxazol-3-yl, 1,2-benzisothiazol-3-yl, benzo(b)furan-3-yl, benzo(b)thiophen-e3-yl or benzothiazol-2-yl, which may have 1 or 2 substituents selected from the group consisting of halogen, $C_{1-4}$ alkyl and $C_{1-4}$ alkoxy.

More preferable embodiments of T are exemplified by 4-(6-fluoro-1,2-benzisoxazol-3-yl)piperidin-1-yl, 4-(5-fluoro- 1,2-benzisoxazol-3-yl)piperidin-1-yl, 4-(6-fluoro-1,2-benzisothiazol-3-yl)piperidin- 1-yl, 4-(1,2-benzisothiazol-3-yl)piperidin-1-yl, 4-(6-fluorobenzo(b) thiophen-3-yl)piperidin-1-yl, 4-(6-fluoro-1H-indazol-3-yl) piperidin-1-yl, 4-(6-fluoro-1-(4-fluorophenyl)-1H-indazol-3-yl)piperidin-1-yl, 4-(1,2-benzisoxazol-3-yl)piperidin-1-yl, 4-(6-fluorobenzo(b)furan-3-yl)piperidin-1-yl, 4-(4-fluoro-2-methoxybenzoyl)piperidin-1-yl, 4-(2,4-difluorobenzoyl) piperidin-1-yl, 4-(2-acetyl-6-fluorobenzo(b)thiophen-3-yl) piperidin-1-yl, 4-(2-ethyl-6-fluorobenzo(b)thiophen-3-yl) piperidin-1-yl, 4-(2-methyl-6-fluoro-benzo(b)thiophen-3-yl)piperidin-1-yl, 4-(2-ethyl-6-fluorobenzo(b)furan-3-yl) piperidin-1-yl, 4-(1,2-benzisoxazol-3-yl)piperazin-1-yl, 4-(1,2-benzisothiazol-3-yl)piperazin-1-yl, 4-(6-chlorobenzothiazol-2-yl)piperazin-1-yl, 4-(6-fluoro-1,1-dioxobenzo(b)thiophen-3-yl)piperidin-1-yl, 4-(6-methoxy-1,2-benzisoxazol-3-yl)piperidin-1-yl, 4-(5-methylbenzo(b)furan-3-yl)piperidin-1-yl, 4-(4,6-dichlorobenzo(b)furan-3-yl)piperidin-1-yl, 4-(6-fluoro-2-methylbenzo(b)furan-3-yl)piperidin-1-yl, 4-(5-chlorobenzo(b)furan-3-yl)piperidin-1-yl, 4-(5-fluorobenzo(b)furan-3-yl)piperidin-1-yl, 4-(5-methoxybenzo(b)furan-3-yl)piperidin-1-yl, 4-(5-bromobenzo(b)furan-3-yl)piperidin-1-yl, 4-(5,6-dimethylbenzo(b)furan-3-yl)piperidin-1-yl, 4-(4,6-dimethylbenzo(b)furan-3-yl)piperidin-1-yl, 4-(5,7-dimethyl-benzo(b)furan-3-yl)piperidin-1-yl, 4-(bis(4-fluorophenyl)methylene)-piperidin-1- yl, 4- (4-hydroxy-2,6-dimethylbenzoyl)piperidin-1-yl, 4-(5-chloro-6-methylbenzo(b)furan-3-yl)piperidin-1-yl, 4-(6-methyl-benzo(b)furan-3-yl)piperidin-1-yl, 4-(5-chloro-2-hydroxybenzoyl)-piperidin-1-yl, 4-(7-methylbenzo(b)furan-3-yl)piperidin-1-yl, 4-(2-hydroxy-5-methylbenzoyl)piperidin-1-yl, 4-(benzo(b)furan-3-yl)piperidin-1-yl, 4-(4-methylbenzo(b)furan- 3-yl) piperidin-1-yl, 4-(4-methylbenzo(b)thiophen-e3-yl) piperidin-1-yl, 4-(5-methylbenzo(b)thiophen-3-yl) piperidin-1-yl, 4-(6-methylbenzo(b)-thiophen-3-yl) piperidin-1-yl, 4-(7-methylbenzo(b)thiophen-3-yl) piperidin-1-yl, 4-(4-fluorobenzo(b)furan-3-yl)piperazin-1-yl, 4-(5-fluorobenzo(b)furan-3-yl)piperazin-1-yl, 4-(6-fluorobenzo(b)furan-3-yl)piperazin-1-yl, 4-(7-fluorobenzo (b)furan-3-yl)piperazin-1-yl, 4-(4-methylbenzo(b)furan-3-yl)piperazin-1-yl, 4-(5-methylbenzo(b)furan-3-yl)piperazin-1-yl, 4-(6-methylbenzo(b)furan-3-yl)piperazin-1-yl, 4-(7-methylbenzo(b)furan-3-yl)piperazin-1-yl, 4-(4-fluorobenzo (b)thiophen-3-yl)piperazin-1-yl, 4-(5-fluorobenzo(b) thiophen-3-yl)piperazin- 1-yl, 4-(6-fluorobenzo(b)thiophen-3-yl)piperazin-1-yl, 4-(7-fluorobenzo(b)-thiophen-3-yl) piperazin-1-yl, 4-(4-methylbenzo(b)thiophen-3-yl)-piperazin-1-yl, 4-(5-methylbenzo(b)thiophen- 3-yl) piperazin- 1-yl, 4-(6-methylbenzo(b)-thiophen-3-yl) piperazin-1-yl, 4-(7- methylbenzo(b)-thiophen-3-yl) piperazin-1-yl, and so on.

The salt of the compound of formula (I) include an acid addition salt such as hydrochloride, hydrobromide, phosphate, sulfate, benzenesulfonate, methanesulfonate, citrate, lactate, maleate, fumarate or tartarate. When the compound of formula (I) contain carboxyel as a substituent, the salt includes a metal salt such as sodium salt, potassium salt, calcium salt, aluminum salt, or an amine salt with triethylamine, or bibasic amino acid salt with lysine etc. The pharmaceutically acceptable salts thereof are preferable. The present invention also includes a hydrate and a solvate of the compound of formula (I).

The compounds of formula (I) or (II) having a chiral carbon atom can be prepared as a racemate or an optically active isomer, and the compound having at least two chiral atoms can be obtained as an individual diastereomer or a mixture thereof. The present invention embraces the mixture thereof and the individual isomers. Furthermore, the present invention embraces stereoisomers.

The methods for preparing the compounds of present invention are described as follows:

Method (1)

The compound of formula (I) can be synthesized by reacting the compound of formula (II) with a compound of the formula:

H-T  (III)

wherein T is as defined above, or acid addition salt thereof.

The reaction is carried out in an inert solvent such as methanol, ethanol, propanol, benzene, toluene, dimethylformamide, tetrahydrofuran, acetonitrile or acetone in the presence of a suitable acid scavenger (e.g. potassium carbonate, sodium carbonate, sodium hydrogencarbonate, pyridine, triethylamine, sodium acetate or potassium acetate) at 20° C.–150° C. for 30 minutes to e30 hours.

When X in the compound of formula (II) is hydroxyl, the reaction is carried out in a suitable inert solvent such as dimethylformamide or benzene in the presence of an aminophosphonium reagent (e.g. N,N-methyl-phenylaminotriphenylphosphonium iodide)at 20° C.–150° C. for 30 minutes to 5 hours.

Method (2)

The compound of formula (I) can be synthesized by reacting a compound of the formula:

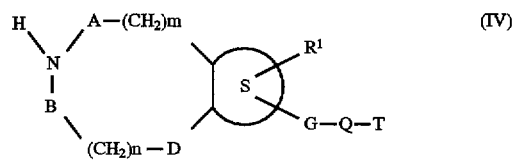

wherein each symbol is as defined above, with a compound of the formula:

wherein each symbol is as defined above.

The reaction is carried out in an inert solvent such as methanol, ethanol, propanol, N,N-dimethylformamide, benzene, toluene, acetonitrile, diethyl ether, tetrahydrofuran or n-hexane in the presence of a suitable base such as sodium methoxide, sodium ethoxide, potassium tert-butoxide, potassium hydride, sodium hydride, sodium hydroxide, potassium hydroxide, sodium carbonate or potassium carbonate at −20 C.–150° C. for 30 minutes to 5 hours.

Method (3)

The synthetic intermediate compound of formula (II) wherein G is —CO— can be prepared by reacting a compound of the formula:

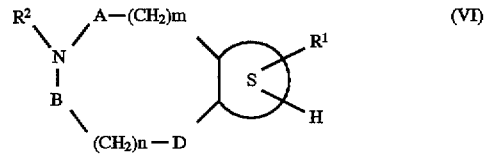

wherein each symbol is as defined above, with a compound of the formula:

$Z^1$-CO-Q-X  (VII)

wherein $Z^1$ is halogen and other symbols are as defined above.

The reaction is carried out in a suitable and inert solvent such as chloroform, dichloromethane or dichloroethane in the presence of a suitable Lewis acid (e.g. tin chloride, aluminum chloride, iron chloride, zinc chloride) at −10° C. to 100° C. for 30 minutes to 5 hours.

Method (4)

The synthetic intermediate compound of formula (II) wherein G is —S— can be prepared by lithiation of the compound of formula (VI) using a suitable alkyl-lithium, followed by reaction with a compound of the formula:

X¹-Q-X²     (VIII)

wherein X¹ and X² are the same as the above-mentioned X, but both of them are not hydroxyl, in the presence of sulfur.

The reaction is carried out by lithiation using a suitable alkyl-lithium such as butyllithium or sec-butyllithium in a suitable and inert solvent such as diethyl ether or tetrahydrofuran at a temperature of from −78° C. to the boiling point of the solvent employed, and followed by reaction with sulfur and the compound of formula (VIII).

Method (5)

The synthetic intermediate compound of formula (II) wherein G is —SO— or —SO₂— can be prepared by oxidizing the compound synthesized in Method (4) using a suitable oxidizing agent (e.g. sodium metaperiodate) in a suitable solvent.

Method (6)

The synthetic intermediate compound of formula (II) wherein G is —CH(OH)— or —CH₂— can be prepared by reducing the compound obtained in Method (3) wherein G is —CO— using a suitable reducing agent such as sodium borohydride.

The reaction is carried out in a suitable and inert solvent, for example, methanol, ethanol, propanol, isoproyl alcohol, tetrahydrofuran, dichloromethane or dichloroethane, in the presence of a suitable reducing agent (e.g. lithium aluminum hydride, sodium borohydride, sodium cyanoborohydride, trifluoroboron diethylate, triethylsilane) at −10° C. to 100° C. for 30 minutes to 10 hours. The compound of formula (I) wherein G is –CH(OH)— or —CH₂— can be prepared by reducing the compound of formula (I) wherein G is —CO— in a similar manner as the above-mentioned method.

Method (7)

The compound of formula (I) wherein G is —CH(OR³')— (R³' is alkyl or acyl) can be prepared by reacting the compound of formula (I) wherein G is —CH(OH)— with a compound of the formula:

R³'-Z²     (IX)

wherein Z² is halogen and R³ is as defined above.

The reaction is carried out in a suitable and inert solvent such as methanol, ethanol, propanol, butanol, N,N-dimethylformamide, tetrahydrofuran, benzene or toluene in the presence of an acid scavenger (e.g. sodium hydride, sodium amide, sodium methoxide, sodium ethoxide, potassium hydroxide, sodium hydroxide) at room temperature to 150° C. for 1 to 20 hours.

The compound of formula (VI) wherein one of A and B is absent and the other is carbonyl group can be synthesized by, for example, the following methods.

Method (8)

A method which comprises subjecting a compound of the formula:

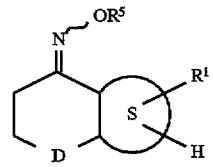     (XVIII)

wherein each symbol is as defined above, to Schmidt rearrangement.

The reaction is carried out by reacting the compound of formula (XVIII) with sodium azide in a suitable and inert solvent such as chloroform, methylene chloride, toluene or benzene or without a solvent in the presence of a suitable acid (e.g. trifluoroacetic acid, polyphosphoric acid, sulfuric acid) at 0° C. to 150° C. for 30 minutes to 10 hours.

Method (9)

A method which comprises subjecting a compound of the formula:

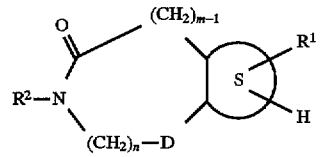     (XIX)

wherein R⁵ is hydrogen, alkyl, methanensulfonyl group or p-toluene-sulfonyl group and other symbols are as defined above, to Beckmann rearrangement.

The reaction is carried out by reacting the compound of formula (XIX) in a suitable and inert solvent such as benzene, toluene, dimethylformamide or diethyl ether or without solvent in the presence of a suitable acid (e.g. phosphoric acid, phosphorus oxychloride, phosphorus pentachloride, phosphorus pentoxide, polyphosphoric acid, sulfuric acid) at 0° C. to 150° C. for 30 minutes to 10 hours.

The compound of formula (VI) wherein both of A and B are absent can be synthesized by, for example, the following method.

Method (10)

A method which comprises reducing a compound of the formula:

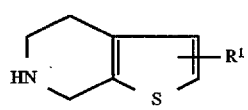     (XX)

wherein each symbol is as defined above.

The reaction is carried out using boron trifluoride-ether complex and sodium borohydride in a suitable and inert solvent such as ether or tetrahydrofuran at 0° C. to the boiling point of the solvent employed for 30 minutes to 10 hours.

Method (11)

The synthetic intermediate compound of the formula:

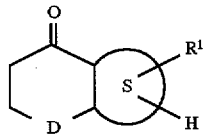     (XXI)

wherein R¹ is as defined above, can be prepared by the following method.

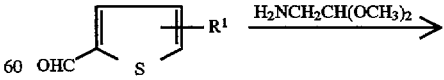

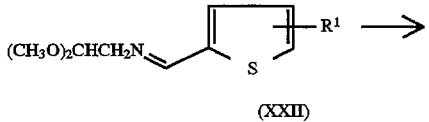

(XXII)

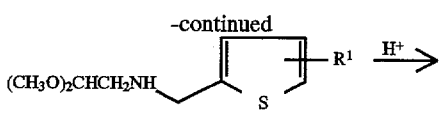

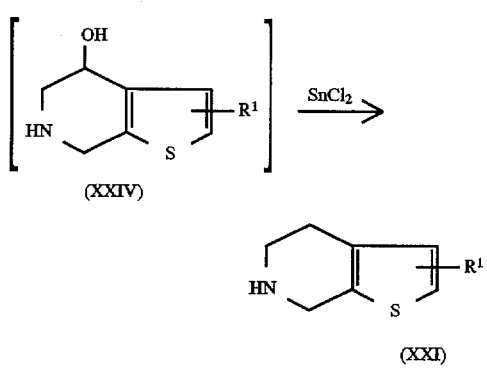

The compound of formula (XXII) can be prepared by a dehydration condensation of the corresponding aldehyde compound with aminoacetoaldehyde dimethyl acetal. The reaction is carried out in a suitable and inert solvent, for example, tetrahydrofuran, diethyl ether, methylene chloride, benzene or toluene, preferably without solvent at 10° C. to 100° C. for 30 minutes to 10 hours.

The compound of formula (XXIII) can be prepared by reducing the compound of formula (XXII) using a reducing agent such as sodium cyano-borohydride, lithium aluminum hydride, aluminum hydride or diisobutylaluminum hydride, preferably sodium borohydride in an inert solvent such as ethanol, butanol, isopropyl alcohol or tetrahydrofuran at −20° C. to 100° C. for 30 minutes to 15 hours.

The compound of formula (XXIV) can be prepared by reacting the compound of formula (XXIII) with an acid such as sulfuric acid, p-toluenesulfonic acid or phosphoric acid, prefebrably hydrochloric acid, in an inert solvent such as water, tetrahydrofuran, diethyl ether or dioxane, preferably in water at 0° C. to 120° C. for 30 minutes to 15 hours.

The compound of formula (XXI) can be prepared by reacting the compound of formula (XXIV), which usually may not be isolated and purified, with a reducing agent such as a tin(II) chloride in a solvent such as water, tetrahydrofuran, diethyl ether or dioxane, preferably in water, in the presence of an acid such as sulfuric acid, p-toluenesulfonic acid, phosphoric acid, preferably hydrochloric acid at 0° C. to 120° C. for 30 minutes to 15 hours.

The thus obtained compounds of the present invention can be isolated and purified by a conventional method such as recrystallization or column chromatography.

When the obtained compound is a racemate, it can be separated into desired optically active isomers, for example, by means of fractional recrystallization of a salt with an optically active acid or column filled with an optically active carrier. Individual diastereomers can be separated by the method such as fractional crystallizatin or chromatography. Such compounds can also be obtained by using an optically active starting material. Furthermore, the stereoisomers can be isolated by recrystallization, column chromatography or the like.

The compounds exemplified in the examples and listed in the following tables, or salts thereof are encompassed in the condensed thiophene compounds of formula (I) of the present invention. In the tables, "Me" means methyl, "Et" means ethyl, "$C_6H_5$" means phenyl, and the symbols "I" to "X" in "T" means the following amine molecules:

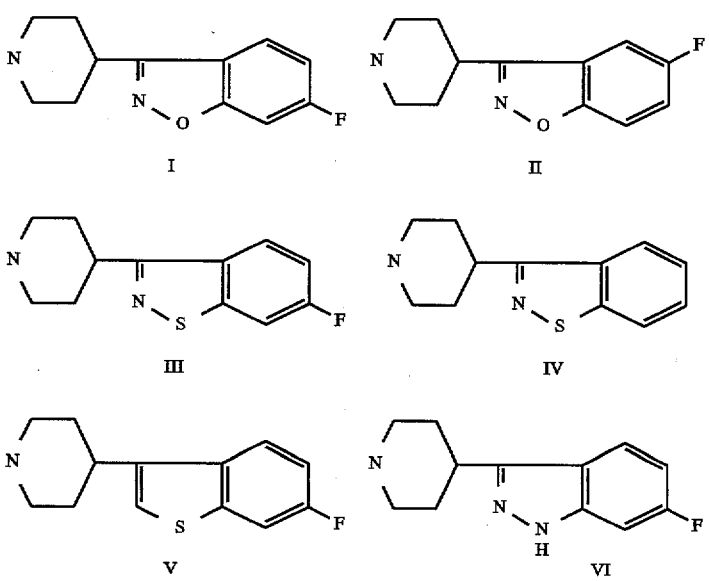

-continued

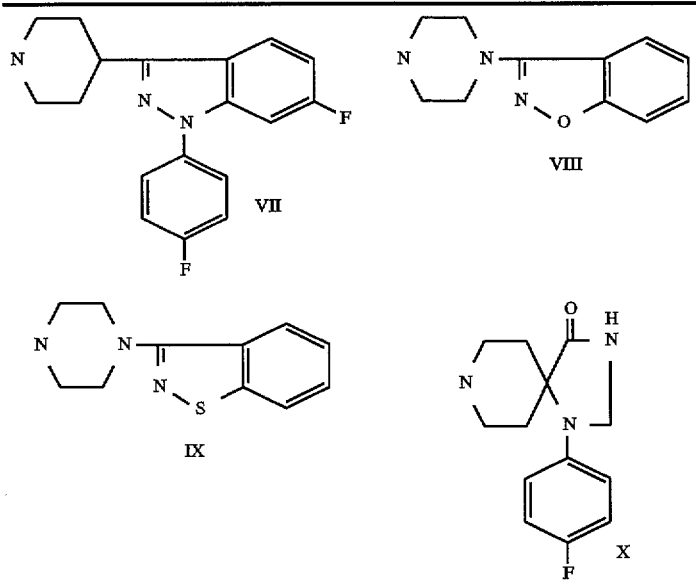

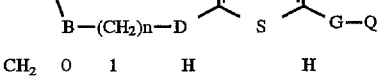

| No. | A | B | D | m | n | R1 | R2 | G | Q | T |
|---|---|---|---|---|---|---|---|---|---|---|
| 1 | — | CO | CH$_2$ | 0 | 1 | H | H | CO | (CH$_2$)$_3$ | I |
| 2 | — | CO | CH$_2$ | 0 | 1 | Me | H | CO | (CH$_2$)$_3$ | I |
| 3 | — | CO | CH$_2$ | 0 | 1 | Et | H | CO | (CH$_2$)$_3$ | I |
| 4 | — | CO | CH$_2$ | 0 | 1 | COCH$_3$ | H | CO | (CH$_2$)$_3$ | I |
| 5 | — | CO | CH$_2$ | 0 | 1 | COC$_6$H$_5$ | H | CO | (CH$_2$)$_3$ | I |
| 6 | — | CO | CH$_2$ | 0 | 1 | F | H | CO | (CH$_2$)$_3$ | I |
| 7 | — | CO | CH$_2$ | 0 | 1 | Cl | H | CO | (CH$_2$)$_3$ | I |
| 42 | — | CO | CH$_2$ | 0 | 1 | H | H | CH$_2$ | CH$_2$ | I |
| 43 | — | CO | CH$_2$ | 0 | 1 | Me | H | CH$_2$ | CH$_2$ | I |
| 44 | — | CO | CH$_2$ | 0 | 1 | Et | H | CH$_2$ | CH$_2$ | I |
| 45 | — | CO | CH$_2$ | 0 | 1 | COCH$_3$ | H | CH$_2$ | CH$_2$ | I |
| 48 | — | CO | CH$_2$ | 0 | 1 | COC$_6$H$_5$ | H | CH$_2$ | CH$_2$ | I |
| 47 | — | CO | CH$_2$ | 0 | 1 | F | H | CH$_2$ | CH$_2$ | I |
| 48 | — | CO | CH$_2$ | 0 | 1 | Cl | H | CH$_2$ | CH$_2$ | I |
| 49 | — | CO | CH$_2$ | 0 | 1 | Br | H | CH$_2$ | CH$_2$ | I |
| 83 | CO | — | CH$_2$ | 0 | 1 | H | H | CO | (CH$_2$)$_3$ | I |
| 84 | CO | — | CH$_2$ | 0 | 1 | Me | H | CO | (CH$_2$)$_3$ | I |
| 85 | CO | — | CH$_2$ | 0 | 1 | Et | H | CO | (CH$_2$)$_3$ | I |
| 86 | CO | — | CH$_2$ | 0 | 1 | COCH$_3$ | H | CO | (CH$_2$)$_3$ | I |
| 87 | CO | — | CH$_2$ | 0 | 1 | COC$_6$H$_5$ | H | CO | (CH$_2$)$_3$ | I |
| 88 | CO | — | CH$_2$ | 0 | 1 | F | H | CO | (CH$_2$)$_3$ | I |
| 89 | CO | — | CH$_2$ | 0 | 1 | Cl | H | CO | (CH$_2$)$_3$ | I |
| 90 | CO | — | CH$_2$ | 0 | 1 | Br | H | CO | (CH$_2$)$_3$ | I |
| 124 | CO | — | CH$_2$ | 0 | 1 | H | H | CH$_2$ | CH$_2$ | I |
| 125 | CO | — | CH$_2$ | 0 | 1 | Me | H | CH$_2$ | CH$_2$ | I |
| 126 | CO | — | CH$_2$ | 0 | 1 | Et | H | CH$_2$ | CH$_2$ | I |
| 127 | CO | — | CH$_2$ | 0 | 1 | COCH$_3$ | H | CH$_2$ | CH$_2$ | I |
| 128 | CO | — | CH$_2$ | 0 | 1 | COC$_6$H$_5$ | H | CH$_2$ | CH$_2$ | I |
| 129 | CO | — | CH$_2$ | 0 | 1 | F | H | CH$_2$ | CH$_2$ | I |
| 130 | CO | — | CH$_2$ | 0 | 1 | Cl | H | CH$_2$ | CH$_2$ | I |
| 131 | CO | — | CH$_2$ | 0 | 1 | Br | H | CH$_2$ | CH$_2$ | I |
| 165 | — | CO | CH$_2$ | 1 | 0 | H | H | CO | (CH$_2$)$_3$ | I |
| 166 | — | CO | CH$_2$ | 1 | 0 | Me | H | CO | (CH$_2$)$_3$ | I |
| 167 | — | CO | CH$_2$ | 1 | 0 | Et | H | CO | (CH$_2$)$_3$ | I |
| 168 | — | CO | CH$_2$ | 1 | 0 | COCH$_3$ | H | CO | (CH$_2$)$_3$ | I |
| 169 | — | CO | CH$_2$ | 1 | 0 | COC$_6$H$_5$ | H | CO | (CH$_2$)$_3$ | I |
| 189 | — | CO | CH$_2$ | 0 | 2 | H | H | CO | (CH$_2$)$_3$ | I |
| 190 | — | CO | CH$_2$ | 0 | 2 | Me | H | CO | (CH$_2$)$_3$ | I |
| 191 | — | CO | CH$_2$ | 0 | 2 | Et | H | CO | (CH$_2$)$_3$ | I |
| 192 | — | CO | CH$_2$ | 0 | 2 | COCH$_3$ | H | CO | (CH$_2$)$_3$ | I |
| 193 | — | CO | CH$_2$ | 0 | 2 | COC$_6$H$_5$ | H | CO | (CH$_2$)$_3$ | I |
| 194 | — | CO | CH$_2$ | 0 | 2 | Br | H | CO | (CH$_2$)$_3$ | I |
| 195 | — | CO | CH$_2$ | 0 | 2 | H | H | CH$_2$ | CH$_2$ | I |
| 196 | — | CO | CH$_2$ | 0 | 2 | Me | H | CH$_2$ | CH$_2$ | I |

-continued

| No. | A | B | D | n | m | R1 | R2 | G | Q | T |
|---|---|---|---|---|---|---|---|---|---|---|
| 197 | — | CO | CH₂ | 0 | 2 | Et | H | CH₂ | CH₂ | I |
| 198 | — | CO | CH₂ | 0 | 2 | COCH₃ | H | CH₂ | CH₂ | I |
| 199 | — | CO | CH₂ | 0 | 2 | COC₆H₅ | H | CH₂ | CH₂ | I |
| 200 | — | CO | CH₂ | 0 | 2 | Br | H | CH₂ | CH₂ | I |
| 201 | CO | — | CH₂ | 0 | 2 | H | H | CO | (CH₂)₃ | I |
| 202 | CO | — | CH₂ | 0 | 2 | Me | H | CO | (CH₂)₃ | I |
| 203 | CO | — | CH₂ | 0 | 2 | Et | H | CO | (CH₂)₃ | I |
| 204 | CO | — | CH₂ | 0 | 2 | COCH₃ | H | CO | (CH₂)₃ | I |
| 205 | CO | — | CH₂ | 0 | 2 | COC₆H₅ | H | CO | (CH₂)₃ | I |
| 206 | Co | — | CH₂ | 0 | 2 | Br | H | CO | (CH₂)₃ | I |
| 207 | CO | — | CH₂ | 0 | 2 | H | H | CH₂ | CH₂ | I |
| 208 | CO | — | CH₂ | 0 | 2 | Me | H | CH₂ | CH₂ | I |
| 209 | CO | — | CH₂ | 0 | 2 | Et | H | CH₂ | CH₂ | I |
| 210 | CO | — | CH₂ | 0 | 2 | COCH₃ | H | CH₂ | CH₂ | I |
| 211 | CO | — | CH₂ | 0 | 2 | COC₆H₅ | H | CH₂ | CH₂ | I |
| 212 | CO | — | CH₂ | 0 | 2 | Br | H | CH₂ | CH₂ | I |
| 261 | — | CO | CH₂ | 0 | 3 | H | H | CO | (CH₂)₃ | I |
| 262 | — | CO | CH₂ | 0 | 3 | Me | H | CO | (CH₂)₃ | I |
| 263 | — | CO | CH₂ | 0 | 3 | Et | H | CO | (CH₂)₃ | I |
| 264 | — | CO | CH₂ | 0 | 3 | COCH₃ | H | CO | (CH₂)₃ | I |
| 265 | — | CO | CH₂ | 0 | 3 | COC₆H₅ | H | CO | (CH₂)₃ | I |
| 266 | — | CO | CH₂ | 0 | 3 | Br | H | CO | (CH₂)₃ | I |
| 267 | — | CO | CH₂ | 0 | 3 | H | H | CH₂ | CH₂ | I |
| 268 | — | CO | CH₂ | 0 | 3 | Me | H | CH₂ | CH₂ | I |
| 269 | — | CO | CH₂ | 0 | 3 | Et | H | CH₂ | CH₂ | I |
| 270 | — | CO | CH₂ | 0 | 3 | COCH₃ | H | CH₂ | CH₂ | I |
| 271 | — | CO | CH₂ | 0 | 3 | COC₆H₅ | H | CH₂ | CH₂ | I |
| 272 | — | CO | CH₂ | 0 | 3 | Br | H | CH₂ | CH₂ | I |
| 273 | CO | — | CH₂ | 0 | 3 | H | H | CO | (CH₂)₃ | I |
| 274 | CO | — | CH₂ | 0 | 3 | Me | H | CO | (CH₂)₃ | I |
| 275 | CO | — | CH₂ | 0 | 3 | Et | H | CO | (CH₂)₃ | I |
| 276 | CO | — | CH₂ | 0 | 3 | COCH₃ | H | CO | (CH₂)₃ | I |
| 277 | CO | — | CH₂ | 0 | 3 | COC₆H₅ | H | CO | (CH₂)₃ | I |
| 278 | CO | — | CH₂ | 0 | 3 | Br | H | CO | (CH₂)₃ | I |
| 279 | CO | — | CH₂ | 0 | 3 | H | H | CH₂ | CH₂ | I |
| 280 | CO | — | CH₂ | 0 | 3 | Me | H | CH₂ | CH₂ | I |
| 281 | CO | — | CH₂ | 0 | 3 | Et | H | CH₂ | CH₂ | I |
| 282 | CO | — | CH₂ | 0 | 3 | COCH₃ | H | CH₂ | CH₂ | I |
| 283 | CO | — | CH₂ | 0 | 3 | COC₆H₅ | H | CH₂ | CH₂ | I |
| 284 | CO | — | CH₂ | 0 | 3 | Br | H | CH₂ | CH₂ | I |

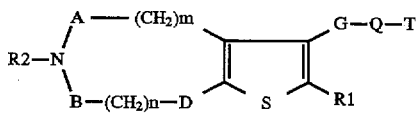

| No. | A | B | D | n | m | R1 | R2 | G | Q | T |
|---|---|---|---|---|---|---|---|---|---|---|
| 357 | — | CO | CH₂ | 0 | 1 | H | H | CO | (CH₂)₃ | I |
| 358 | — | CO | CH₂ | 0 | 1 | Me | H | CO | (CH₂)₃ | I |
| 359 | — | CO | CH₂ | 0 | 1 | Et | H | CO | (CH₂)₃ | I |
| 360 | — | CO | CH₂ | 0 | 1 | COCH₃ | H | CO | (CH₂)₃ | I |
| 361 | — | CO | CH₂ | 0 | 1 | COC₆H₅ | H | CO | (CH₂)₃ | I |
| 362 | — | CO | CH₂ | 0 | 1 | F | H | CO | (CH₂)₃ | I |
| 363 | — | CO | CH₂ | 0 | 1 | Cl | H | CO | (CH₂)₃ | I |
| 364 | — | CO | CH₂ | 0 | 1 | Br | H | CO | (CH₂)₃ | I |
| 397 | — | CO | CH₂ | 0 | 1 | NMe₂ | H | CO | (CH₂)₃ | I |
| 398 | — | CO | CH₂ | 0 | 1 | H | H | CH₂ | CH₂ | I |
| 399 | — | CO | CH₂ | 0 | 1 | Me | H | CH₂ | CH₂ | I |
| 400 | — | CO | CH₂ | 0 | 1 | Et | H | CH₂ | CH₂ | I |
| 401 | — | CO | CH₂ | 0 | 1 | COCH₃ | H | CH₂ | CH₂ | I |
| 402 | — | CO | CH₂ | 0 | 1 | COC₆H₅ | H | CH₂ | CH₂ | I |
| 403 | — | CO | CH₂ | 0 | 1 | F | H | CH₂ | CH₂ | I |
| 404 | — | CO | CH₂ | 0 | 1 | Cl | H | CH₂ | CH₂ | I |
| 405 | — | CO | CH₂ | 0 | 1 | Br | H | CH₂ | CH₂ | I |
| 439 | CO | — | CH₂ | 0 | 1 | H | H | CO | (CH₂)₃ | I |
| 440 | CO | — | CH₂ | 0 | 1 | Me | H | CO | (CH₂)₃ | I |
| 441 | CO | — | CH₂ | 0 | 1 | Et | H | CO | (CH₂)₃ | I |
| 442 | CO | — | CH₂ | 0 | 1 | COCH₃ | H | CO | (CH₂)₃ | I |
| 443 | CO | — | CH₂ | 0 | 1 | COC₆H₅ | H | CO | (CH₂)₃ | I |
| 444 | CO | — | CH₂ | 0 | 1 | F | H | CO | (CH₂)₃ | I |
| 445 | CO | — | CH₂ | 0 | 1 | Cl | H | CO | (CH₂)₃ | I |
| 446 | CO | — | CH₂ | 0 | 1 | Br | H | CO | (CH₂)₃ | I |
| 480 | CO | — | CH₂ | 0 | 1 | H | H | CH₂ | CH₂ | I |
| 481 | CO | — | CH₂ | 0 | 1 | Me | H | CH₂ | CH₂ | I |
| 482 | CO | — | CH₂ | 0 | 1 | Et | H | CH₂ | CH₂ | I |
| 483 | CO | — | CH₂ | 0 | 1 | COCH₃ | H | CH₂ | CH₂ | I |
| 484 | CO | — | CH₂ | 0 | 1 | COC₆H₅ | H | CH₂ | CH₂ | I |
| 485 | CO | — | CH₂ | 0 | 1 | F | H | CH₂ | CH₂ | I |
| 486 | CO | — | CH₂ | 0 | 1 | Cl | H | CH₂ | CH₂ | I |
| 487 | CO | — | CH₂ | 0 | 1 | Br | H | CH₂ | CH₂ | I |

| | | | | | | | | | | |
|---|---|---|---|---|---|---|---|---|---|---|
| 521 | — | CO | CH$_2$ | 1 | 0 | H | H | CO | (CH$_2$)$_3$ | I |
| 522 | — | CO | CH$_2$ | 1 | 0 | Me | H | CO | (CH$_2$)$_3$ | I |
| 523 | — | CO | CH$_2$ | 1 | 0 | Et | H | CO | (CH$_2$)$_3$ | I |
| 524 | — | CO | CH$_2$ | 1 | 0 | COCH$_3$ | H | CO | (CH$_2$)$_3$ | I |
| 545 | — | CO | CH$_2$ | 0 | 2 | H | H | CO | (CH$_2$)$_3$ | I |
| 546 | — | CO | CH$_2$ | 0 | 2 | Me | H | CO | (CH$_2$)$_3$ | I |
| 547 | — | CO | CH$_2$ | 0 | 2 | Et | H | CO | (CH$_2$)$_3$ | I |
| 548 | — | CO | CH$_2$ | 0 | 2 | COCH$_3$ | H | CO | (CH$_2$)$_3$ | I |
| 549 | — | CO | CH$_2$ | 0 | 2 | COC$_6$H$_5$ | H | CO | (CH$_2$)$_3$ | I |
| 550 | — | CO | CH$_2$ | 0 | 2 | Br | H | CO | (CH$_2$)$_3$ | I |
| 551 | — | CO | CH$_2$ | 0 | 2 | H | H | CH$_2$ | CH$_2$ | I |
| 552 | — | CO | CH$_2$ | 0 | 2 | Me | H | CH$_2$ | CH$_2$ | I |
| 553 | — | CO | CH$_2$ | 0 | 2 | Et | H | CH$_2$ | CH$_2$ | I |
| 554 | — | CO | CH$_2$ | 0 | 2 | COCH$_3$ | H | CH$_2$ | CH$_2$ | I |
| 555 | — | CO | CH$_2$ | 0 | 2 | COC$_6$H$_5$ | H | CH$_2$ | CH$_2$ | I |
| 556 | — | CO | CH$_2$ | 0 | 2 | Br | H | CH$_2$ | CH$_2$ | I |
| 557 | CO | — | CH$_2$ | 0 | 2 | H | H | CO | (CH$_2$)$_3$ | I |
| 558 | CO | — | CH$_2$ | 0 | 2 | Me | H | CO | (CH$_2$)$_3$ | I |
| 559 | CO | — | CH$_2$ | 0 | 2 | Et | H | CO | (CH$_2$)$_3$ | I |
| 560 | CO | — | CH$_2$ | 0 | 2 | COCH$_3$ | H | CO | (CH$_2$)$_3$ | I |
| 561 | CO | — | CH$_2$ | 0 | 2 | COC$_6$H$_5$ | H | CO | (CH$_2$)$_3$ | I |
| 562 | CO | — | CH$_2$ | 0 | 2 | Br | H | CO | (CH$_2$)$_3$ | I |
| 563 | CO | — | CH$_2$ | 0 | 2 | H | H | CH$_2$ | CH$_2$ | I |
| 564 | CO | — | CH$_2$ | 0 | 2 | Me | H | CH$_2$ | CH$_2$ | I |
| 565 | CO | — | CH$_2$ | 0 | 2 | Et | H | CH$_2$ | CH$_2$ | I |
| 566 | CO | — | CH$_2$ | 0 | 2 | COCH$_3$ | H | CH$_2$ | CH$_2$ | I |
| 567 | CO | — | CH$_2$ | 0 | 2 | COC$_6$H$_5$ | H | CH$_2$ | CH$_2$ | I |
| 568 | CO | — | CH$_2$ | 0 | 2 | Br | H | CH$_2$ | CH$_2$ | I |
| 617 | — | CO | CH$_2$ | 0 | 3 | H | H | CO | (CH$_2$)$_3$ | I |
| 618 | — | CO | CH$_2$ | 0 | 3 | Me | H | CO | (CH$_2$)$_3$ | I |
| 619 | — | CO | CH$_2$ | 0 | 3 | Et | H | CO | (CH$_2$)$_3$ | I |
| 620 | — | CO | CH$_2$ | 0 | 3 | COCH$_3$ | H | CO | (CH$_2$)$_3$ | I |
| 621 | — | CO | CH$_2$ | 0 | 3 | COC$_6$H$_5$ | H | CO | (CH$_2$)$_3$ | I |
| 622 | — | CO | CH$_2$ | 0 | 3 | Br | H | CO | (CH$_2$)$_3$ | I |
| 623 | — | CO | CH$_2$ | 0 | 3 | H | H | CH$_2$ | CH$_2$ | I |
| 624 | — | CO | CH$_2$ | 0 | 3 | Me | H | CH$_2$ | CH$_2$ | I |
| 625 | — | CO | CH$_2$ | 0 | 3 | Et | H | CH$_2$ | CH$_2$ | I |
| 626 | — | CO | CH$_2$ | 0 | 3 | COCH$_3$ | H | CH$_2$ | CH$_2$ | I |
| 627 | — | CO | CH$_2$ | 0 | 3 | COC$_6$H$_5$ | H | CH$_2$ | CH$_2$ | I |
| 628 | — | CO | CH$_2$ | 0 | 3 | Br | H | CH$_2$ | CH$_2$ | I |
| 629 | CO | — | CH$_2$ | 0 | 3 | H | H | CO | (CH$_2$)$_3$ | I |
| 630 | CO | — | CH$_2$ | 0 | 3 | Me | H | CO | (CH$_2$)$_3$ | I |
| 631 | CO | — | CH$_2$ | 0 | 3 | Et | H | CO | (CH$_2$)$_3$ | I |
| 632 | CO | — | CH$_2$ | 0 | 3 | COCH$_3$ | H | CO | (CH$_2$)$_3$ | I |
| 633 | CO | — | CH$_2$ | 0 | 3 | COC$_6$H$_5$ | H | CO | (CH$_2$)$_3$ | I |
| 634 | CO | — | CH$_2$ | 0 | 3 | Br | H | CO | (CH$_2$)$_3$ | I |
| 635 | CO | — | CH$_2$ | 0 | 3 | H | H | CH$_2$ | CH$_2$ | I |
| 636 | CO | — | CH$_2$ | 0 | 3 | Me | H | CH$_2$ | CH$_2$ | I |
| 637 | CO | — | CH$_2$ | 0 | 3 | Et | H | CH$_2$ | CH$_2$ | I |
| 638 | CO | — | CH$_2$ | 0 | 3 | COCH$_3$ | H | CH$_2$ | CH$_2$ | I |
| 639 | CO | — | CH$_2$ | 0 | 3 | COC$_6$H$_5$ | H | CH$_2$ | CH$_2$ | I |
| 640 | CO | — | CH$_2$ | 0 | 3 | Br | H | CH$_2$ | CH$_2$ | I |

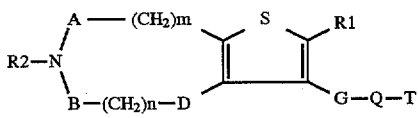

| | | | | | | | | | | |
|---|---|---|---|---|---|---|---|---|---|---|
| 713 | — | CO | CH$_2$ | 0 | 1 | H | H | CO | (CH$_2$)$_3$ | I |
| 714 | — | CO | CH$_2$ | 0 | 1 | Me | H | CO | (CH$_2$)$_3$ | I |
| 715 | — | CO | CH$_2$ | 0 | 1 | Et | H | CO | (CH$_2$)$_3$ | I |
| 716 | — | CO | CH$_2$ | 0 | 1 | COCH$_3$ | H | CO | (CH$_2$)$_3$ | I |
| 717 | — | CO | CH$_2$ | 0 | 1 | COC$_6$H$_5$ | H | CO | (CH$_2$)$_3$ | I |
| 718 | — | CO | CH$_2$ | 0 | 1 | Br | H | CO | (CH$_2$)$_3$ | I |
| 719 | — | CO | CH$_2$ | 0 | 1 | H | H | CH$_2$ | CH$_2$ | I |
| 720 | — | CO | CH$_2$ | 0 | 1 | Me | H | CH$_2$ | CH$_2$ | I |
| 721 | — | CO | CH$_2$ | 0 | 1 | Et | H | CH$_2$ | CH$_2$ | I |
| 722 | — | CO | CH$_2$ | 0 | 1 | COCH$_3$ | H | CH$_2$ | CH$_2$ | I |
| 723 | — | CO | CH$_2$ | 0 | 1 | COC$_6$H$_5$ | H | CH$_2$ | CH$_2$ | I |
| 724 | — | CO | CH$_2$ | 0 | 1 | Br | H | CH$_2$ | CH$_2$ | I |
| 725 | CO | — | CH$_2$ | 0 | 1 | H | H | CO | (CH$_2$)$_3$ | I |
| 726 | CO | — | CH$_2$ | 0 | 1 | Me | H | CO | (CH$_2$)$_3$ | I |
| 727 | CO | — | CH$_2$ | 0 | 1 | Et | H | CO | (CH$_2$)$_3$ | I |
| 728 | CO | — | CH$_2$ | 0 | 1 | COCH$_3$ | H | CO | (CH$_2$)$_3$ | I |
| 729 | CO | — | CH$_2$ | 0 | 1 | COC$_6$H$_5$ | H | CO | (CH$_2$)$_3$ | I |
| 730 | CO | — | CH$_2$ | 0 | 1 | Br | H | CO | (CH$_2$)$_3$ | I |
| 731 | CO | — | CH$_2$ | 0 | 1 | H | H | CH$_2$ | CH$_2$ | I |
| 732 | CO | — | CH$_2$ | 0 | 1 | Me | H | CH$_2$ | CH$_2$ | I |
| 733 | CO | — | CH$_2$ | 0 | 1 | Et | H | CH$_2$ | CH$_2$ | I |

-continued

| | | | | | | | | | | |
|---|---|---|---|---|---|---|---|---|---|---|
| 734 | CO | — | CH₂ | 0 | 1 | COCH₃ | H | CH₂ | CH₂ | I |
| 735 | CO | — | CH₂ | 0 | 1 | COC₆H₅ | H | CH₂ | CH₂ | I |
| 736 | CO | — | CH₂ | 0 | 1 | Br | H | CH₂ | CH₂ | I |
| 737 | — | CO | CH₂ | 0 | 2 | H | H | CO | (CH₂)₃ | I |
| 738 | — | CO | CH₂ | 0 | 2 | Me | H | CO | (CH₂)₃ | I |
| 739 | — | CO | CH₂ | 0 | 2 | Et | H | CO | (CH₂)₃ | I |
| 740 | — | CO | CH₂ | 0 | 2 | COCH₃ | H | CO | (CH₂)₃ | I |
| 741 | — | CO | CH₂ | 0 | 2 | COC₆H₅ | H | CO | (CH₂)₃ | I |
| 742 | — | CO | CH₂ | 0 | 2 | Br | H | CO | (CH₂)₃ | I |
| 743 | — | CO | CH₂ | 0 | 2 | H | H | CH₂ | CH₂ | I |
| 744 | — | CO | CH₂ | 0 | 2 | Me | H | CH₂ | CH₂ | I |
| 745 | — | CO | CH₂ | 0 | 2 | Et | H | CH₂ | CH₂ | I |
| 746 | — | CO | CH₂ | 0 | 2 | COCH₃ | H | CH₂ | CH₂ | I |
| 747 | — | CO | CH₂ | 0 | 2 | COC₆H₅ | H | CH₂ | CH₂ | I |
| 748 | — | CO | CH₂ | 0 | 2 | Br | H | CH₂ | CH₂ | I |
| 749 | CO | — | CH₂ | 0 | 2 | H | H | CO | (CH₂)₃ | I |
| 750 | CO | — | CH₂ | 0 | 2 | Me | H | CO | (CH₂)₃ | I |
| 751 | CO | — | CH₂ | 0 | 2 | Et | H | CO | (CH₂)₃ | I |
| 752 | CO | — | CH₂ | 0 | 2 | COCH₃ | H | CO | (CH₂)₃ | I |
| 753 | CO | — | CH₂ | 0 | 2 | COC₆H₅ | H | CO | (CH₂)₃ | I |
| 754 | CO | — | CH₂ | 0 | 2 | Br | H | CO | (CH₂)₃ | I |
| 755 | CO | — | CH₂ | 0 | 2 | H | H | CH₂ | CH₂ | I |
| 756 | CO | — | CH₂ | 0 | 2 | Me | H | CH₂ | CH₂ | I |
| 757 | CO | — | CH₂ | 0 | 2 | Et | H | CH₂ | CH₂ | I |
| 758 | CO | — | CH₂ | 0 | 2 | COCH₃ | H | CH₂ | CH₂ | I |
| 759 | CO | — | CH₂ | 0 | 2 | COC₆H₅ | H | CH₂ | CH₂ | I |
| 760 | CO | — | CH₂ | 0 | 2 | Br | H | CH₂ | CH₂ | I |
| 761 | — | CO | CH₂ | 0 | 3 | H | H | CO | (CH₂)₃ | I |
| 762 | — | CO | CH₂ | 0 | 3 | Me | H | CO | (CH₂)₃ | I |
| 763 | — | CO | CH₂ | 0 | 3 | Et | H | CO | (CH₂)₃ | I |
| 764 | — | CO | CH₂ | 0 | 3 | COCH₃ | H | CO | (CH₂)₃ | I |
| 765 | — | CO | CH₂ | 0 | 3 | COC₆H₅ | H | CO | (CH₂)₃ | I |
| 766 | — | CO | CH₂ | 0 | 3 | Br | H | CO | (CH₂)₃ | I |
| 767 | — | CO | CH₂ | 0 | 3 | H | H | CH₂ | CH₂ | I |
| 768 | — | CO | CH₂ | 0 | 3 | Me | H | CH₂ | CH₂ | I |
| 769 | — | CO | CH₂ | 0 | 3 | Et | H | CH₂ | CH₂ | I |
| 770 | — | CO | CH₂ | 0 | 3 | COCH₃ | H | CH₂ | CH₂ | I |
| 771 | — | CO | CH₂ | 0 | 3 | COC₆H₅ | H | CH₂ | CH₂ | I |
| 772 | — | CO | CH₂ | 0 | 3 | Br | H | CH₂ | CH₂ | I |
| 773 | CO | — | CH₂ | 0 | 3 | H | H | CO | (CH₂)₃ | I |
| 774 | CO | — | CH₂ | 0 | 3 | Me | H | CO | (CH₂)₃ | I |
| 775 | CO | — | CH₂ | 0 | 3 | Et | H | CO | (CH₂)₃ | I |
| 776 | CO | — | CH₂ | 0 | 3 | COCH₃ | H | CO | (CH₂)₃ | I |
| 777 | CO | — | CH₂ | 0 | 3 | COC₆H₅ | H | CO | (CH₂)₃ | I |
| 778 | CO | — | CH₂ | 0 | 3 | Br | H | CO | (CH₂)₃ | I |
| 779 | CO | — | CH₂ | 0 | 3 | H | H | CH₂ | CH₂ | I |
| 780 | CO | — | CH₂ | 0 | 3 | Me | H | CH₂ | CH₂ | I |
| 781 | CO | — | CH₂ | 0 | 3 | Et | H | CH₂ | CH₂ | I |
| 782 | CO | — | CH₂ | 0 | 3 | COCH₃ | H | CH₂ | CH₂ | I |
| 783 | CO | — | CH₂ | 0 | 3 | COC₆H₅ | H | CH₂ | CH₂ | I |
| 784 | CO | — | CH₂ | 0 | 3 | Br | H | CH₂ | CH₂ | I |

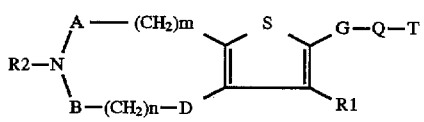

| | | | | | | | | | | |
|---|---|---|---|---|---|---|---|---|---|---|
| 785 | — | CO | CH₂ | 0 | 1 | H | H | CO | (CH₂)₃ | I |
| 786 | — | CO | CH₂ | 0 | 1 | Me | H | CO | (CH₂)₃ | I |
| 787 | — | CO | CH₂ | 0 | 1 | Et | H | CO | (CH₂)₃ | I |
| 788 | — | CO | CH₂ | 0 | 1 | COCH₃ | H | CO | (CH₂)₃ | I |
| 789 | — | CO | CH₂ | 0 | 1 | COC₆H₅ | H | CO | (CH₂)₃ | I |
| 790 | — | CO | CH₂ | 0 | 1 | Br | H | CO | (CH₂)₃ | I |
| 791 | — | CO | CH₂ | 0 | 1 | H | H | CH₂ | CH₂ | I |
| 792 | — | CO | CH₂ | 0 | 1 | Me | H | CH₂ | CH₂ | I |
| 793 | — | CO | CH₂ | 0 | 1 | Et | H | CH₂ | CH₂ | I |
| 794 | — | CO | CH₂ | 0 | 1 | COCH₃ | H | CH₂ | CH₂ | I |
| 795 | — | CO | CH₂ | 0 | 1 | COC₆H₅ | H | CH₂ | CH₂ | I |
| 796 | — | CO | CH₂ | 0 | 1 | Br | H | CH₂ | CH₂ | I |
| 797 | CO | — | CH₂ | 0 | 1 | H | H | CO | (CH₂)₃ | I |
| 798 | CO | — | CH₂ | 0 | 1 | Me | H | CO | (CH₂)₃ | I |
| 799 | CO | — | CH₂ | 0 | 1 | Et | H | CO | (CH₂)₃ | I |
| 800 | CO | — | CH₂ | 0 | 1 | COCH₃ | H | CO | (CH₂)₃ | I |
| 801 | CO | — | CH₂ | 0 | 1 | COC₆H₅ | H | CO | (CH₂)₃ | I |
| 802 | CO | — | CH₂ | 0 | 1 | Br | H | CO | (CH₂)₃ | I |
| 803 | CO | — | CH₂ | 0 | 1 | H | H | CH₂ | CH₂ | I |
| 804 | CO | — | CH₂ | 0 | 1 | Me | H | CH₂ | CH₂ | I |
| 805 | CO | — | CH₂ | 0 | 1 | Et | H | CH₂ | CH₂ | I |
| 806 | CO | — | CH₂ | 0 | 1 | COCH₃ | H | CH₂ | CH₂ | I |

| No. | A | B | D | m | n | R1 | R2 | G | Q | T |
|---|---|---|---|---|---|---|---|---|---|---|
| 807 | CO | — | CH$_2$ | 0 | 1 | COC$_6$H$_5$ | H | CH$_2$ | CH$_2$ | I |
| 808 | CO | — | CH$_2$ | 0 | 1 | Br | H | CH$_2$ | CH$_2$ | I |
| 809 | — | CO | CH$_2$ | 0 | 2 | H | H | CO | (CH$_2$)$_3$ | I |
| 810 | — | CO | CH$_2$ | 0 | 2 | Me | H | CO | (CH$_2$)$_3$ | I |
| 811 | — | CO | CH$_2$ | 0 | 2 | Et | H | CO | (CH$_2$)$_3$ | I |
| 812 | — | CO | CH$_2$ | 0 | 2 | COCH$_3$ | H | CO | (CH$_2$)$_3$ | I |
| 813 | — | CO | CH$_2$ | 0 | 2 | COC$_6$H$_5$ | H | CO | (CH$_2$)$_3$ | I |
| 814 | — | CO | CH$_2$ | 0 | 2 | Br | H | CO | (CH$_2$)$_3$ | I |
| 815 | — | CO | CH$_2$ | 0 | 2 | H | H | CH$_2$ | CH$_2$ | I |
| 816 | — | CO | CH$_2$ | 0 | 2 | Me | H | CH$_2$ | CH$_2$ | I |
| 817 | — | CO | CH$_2$ | 0 | 2 | Et | H | CH$_2$ | CH$_2$ | I |
| 618 | — | CO | CH$_2$ | 0 | 2 | COCH$_3$ | H | CH$_2$ | CH$_2$ | I |
| 819 | — | CO | CH$_2$ | 0 | 2 | COC$_6$H$_5$ | H | CH$_2$ | CH$_2$ | I |
| 820 | — | CO | CH$_2$ | 0 | 2 | Br | H | CH$_2$ | CH$_2$ | I |
| 821 | CO | — | CH$_2$ | 0 | 2 | H | H | CO | (CH$_2$)$_3$ | I |
| 822 | CO | — | CH$_2$ | 0 | 2 | Me | H | Co | (CH$_2$)$_3$ | I |
| 823 | CO | — | CH$_2$ | 0 | 2 | Et | H | CO | (CH$_2$)$_3$ | I |
| 824 | CO | — | CH$_2$ | 0 | 2 | COCH$_3$ | H | CO | (CH$_2$)$_3$ | I |
| 825 | CO | — | CH$_2$ | 0 | 2 | COC$_6$H$_5$ | H | CO | (CH$_2$)$_3$ | I |
| 826 | CO | — | CH$_2$ | 0 | 2 | Br | H | CO | (CH$_2$)$_3$ | I |
| 827 | CO | — | CH$_2$ | 0 | 2 | H | H | CH$_2$ | CH$_2$ | I |
| 828 | CO | — | CH$_2$ | 0 | 2 | Me | H | CH$_2$ | CH$_2$ | I |
| 829 | CO | — | CH$_2$ | 0 | 2 | Et | H | CH$_2$ | CH$_2$ | I |
| 830 | CO | — | CH$_2$ | 0 | 2 | COCH$_3$ | H | CH$_2$ | CH$_2$ | I |
| 831 | CO | — | CH$_2$ | 0 | 2 | COC$_6$H$_5$ | H | CH$_2$ | CH$_2$ | I |
| 832 | CO | — | CH$_2$ | 0 | 2 | Br | H | CH$_2$ | CH$_2$ | I |
| 833 | — | CO | CH$_2$ | 0 | 3 | H | H | CO | (CH$_2$)$_3$ | I |
| 834 | — | CO | CH$_2$ | 0 | 3 | Me | H | CO | (CH$_2$)$_3$ | I |
| 835 | — | CO | CH$_2$ | 0 | 3 | Et | H | CO | (CH$_2$)$_3$ | I |
| 836 | — | CO | CH$_2$ | 0 | 3 | COCH$_3$ | H | CO | (CH$_2$)$_3$ | I |
| 837 | — | CO | CH$_2$ | 0 | 3 | COC$_6$H$_5$ | H | CO | (CH$_2$)$_3$ | I |
| 838 | — | CO | CH$_2$ | 0 | 3 | Br | H | CO | (CH$_2$)$_3$ | I |
| 839 | — | CO | CH$_2$ | 0 | 3 | H | H | CH$_2$ | CH$_2$ | I |
| 840 | — | CO | CH$_2$ | 0 | 3 | Me | H | CH$_2$ | CH$_2$ | I |
| 841 | — | CO | CH$_2$ | 0 | 3 | Et | H | CH$_2$ | CH$_2$ | I |
| 842 | — | CO | CH$_2$ | 0 | 3 | COCH$_3$ | H | CH$_2$ | CH$_2$ | I |
| 843 | — | CO | CH$_2$ | 0 | 3 | COC$_6$H$_5$ | H | CH$_2$ | CH$_2$ | I |
| 844 | — | CO | CH$_2$ | 0 | 3 | Br | H | CH$_2$ | CH$_2$ | I |
| 845 | CO | — | CH$_2$ | 0 | 3 | H | H | CO | (CH$_2$)$_3$ | I |
| 846 | CO | — | CH$_2$ | 0 | 3 | Me | H | CO | (CH$_2$)$_3$ | I |
| 847 | CO | — | CH$_2$ | 0 | 3 | Et | H | CO | (CH$_2$)$_3$ | I |
| 848 | CO | — | CH$_2$ | 0 | 3 | COCH$_3$ | H | CO | (CH$_2$)$_3$ | I |
| 849 | CO | — | CH$_2$ | 0 | 3 | COC$_6$H$_5$ | H | CO | (CH$_2$)$_3$ | I |
| 850 | CO | — | CH$_2$ | 0 | 3 | Br | H | CO | (CH$_2$)$_3$ | I |
| 851 | CO | — | CH$_2$ | 0 | 3 | H | H | CH$_2$ | CH$_2$ | I |
| 852 | CO | — | CH$_2$ | 0 | 3 | Me | H | CH$_2$ | CH$_2$ | I |
| 853 | CO | — | CH$_2$ | 0 | 3 | Et | H | CH$_2$ | CH$_2$ | I |
| 854 | CO | — | CH$_2$ | 0 | 3 | COCH$_3$ | H | CH$_2$ | CH$_2$ | I |
| 855 | CO | — | CH$_2$ | 0 | 3 | COC$_6$H$_5$ | H | CH$_2$ | CH$_2$ | I |
| 856 | CO | — | CH$_2$ | 0 | 3 | Br | H | CH$_2$ | CH$_2$ | I |

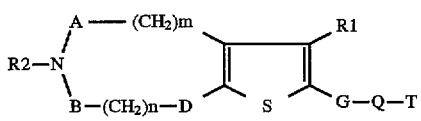

| No. | A | B | D | m | n | R1 | R2 | G | Q | T |
|---|---|---|---|---|---|---|---|---|---|---|
| 857 | — | — | CH$_2$ | 0 | 2 | H | CH$_3$CO | CO | (CH$_2$)$_3$ | I |
| 858 | — | — | CH$_2$ | 0 | 2 | Me | CH$_3$CO | CO | (CH$_2$)$_3$ | I |
| 859 | — | — | CH$_2$ | 0 | 2 | Et | CH$_3$CO | CO | (CH$_2$)$_3$ | I |
| 860 | — | — | CH$_2$ | 0 | 2 | COCH$_3$ | CH$_3$CO | CO | (CH$_2$)$_3$ | I |
| 861 | — | — | CH$_2$ | 0 | 2 | COC$_6$H$_5$ | CH$_3$CO | CO | (CH$_2$)$_3$ | I |
| 862 | — | — | CH$_2$ | 0 | 2 | H | H | CO | (CH$_2$)$_3$ | I |
| 863 | — | — | CH$_2$ | 0 | 2 | H | Me | CO | (CH$_2$)$_3$ | I |
| 864 | — | — | CH$_2$ | 0 | 2 | H | C$_6$H$_5$CO | CO | (CH$_2$)$_3$ | I |
| 865 | — | — | CH$_2$ | 0 | 2 | H | CH$_3$CO | CH$_2$ | CH$_2$ | I |
| 866 | — | — | CH$_2$ | 0 | 2 | Me | CH$_3$CO | CH$_2$ | CH$_2$ | I |
| 867 | — | — | CH$_2$ | 0 | 2 | Et | CH$_3$CO | CH$_2$ | CH$_2$ | I |
| 868 | — | — | CH$_2$ | 0 | 2 | COCH$_3$ | CH$_3$CO | CH$_2$ | CH$_2$ | I |
| 869 | — | — | CH$_2$ | 0 | 2 | COC$_6$H$_5$ | CH$_3$CO | CH$_2$ | CH$_2$ | I |
| 870 | — | — | CH$_2$ | 0 | 2 | H | H | CH$_2$ | CH$_2$ | I |
| 671 | — | — | CH$_2$ | 0 | 2 | H | Me | CH$_2$ | CH$_2$ | I |
| 872 | — | — | CH$_2$ | 0 | 2 | H | C$_6$H$_5$CO | CH$_2$ | CH$_2$ | I |
| 873 | — | — | CH$_2$ | 1 | 1 | H | CH$_3$CO | CO | (CH$_2$)$_3$ | I |
| 874 | — | — | CH$_2$ | 1 | 1 | Me | CH$_3$CO | CO | (CH$_2$)$_3$ | I |
| 875 | — | — | CH$_2$ | 1 | 1 | Et | CH$_3$CO | CO | (CH$_2$)$_3$ | I |
| 876 | — | — | CH$_2$ | 1 | 1 | COCH$_3$ | CH$_3$CO | CO | (CH$_2$)$_3$ | I |
| 877 | — | — | CH$_2$ | 1 | 1 | COC$_6$H$_5$ | CH$_3$CO | CO | (CH$_2$)$_3$ | I |
| 878 | — | — | CH$_2$ | 1 | 1 | H | H | CO | (CH$_2$)$_3$ | I |
| 879 | — | — | CH$_2$ | 1 | 1 | H | Me | CO | (CH$_2$)$_3$ | I |

-continued

| | | | | | | | | | |
|---|---|---|---|---|---|---|---|---|---|
| 880 | — | — | CH$_2$ | 1 | 1 | H | C$_6$H$_5$CO | CO | (CH$_2$)$_3$ | I |
| 881 | — | — | CH$_2$ | 1 | 1 | H | CH$_3$CO | CH$_2$ | CH$_2$ | I |
| 882 | — | — | CH$_2$ | 1 | 1 | Me | CH$_3$CO | CH$_2$ | CH$_2$ | I |
| 883 | — | — | CH$_2$ | 1 | 1 | Et | CH$_3$CO | CH$_2$ | CH$_2$ | I |
| 884 | — | — | CH$_2$ | 1 | 1 | COCH$_3$ | CH$_3$CO | CH$_2$ | CH$_2$ | I |
| 885 | — | — | CH$_2$ | 1 | 1 | COC$_6$H$_5$ | CH$_3$CO | CH$_2$ | CH$_2$ | I |
| 886 | — | — | CH$_2$ | 1 | 1 | H | H | CH$_2$ | CH$_2$ | I |
| 887 | — | — | CH$_2$ | 1 | 1 | H | Me | CH$_2$ | CH$_2$ | I |
| 888 | — | — | CH$_2$ | 1 | 1 | H | C$_6$H$_5$CO | CH$_2$ | CH$_2$ | I |
| 889 | — | — | CH$_2$ | 2 | 0 | H | CH$_3$CO | CO | (CH$_2$)$_3$ | I |
| 890 | — | — | CH$_2$ | 2 | 0 | Me | CH$_3$CO | CO | (CH$_2$)$_3$ | I |
| 891 | — | — | CH$_2$ | 2 | 0 | Et | CH$_3$CO | CO | (CH$_2$)$_3$ | I |
| 892 | — | — | CH$_2$ | 2 | 0 | COCH$_3$ | CH$_3$CO | CO | (CH$_2$)$_3$ | I |
| 893 | — | — | CH$_2$ | 2 | 0 | COC$_6$H$_5$ | CH$_3$CO | CO | (CH$_2$)$_3$ | I |
| 894 | — | — | CH$_2$ | 2 | 0 | H | H | CO | (CH$_2$)$_3$ | I |
| 895 | — | — | CH$_2$ | 2 | 0 | H | Me | CO | (CH$_2$)$_3$ | I |
| 896 | — | — | CH$_2$ | 2 | 0 | H | C$_6$H$_5$CO | CO | (CH$_2$)$_3$ | I |
| 897 | — | — | CH$_2$ | 2 | 0 | H | CH$_3$CO | CH$_2$ | CH$_2$ | I |
| 898 | — | — | CH$_2$ | 2 | 0 | Me | CH$_3$CO | CH$_2$ | CH$_2$ | I |
| 899 | — | — | CH$_2$ | 2 | 0 | Et | CH$_3$CO | CH$_2$ | CH$_2$ | I |
| 900 | — | — | CH$_2$ | 2 | 0 | COCH$_3$ | CH$_3$CO | CH$_2$ | CH$_2$ | I |
| 901 | — | — | CH$_2$ | 2 | 0 | COC$_6$H$_5$ | CH$_3$CO | CH$_2$ | CH$_2$ | I |
| 902 | — | — | CH$_2$ | 2 | 0 | H | H | CH$_2$ | CH$_2$ | I |
| 903 | — | — | CH$_2$ | 2 | 0 | H | Me | CH$_2$ | CH$_2$ | I |
| 904 | — | — | CH$_2$ | 2 | 0 | H | C$_6$H$_5$CO | CH$_2$ | CH$_2$ | I |

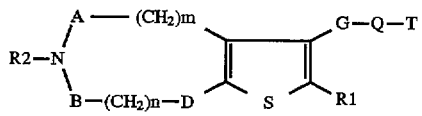

| | | | | | | | | | |
|---|---|---|---|---|---|---|---|---|---|
| 905 | — | — | CH$_2$ | 0 | 2 | H | CH$_3$CO | CO | (CH$_2$)$_3$ | I |
| 906 | — | — | CH$_2$ | 0 | 2 | Me | CH$_3$CO | CO | (CH$_2$)$_3$ | I |
| 907 | — | — | CH$_2$ | 0 | 2 | Et | CH$_3$CO | CO | (CH$_2$)$_3$ | I |
| 908 | — | — | CH$_2$ | 0 | 2 | COCH$_3$ | CH$_3$CO | CO | (CH$_2$)$_3$ | I |
| 909 | — | — | CH$_2$ | 0 | 2 | COC$_6$H$_5$ | CH$_3$CO | CO | (CH$_2$)$_3$ | I |
| 910 | — | — | CH$_2$ | 0 | 2 | H | H | CO | (CH$_2$)$_3$ | I |
| 911 | — | — | CH$_2$ | 0 | 2 | H | Me | CO | (CH$_2$)$_3$ | I |
| 912 | — | — | CH$_2$ | 0 | 2 | H | C$_6$H$_5$CO | CO | (CH$_2$)$_3$ | I |
| 913 | — | — | CH$_2$ | 0 | 2 | H | CH$_3$CO | CH$_2$ | CH$_2$ | I |
| 914 | — | — | CH$_2$ | 0 | 2 | Me | CH$_3$CO | CH$_2$ | CH$_2$ | I |
| 915 | — | — | CH$_2$ | 0 | 2 | Et | CH$_3$CO | CH$_2$ | CH$_2$ | I |
| 916 | — | — | CH$_2$ | 0 | 2 | COCH$_3$ | CH$_3$CO | CH$_2$ | CH$_2$ | I |
| 917 | — | — | CH$_2$ | 0 | 2 | COC$_6$H$_5$ | CH$_3$CO | CH$_2$ | CH$_2$ | I |
| 918 | — | — | CH$_2$ | 0 | 2 | H | H | CH$_2$ | CH$_2$ | I |
| 919 | — | — | CH$_2$ | 0 | 2 | H | Me | CH$_2$ | CH$_2$ | I |
| 920 | — | — | CH$_2$ | 0 | 2 | H | C$_6$H$_5$CO | CH$_2$ | CH$_2$ | I |
| 921 | — | — | CH$_2$ | 1 | 1 | H | CH$_3$CO | CO | (CH$_2$)$_3$ | I |
| 922 | — | — | CH$_2$ | 1 | 1 | Me | CH$_3$CO | CO | (CH$_2$)$_3$ | I |
| 923 | — | — | CH$_2$ | 1 | 1 | Et | CH$_3$CO | CO | (CH$_2$)$_3$ | I |
| 924 | — | — | CH$_2$ | 1 | 1 | COCH$_3$ | CH$_3$CO | CO | (CH$_2$)$_3$ | I |
| 925 | — | — | CH$_2$ | 1 | 1 | COC$_6$H$_5$ | CH$_3$CO | CO | (CH$_2$)$_3$ | I |
| 926 | — | — | CH$_2$ | 1 | 1 | H | H | CO | (CH$_2$)$_3$ | I |
| 927 | — | — | CH$_2$ | 1 | 1 | H | Me | CO | (CH$_2$)$_3$ | I |
| 928 | — | — | CH$_2$ | 1 | 1 | H | C$_6$H$_5$CO | CO | (CH$_2$)$_3$ | I |
| 929 | — | — | CH$_2$ | 1 | 1 | H | CH$_3$CO | CH$_2$ | CH$_2$ | I |
| 930 | — | — | CH$_2$ | 1 | 1 | Me | CH$_3$CO | CH$_2$ | CH$_2$ | I |
| 931 | — | — | CH$_2$ | 1 | 1 | Et | CH$_3$CO | CH$_2$ | CH$_2$ | I |
| 932 | — | — | CH$_2$ | 1 | 1 | COCH$_3$ | CH$_3$CO | CH$_2$ | CH$_2$ | I |
| 933 | — | — | CH$_2$ | 1 | 1 | COC$_6$H$_5$ | CH$_3$CO | CH$_2$ | CH$_2$ | I |
| 934 | — | — | CH$_2$ | 1 | 1 | H | H | CH$_2$ | CH$_2$ | I |
| 935 | — | — | CH$_2$ | 1 | 1 | H | He | CH$_2$ | CH$_2$ | I |
| 936 | — | — | CH$_2$ | 1 | 1 | H | C$_6$H$_5$CO | CH$_2$ | CH$_2$ | I |
| 937 | — | — | CH$_2$ | 2 | 0 | H | CH$_3$CO | CO | (CH$_2$)$_3$ | I |
| 938 | — | — | CH$_2$ | 2 | 0 | Me | CH$_3$CO | CO | (CH$_2$)$_3$ | I |
| 939 | — | — | CH$_2$ | 2 | 0 | Et | CH$_3$CO | CO | (CH$_2$)$_3$ | I |
| 940 | — | — | CH$_2$ | 2 | 0 | COCH$_3$ | CH$_3$CO | CO | (CH$_2$)$_3$ | I |
| 941 | — | — | CH$_2$ | 2 | 0 | COC$_6$H$_5$ | CH$_3$CO | CO | (CH$_2$)$_3$ | I |
| 942 | — | — | CH$_2$ | 2 | 0 | H | H | CO | (CH$_2$)$_3$ | I |
| 943 | — | — | CH$_2$ | 2 | 0 | H | Me | CO | (CH$_2$)$_3$ | I |
| 944 | — | — | CH$_2$ | 2 | 0 | H | C$_6$H$_5$CO | CO | (CH$_2$)$_3$ | I |
| 945 | — | — | CH$_2$ | 2 | 0 | H | CH$_3$CO | CH$_2$ | CH$_2$ | I |
| 946 | — | — | CH$_2$ | 2 | 0 | Me | CH$_3$CO | CH$_2$ | CH$_2$ | I |
| 947 | — | — | CH$_2$ | 2 | 0 | Et | CH$_3$CO | CH$_2$ | CH$_2$ | I |
| 948 | — | — | CH$_2$ | 2 | 0 | COCH$_3$ | CH$_3$CO | CH$_2$ | CH$_2$ | I |
| 949 | — | — | CH$_2$ | 2 | 0 | COC$_6$H$_5$ | CH$_3$CO | CH$_2$ | CH$_2$ | I |
| 950 | — | — | CH$_2$ | 2 | 0 | H | H | CH$_2$ | CH$_2$ | I |
| 951 | — | — | CH$_2$ | 2 | 0 | H | Me | CH$_2$ | CH$_2$ | I |
| 952 | — | — | CH$_2$ | 2 | 0 | H | C$_6$H$_5$CO | CH$_2$ | CH$_2$ | I |

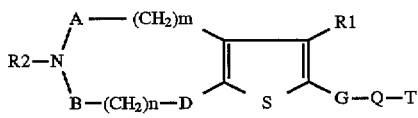

| | | | | | R1 | | G—Q—T | | |
|---|---|---|---|---|---|---|---|---|---|
| 953 | — | — | CH₂ | 0 | 3 | H | CH₃CO | CO | (CH₂)₃ | I |
| 954 | — | — | CH₂ | 0 | 3 | Me | CH₃CO | CO | (CH₂)₃ | I |
| 955 | — | — | CH₂ | 0 | 3 | Et | CH₃CO | CO | (CH₂)₃ | I |
| 956 | — | — | CH₂ | 0 | 3 | COCH₃ | CH₃CO | CO | (CH₂)₃ | I |
| 957 | — | — | CH₂ | 0 | 3 | COC₆H₅ | CH₃CO | CO | (CH₂)₃ | I |
| 958 | — | — | CH₂ | 0 | 3 | H | H | CO | (CH₂)₃ | I |
| 959 | — | — | CH₂ | 0 | 3 | H | Me | CO | (CH₂)₃ | I |
| 960 | — | — | CH₂ | 0 | 3 | H | C₆H₅CO | CO | (CH₂)₃ | I |
| 961 | — | — | CH₂ | 0 | 3 | H | CH₃CO | CH₂ | CH₂ | I |
| 962 | — | — | CH₂ | 0 | 3 | Me | CH₃CO | CH₂ | CH₂ | I |
| 963 | — | — | CH₂ | 0 | 3 | Et | CH₃CO | CH₂ | CH₂ | I |
| 964 | — | — | CH₂ | 0 | 3 | COCH₃ | CH₃CO | CH₂ | CH₂ | I |
| 965 | — | — | CH₂ | 0 | 3 | COC₆H₅ | CH₃CO | CH₂ | CH₂ | I |
| 966 | — | — | CH₂ | 0 | 3 | H | H | CH₂ | CH₂ | I |
| 967 | — | — | CH₂ | 0 | 3 | H | Me | CH₂ | CH₂ | I |
| 968 | — | — | CH₂ | 0 | 3 | H | C₆H₅CO | CH₂ | CH₂ | I |
| 969 | — | — | CH₂ | 1 | 2 | H | CH₃CO | CO | (CH₂)₃ | I |
| 970 | — | — | CH₂ | 1 | 2 | Me | CH₃CO | CO | (CH₂)₃ | I |
| 971 | — | — | CH₂ | 1 | 2 | Et | CH₃CO | CO | (CH₂)₃ | I |
| 972 | — | — | CH₂ | 1 | 2 | COCH₃ | CH₃CO | CO | (CH₂)₃ | I |
| 973 | — | — | CH₂ | 1 | 2 | COC₆H₅ | CH₃CO | CO | (CH₂)₃ | I |
| 974 | — | — | CH₂ | 1 | 2 | H | H | CO | (CH₂)₃ | I |
| 975 | — | — | CH₂ | 1 | 2 | H | Me | CO | (CH₂)₃ | I |
| 976 | — | — | CH₂ | 1 | 2 | H | C₆H₅CO | CO | (CH₂)₃ | I |
| 977 | — | — | CH₂ | 1 | 2 | H | CH₃CO | CH₂ | CH₂ | I |
| 978 | — | — | CH₂ | 1 | 2 | Me | CH₃CO | CH₂ | CH₂ | I |
| 979 | — | — | CH₂ | 1 | 2 | Et | CH₃CO | CH₂ | CH₂ | I |
| 980 | — | — | CH₂ | 1 | 2 | COCH₃ | CH₃CO | CH₂ | CH₂ | I |
| 981 | — | — | CH₂ | 1 | 2 | COC₆H₅ | CH₃CO | CH₂ | CH₂ | I |
| 982 | — | — | CH₂ | 1 | 2 | H | H | CH₂ | CH₂ | I |
| 983 | — | — | CH₂ | 1 | 2 | H | Me | CH₂ | CH₂ | I |
| 984 | — | — | CH₂ | 1 | 2 | H | C₆H₅CO | CH₂ | CH₂ | I |
| 1001 | — | — | CH₂ | 3 | 0 | H | CH₃CO | CO | (CH₂)₃ | I |
| 1002 | — | — | CH₂ | 3 | 0 | Me | CH₃CO | CO | (CH₂)₃ | I |
| 1003 | — | — | CH₂ | 3 | 0 | Et | CH₃CO | CO | (CH₂)₃ | I |
| 1004 | — | — | CH₂ | 3 | 0 | COCH₃ | CH₃CO | CO | (CH₂)₃ | I |
| 1005 | — | — | CH₂ | 3 | 0 | COC₆H₅ | CH₃CO | CO | (CH₂)₃ | I |
| 1006 | — | — | CH₂ | 3 | 0 | H | H | CO | (CH₂)₃ | I |
| 1007 | — | — | CH₂ | 3 | 0 | H | Me | CO | (CH₂)₃ | I |
| 1008 | — | — | CH₂ | 3 | 0 | H | C₆H₅CO | CO | (CH₂)₃ | I |
| 1009 | — | — | CH₂ | 3 | 0 | H | CH₃CO | CH₂ | CH₂ | I |
| 1010 | — | — | CH₂ | 3 | 0 | Me | CH₃CO | CH₂ | CH₂ | I |
| 1011 | — | — | CH₂ | 3 | 0 | Et | CH₃CO | CH₂ | CH₂ | I |
| 1012 | — | — | CH₂ | 3 | 0 | COCH₃ | CH₃CO | CH₂ | CH₂ | I |
| 1013 | — | — | CH₂ | 3 | 0 | COC₆H₅ | CH₃CO | CH₂ | CH₂ | I |
| 1014 | — | — | CH₂ | 3 | 0 | H | H | CH₂ | CH₂ | I |
| 1015 | — | — | CH₂ | 3 | 0 | H | Me | CH₂ | CH₂ | I |
| 1016 | — | — | CH₂ | 3 | 0 | H | C₆H₅CO | CH₂ | CH₂ | I |

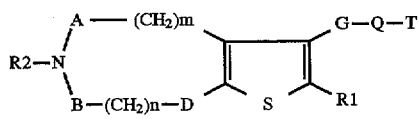

| 1017 | — | — | CH₂ | 0 | 3 | H | CH₃CO | CO | (CH₂)₃ | I |
|---|---|---|---|---|---|---|---|---|---|---|
| 1018 | — | — | CH₂ | 0 | 3 | Me | CH₃CO | CO | (CH₂)₃ | I |
| 1019 | — | — | CH₂ | 0 | 3 | Et | CH₃CO | CO | (CH₂)₃ | I |
| 1020 | — | — | CH₂ | 0 | 3 | COCH₃ | CH₃CO | CO | (CH₂)₃ | I |
| 1021 | — | — | CH₂ | 0 | 3 | COC₆H₅ | CH₃CO | CO | (CH₂)₃ | I |
| 1022 | — | — | CH₂ | 0 | 3 | H | H | CO | (CH₂)₃ | I |
| 1023 | — | — | CH₂ | 0 | 3 | H | Me | CO | (CH₂)₃ | I |
| 1024 | — | — | CH₂ | 0 | 3 | H | C₆H₅CO | CO | (CH₂)₃ | I |
| 1025 | — | — | CH₂ | 0 | 3 | H | CH₃CO | CH₂ | CH₂ | I |
| 1026 | — | — | CH₂ | 0 | 3 | Me | CH₃CO | CH₂ | CH₂ | I |
| 1027 | — | — | CH₂ | 0 | 3 | Et | CH₃CO | CH₂ | CH₂ | I |
| 1028 | — | — | CH₂ | 0 | 3 | COCH₃ | CH₃CO | CH₂ | CH₂ | I |
| 1029 | — | — | CH₂ | 0 | 3 | COC₆H₅ | CH₃CO | CH₂ | CH₂ | I |
| 1030 | — | — | CH₂ | 0 | 3 | H | H | CH₂ | CH₂ | I |
| 1031 | — | — | CH₂ | 0 | 3 | H | Me | CH₂ | CH₂ | I |
| 1032 | — | — | CH₂ | 0 | 3 | H | C₆H₅CO | CH₂ | CH₂ | I |
| 1033 | — | — | CH₂ | 1 | 2 | H | CH₃CO | CO | (CH₂)₃ | I |
| 1034 | — | — | CH₂ | 1 | 2 | Me | CH₃CO | CO | (CH₂)₃ | I |

-continued

| | | | | | | | | | |
|---|---|---|---|---|---|---|---|---|---|
| 1035 | — | — | CH₂ | 1 | 2 | Et | CH₃CO | CO | (CH₂)₃ | I |
| 1036 | — | — | CH₂ | 1 | 2 | COCH₃ | CH₃CO | CO | (CH₂)₃ | I |
| 1037 | — | — | CH₂ | 1 | 2 | COC₆H₅ | CH₃CO | CO | (CH₂)₃ | I |
| 1038 | — | — | CH₂ | 1 | 2 | H | H | CO | (CH₂)₃ | I |
| 1039 | — | — | CH₂ | 1 | 2 | H | Me | CO | (CH₂)₃ | I |
| 1040 | — | — | CH₂ | 1 | 2 | H | C₆H₅CO | CO | (CH₂)₃ | I |
| 1041 | — | — | CH₂ | 1 | 2 | H | CH₃CO | CH₂ | CH₂ | I |
| 1042 | — | — | CH₂ | 1 | 2 | Me | CH₃CO | CH₂ | CH₂ | I |
| 1043 | — | — | CH₂ | 1 | 2 | Et | CH₃CO | CH₂ | CH₂ | I |
| 1044 | — | — | CH₂ | 1 | 2 | COCH₃ | CH₃CO | CH₂ | CH₂ | I |
| 1045 | — | — | CH₂ | 1 | 2 | COC₆H₅ | CH₃CO | CH₂ | CH₂ | I |
| 1046 | — | — | CH₂ | 1 | 2 | H | H | CH₂ | CH₂ | I |
| 1047 | — | — | CH₂ | 1 | 2 | H | Me | CH₂ | CH₂ | I |
| 1048 | — | — | CH₂ | 1 | 2 | H | C₆H₅CO | CH₂ | CH₂ | I |
| 1065 | — | — | CH₂ | 3 | 0 | H | CH₃CO | CO | (CH₂)₃ | I |
| 1066 | — | — | CH₂ | 3 | 0 | Me | CH₃CO | CO | (CH₂)₃ | I |
| 1067 | — | — | CH₂ | 3 | 0 | Et | CH₃CO | CO | (CH₂)₃ | I |
| 1068 | — | — | CH₂ | 3 | 0 | COCH₃ | CH₃CO | CO | (CH₂)₃ | I |
| 1069 | — | — | CH₂ | 3 | 0 | COC₆H₅ | CH₃CO | CO | (CH₂)₃ | I |
| 1070 | — | — | CH₂ | 3 | 0 | H | H | CO | (CH₂)₃ | I |
| 1071 | — | — | CH₂ | 3 | 0 | H | Me | CO | (CH₂)₃ | I |
| 1072 | — | — | CH₂ | 3 | 0 | H | C₆H₅CO | CO | (CH₂)₃ | I |
| 1073 | — | — | CH₂ | 3 | 0 | H | CH₃CO | CH₂ | CH₂ | I |
| 1074 | — | — | CH₂ | 3 | 0 | Me | CH₃CO | CH₂ | CH₂ | I |
| 1075 | — | — | CH₂ | 3 | 0 | Et | CH₃CO | CH₂ | CH₂ | I |
| 1076 | — | — | CH₂ | 3 | 0 | COCH₃ | CH₃CO | CH₂ | CH₂ | I |
| 1077 | — | — | CH₂ | 3 | 0 | COC₆H₅ | CH₃CO | CH₂ | CH₂ | I |
| 1078 | — | — | CH₂ | 3 | 0 | H | H | CH₂ | CH₂ | I |
| 1079 | — | — | CH₂ | 3 | 0 | H | Me | CH₂ | CH₂ | I |
| 1080 | — | — | CH₂ | 3 | 0 | H | C₆H₅CO | CH₂ | CH₂ | I |

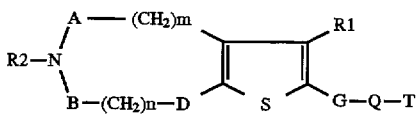

| | | | | | | | | | |
|---|---|---|---|---|---|---|---|---|---|
| 1081 | — | — | CH₂ | 0 | 4 | H | CH₃CO | CO | (CH₂)₃ | I |
| 1082 | — | — | CH₂ | 0 | 4 | Me | CH₃CO | CO | (CH₂)₃ | I |
| 1083 | — | — | CH₂ | 0 | 4 | Et | CH₃CO | CO | (CH₂)₃ | I |
| 1084 | — | — | CH₂ | 0 | 4 | COCH₃ | CH₃CO | CO | (CH₂)₃ | I |
| 1085 | — | — | CH₂ | 0 | 4 | COC₆H₅ | CH₃CO | CO | (CH₂)₃ | I |
| 1086 | — | — | CH₂ | 0 | 4 | H | H | CO | (CH₂)₃ | I |
| 1087 | — | — | CH₂ | 0 | 4 | H | Me | CO | (CH₂)₃ | I |
| 1088 | — | — | CH₂ | 0 | 4 | H | C₆H₅CO | CO | (CH₂)₃ | I |
| 1089 | — | — | CH₂ | 0 | 4 | H | CH₃CO | CH₂ | CH₂ | I |
| 1090 | — | — | CH₂ | 0 | 4 | Me | CH₃CO | CH₂ | CH₂ | I |
| 1091 | — | — | CH₂ | 0 | 4 | Et | CH₃CO | CH₂ | CH₂ | I |
| 1092 | — | — | CH₂ | 0 | 4 | COCH₃ | CH₃CO | CH₂ | CH₂ | I |
| 1093 | — | — | CH₂ | 0 | 4 | COC₆H₅ | CH₃CO | CH₂ | CH₂ | I |
| 1094 | — | — | CH₂ | 0 | 4 | H | H | CH₂ | CH₂ | I |
| 1095 | — | — | CH₂ | 0 | 4 | H | Me | CH₂ | CH₂ | I |
| 1096 | — | — | CH₂ | 0 | 4 | H | C₆H₅CO | CH₂ | CH₂ | I |
| 1097 | — | — | CH₂ | 1 | 3 | H | CH₃CO | CO | (CH₂)₃ | I |
| 1098 | — | — | CH₂ | 1 | 3 | Me | CH₃CO | CO | (CH₂)₃ | I |
| 1099 | — | — | CH₂ | 1 | 3 | Et | CH₃CO | CO | (CH₂)₃ | I |
| 1100 | — | — | CH₂ | 1 | 3 | COCH₃ | CH₃CO | CO | (CH₂)₃ | I |
| 1101 | — | — | CH₂ | 1 | 3 | COC₆H₅ | CH₃CO | CO | (CH₂)₃ | I |
| 1102 | — | — | CH₂ | 1 | 3 | H | H | CO | (CH₂)₃ | I |
| 1103 | — | — | CH₂ | 1 | 3 | H | Me | CO | (CH₂)₃ | I |
| 1104 | — | — | CH₂ | 1 | 3 | H | C₆H₅CO | CO | (CH₂)₃ | I |
| 1105 | — | — | CH₂ | 1 | 3 | H | CH₃CO | CH₂ | CH₂ | I |
| 1106 | — | — | CH₂ | 1 | 3 | Me | CH₃CO | CH₂ | CH₂ | I |
| 1107 | — | — | CH₂ | 1 | 3 | Et | CH₃CO | CH₂ | CH₂ | I |
| 1108 | — | — | CH₂ | 1 | 3 | COCH₃ | CH₃CO | CH₂ | CH₂ | I |
| 1109 | — | — | CH₂ | 1 | 3 | COC₆H₅ | CH₃CO | CH₂ | CH₂ | I |
| 1110 | — | — | CH₂ | 1 | 3 | H | H | CH₂ | CH₂ | I |
| 1111 | — | — | CH₂ | 1 | 3 | H | Me | CH₂ | CH₂ | I |
| 1112 | — | — | CH₂ | 1 | 3 | H | C₆H₅CO | CH₂ | CH₂ | I |
| 1145 | — | — | CH₂ | 4 | 0 | H | CH₃CO | CO | (CH₂)₃ | I |
| 1146 | — | — | CH₂ | 4 | 0 | Me | CH₃CO | CO | (CH₂)₃ | I |
| 1147 | — | — | CH₂ | 4 | 0 | Et | CH₃CO | CO | (CH₂)₃ | I |
| 1148 | — | — | CH₂ | 4 | 0 | COCH₃ | CH₃CO | CO | (CH₂)₃ | I |
| 1149 | — | — | CH₂ | 4 | 0 | COC₆H₅ | CH₃CO | CO | (CH₂)₃ | I |
| 1150 | — | — | CH₂ | 4 | 0 | H | H | CO | (CH₂)₃ | I |
| 1151 | — | — | CH₂ | 4 | 0 | H | Me | CO | (CH₂)₃ | I |
| 1152 | — | — | CH₂ | 4 | 0 | H | C₆H₅CO | CO | (CH₂)₃ | I |
| 1153 | — | — | CH₂ | 4 | 0 | H | CH₃CO | CH₂ | CH₂ | I |
| 1154 | — | — | CH₂ | 4 | 0 | Me | CH₃CO | CH₂ | CH₂ | I |
| 1155 | — | — | CH₂ | 4 | 0 | Et | CH₃CO | CH₂ | CH₂ | I |

-continued

| | | | | | | | | | | |
|---|---|---|---|---|---|---|---|---|---|---|
| 1156 | — | — | CH₂ | 4 | 0 | COCH₃ | CH₃CO | CH₂ | CH₂ | I |
| 1157 | — | — | CH₂ | 4 | 0 | COC₆H₅ | CH₃CO | CH₂ | CH₂ | I |
| 1158 | — | — | CH₂ | 4 | 0 | H | H | CH₂ | CH₂ | I |
| 1159 | — | — | CH₂ | 4 | 0 | H | Me | CH₂ | CH₂ | I |
| 1160 | — | — | CH₂ | 4 | 0 | H | C₆H₅CO | CH₂ | CH₂ | I |

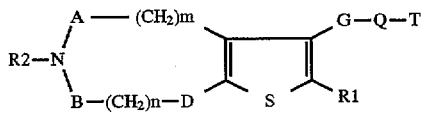

| | | | | | | | | | | |
|---|---|---|---|---|---|---|---|---|---|---|
| 1161 | — | — | CH₂ | 0 | 4 | H | CH₃CO | CO | (CH₂)₃ | I |
| 1162 | — | — | CH₂ | 0 | 4 | Me | CH₃CO | CO | (CH₂)₃ | I |
| 1163 | — | — | CH₂ | 0 | 4 | Et | CH₃CO | CO | (CH₂)₃ | I |
| 1164 | — | — | CH₂ | 0 | 4 | COCH₃ | CH₃CO | CO | (CH₂)₃ | I |
| 1165 | — | — | CH₂ | 0 | 4 | COC₆H₅ | CH₃CO | CO | (CH₂)₃ | I |
| 1166 | — | — | CH₂ | 0 | 4 | H | H | CO | (CH₂)₃ | I |
| 1167 | — | — | CH₂ | 0 | 4 | H | Me | CO | (CH₂)₃ | I |
| 1168 | — | — | CH₂ | 0 | 4 | H | C₆H₅CO | CO | (CH₂)₃ | I |
| 1169 | — | — | CH₂ | 0 | 4 | H | CH₃CO | CH₂ | CH₂ | I |
| 1170 | — | — | CH₂ | 0 | 4 | Me | CH₃CO | CH₂ | CH₂ | I |
| 1171 | — | — | CH₂ | 0 | 4 | Et | CH₃CO | CH₂ | CH₂ | I |
| 1172 | — | — | CH₂ | 0 | 4 | COCH₃ | CH₃CO | CH₂ | CH₂ | I |
| 1173 | — | — | CH₂ | 0 | 4 | COC₆H₅ | CH₃CO | CH₂ | CH₂ | I |
| 1174 | — | — | CH₂ | 0 | 4 | H | H | CH₂ | CH₂ | I |
| 1175 | — | — | CH₂ | 0 | 4 | H | Me | CH₂ | CH₂ | I |
| 1176 | — | — | CH₂ | 0 | 4 | H | C₆H₅CO | CH₂ | CH₂ | I |
| 1177 | — | — | CH₂ | 1 | 3 | H | CH₃CO | CO | (CH₂)₃ | I |
| 1178 | — | — | CH₂ | 1 | 3 | Me | CH₃CO | CO | (CH₂)₃ | I |
| 1179 | — | — | CH₂ | 1 | 3 | Et | CH₃CO | CO | (CH₂)₃ | I |
| 1180 | — | — | CH₂ | 1 | 3 | COCH₃ | CH₃CO | CO | (CH₂)₃ | I |
| 1181 | — | — | CH₂ | 1 | 3 | COC₆H₅ | CH₃CO | CO | (CH₂)₃ | I |
| 1182 | — | — | CH₂ | 1 | 3 | H | H | CO | (CH₂)₃ | I |
| 1183 | — | — | CH₂ | 1 | 3 | H | Me | CO | (CH₂)₃ | I |
| 1184 | — | — | CH₂ | 1 | 3 | H | C₆H₅CO | CO | (CH₂)₃ | I |
| 1185 | — | — | CH₂ | 1 | 3 | H | CH₃CO | CH₂ | CH₂ | I |
| 1186 | — | — | CH₂ | 1 | 3 | Me | CH₃CO | CH₂ | CH₂ | I |
| 1187 | — | — | CH₂ | 1 | 3 | Et | CH₃CO | CH₂ | CH₂ | I |
| 1188 | — | — | CH₂ | 1 | 3 | COCH₃ | CH₃CO | CH₂ | CH₂ | I |
| 1189 | — | — | CH₂ | 1 | 3 | COC₆H₅ | CH₃CO | CH₂ | CH₂ | I |
| 1190 | — | — | CH₂ | 1 | 3 | H | H | CH₂ | CH₂ | I |
| 1191 | — | — | CH₂ | 1 | 3 | H | Me | CH₂ | CH₂ | I |
| 1192 | — | — | CH₂ | 1 | 3 | H | C₆H₅CO | CH₂ | CH₂ | I |
| 1225 | — | — | CH₂ | 4 | 0 | H | CH₃CO | CO | (CH₂)₃ | I |
| 1226 | — | — | CH₂ | 4 | 0 | Me | CH₃CO | CO | (CH₂)₃ | I |
| 1227 | — | — | CH₂ | 4 | 0 | Et | CH₃CO | CO | (CH₂)₃ | I |
| 1228 | — | — | CH₂ | 4 | 0 | COCH₃ | CH₃CO | CO | (CH₂)₃ | I |
| 1229 | — | — | CH₂ | 4 | 0 | COC₆H₅ | CH₃CO | CO | (CH₂)₃ | I |
| 1230 | — | — | CH₂ | 4 | 0 | H | H | CO | (CH₂)₃ | I |
| 1231 | — | — | CH₂ | 4 | 0 | H | Me | CO | (CH₂)₃ | I |
| 1232 | — | — | CH₂ | 4 | 0 | H | C₆H₅CO | CO | (CH₂)₃ | I |
| 1233 | — | — | CH₂ | 4 | 0 | H | CH₃CO | CH₂ | CH₂ | I |
| 1234 | — | — | CH₂ | 4 | 0 | Me | CH₃CO | CH₂ | CH₂ | I |
| 1235 | — | — | CH₂ | 4 | 0 | Et | CH₃CO | CH₂ | CH₂ | I |
| 1236 | — | — | CH₂ | 4 | 0 | COCH₃ | CH₃CO | CH₂ | CH₂ | I |
| 1237 | — | — | CH₂ | 4 | 0 | COC₆H₅ | CH₃CO | CH₂ | CH₂ | I |
| 1238 | — | — | CH₂ | 4 | 0 | H | H | CH₂ | CH₂ | I |
| 1239 | — | — | CH₂ | 4 | 0 | H | Me | CH₂ | CH₂ | I |
| 1240 | — | — | CH₂ | 4 | 0 | H | C₆H₅CO | CH₂ | CH₂ | I |

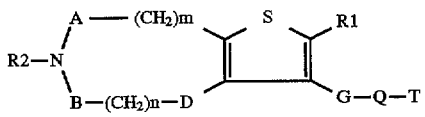

| | | | | | | | | | | |
|---|---|---|---|---|---|---|---|---|---|---|
| 1241 | — | — | CH₂ | 0 | 2 | H | CH₃CO | CO | (CH₂)₃ | I |
| 1242 | — | — | CH₂ | 0 | 2 | Me | CH₃CO | CO | (CH₂)₃ | I |
| 1243 | — | — | CH₂ | 0 | 2 | Et | CH₃CO | CO | (CH₂)₃ | I |
| 1244 | — | — | CH₂ | 0 | 2 | COCH₃ | CH₃CO | CO | (CH₂)₃ | I |
| 1245 | — | — | CH₂ | 0 | 2 | COC₆H₅ | CH₃CO | CO | (CH₂)₃ | I |
| 1246 | — | — | CH₂ | 0 | 2 | H | H | CO | (CH₂)₃ | I |
| 1247 | — | — | CH₂ | 0 | 2 | H | Me | CO | (CH₂)₃ | I |
| 1248 | — | — | CH₂ | 0 | 2 | H | C₆H₅CO | CO | (CH₂)₃ | I |
| 1249 | — | — | CH₂ | 0 | 2 | H | CH₃CO | CH₂ | CH₂ | I |
| 1250 | — | — | CH₂ | 0 | 2 | Me | CH₃CO | CH₂ | CH₂ | I |
| 1251 | — | — | CH₂ | 0 | 2 | Et | CH₃CO | CH₂ | CH₂ | I |
| 1252 | — | — | CH₂ | 0 | 2 | COCH₃ | CH₃CO | CH₂ | CH₂ | I |
| 1253 | — | — | CH₂ | 0 | 2 | COC₆H₅ | CH₃CO | CH₂ | CH₂ | I |

| | | | | | | | | | |
|---|---|---|---|---|---|---|---|---|---|
| 1254 | — | — | CH₂ | 0 | 2 | H | H | CH₂ | CH₂ | I |
| 1255 | — | — | CH₂ | 0 | 2 | H | Me | CH₂ | CH₂ | I |
| 1256 | — | — | CH₂ | 0 | 2 | H | C₆H₅CO | CH₂ | CH₂ | I |
| 1257 | — | — | CH₂ | 0 | 3 | H | CH₃CO | CO | (CH₂)₃ | I |
| 1258 | — | — | CH₂ | 0 | 3 | Me | CH₃CO | CO | (CH₂)₃ | I |
| 1259 | — | — | CH₂ | 0 | 3 | Et | CH₃CO | CO | (CH₂)₃ | I |
| 1260 | — | — | CH₂ | 0 | 3 | COCH₃ | CH₃CO | CO | (CH₂)₃ | I |
| 1261 | — | — | CH₂ | 0 | 3 | COC₆H₅ | CH₃CO | CO | (CH₂)₃ | I |
| 1262 | — | — | CH₂ | 0 | 3 | H | H | CO | (CH₂)₃ | I |
| 1263 | — | — | CH₂ | 0 | 3 | H | Me | CO | (CH₂)₃ | I |
| 1264 | — | — | CH₂ | 0 | 3 | H | C₆H₅CO | CO | (CH₂)₃ | I |
| 1265 | — | — | CH₂ | 0 | 3 | H | CH₃CO | CH₂ | CH₂ | I |
| 1266 | — | — | CH₂ | 0 | 3 | Me | CH₃CO | CH₂ | CH₂ | I |
| 1267 | — | — | CH₂ | 0 | 3 | Et | CH₃CO | CH₂ | CH₂ | I |
| 1268 | — | — | CH₂ | 0 | 3 | COCH₃ | CH₃CO | CH₂ | CH₂ | I |
| 1269 | — | — | CH₂ | 0 | 3 | COC₆H₅ | CH₃CO | CH₂ | CH₂ | I |
| 1270 | — | — | CH₂ | 0 | 3 | H | H | CH₂ | CH₂ | I |
| 1271 | — | — | CH₂ | 0 | 3 | H | Me | CH₂ | CH₂ | I |
| 1272 | — | — | CH₂ | 0 | 3 | H | C₆H₅CO | CH₂ | CH₂ | I |

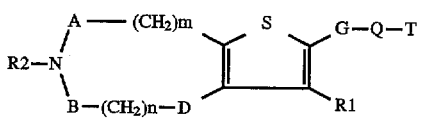

| | | | | | | | | | |
|---|---|---|---|---|---|---|---|---|---|
| 1289 | — | — | CH₂ | 0 | 2 | H | CH₃CO | CO | (CH₂)₃ | I |
| 1290 | — | — | CH₂ | 0 | 2 | Me | CH₃CO | CO | (CH₂)₃ | I |
| 1291 | — | — | CH₂ | 0 | 2 | Et | CH₃CO | CO | (CH₂)₃ | I |
| 1292 | — | — | CH₂ | 0 | 2 | COCH₃ | CH₃CO | CO | (CH₂)₃ | I |
| 1293 | — | — | CH₂ | 0 | 2 | COC₆H₅ | CH₃CO | CO | (CH₂)₃ | I |
| 1294 | — | — | CH₂ | 0 | 2 | H | H | CO | (CH₂)₃ | I |
| 1295 | — | — | CH₂ | 0 | 2 | H | Me | CO | (CH₂)₃ | I |
| 1296 | — | — | CH₂ | 0 | 2 | H | C₆H₅CO | CO | (CH₂)₃ | I |
| 1297 | — | — | CH₂ | 0 | 2 | H | CH₃CO | CH₂ | CH₂ | I |
| 1298 | — | — | CH₂ | 0 | 2 | Me | CH₃CO | CH₂ | CH₂ | I |
| 1299 | — | — | CH₂ | 0 | 2 | Et | CH₃CO | CH₂ | CH₂ | I |
| 1300 | — | — | CH₂ | 0 | 2 | COCH₃ | CH₃CO | CH₂ | CH₂ | I |
| 1301 | — | — | CH₂ | 0 | 2 | COC₆H₅ | CH₃CO | CH₂ | CH₂ | I |
| 1302 | — | — | CH₂ | 0 | 2 | H | H | CH₂ | CH₂ | I |
| 1303 | — | — | CH₂ | 0 | 2 | H | Me | CH₂ | CH₂ | I |
| 1304 | — | — | CH₂ | 0 | 2 | H | C₆H₅CO | CH₂ | CH₂ | I |
| 1305 | — | — | CH₂ | 0 | 3 | H | CH₃CO | CO | (CH₂)₃ | I |
| 1306 | — | — | CH₂ | 0 | 3 | Me | CH₃CO | CO | (CH₂)₃ | I |
| 1307 | — | — | CH₂ | 0 | 3 | Et | CH₃CO | CO | (CH₂)₃ | I |
| 1309 | — | — | CH₂ | 0 | 3 | COCH₃ | CH₃CO | CO | (CH₂)₃ | I |
| 1310 | — | — | CH₂ | 0 | 3 | COC₆H₅ | CH₃CO | CO | (CH₂)₃ | I |
| 1311 | — | — | CH₂ | 0 | 3 | H | H | CO | (CH₂)₃ | I |
| 1312 | — | — | CH₂ | 0 | 3 | H | Me | CO | (CH₂)₃ | I |
| 1313 | — | — | CH₂ | 0 | 3 | H | C₆H₅CO | CO | (CH₂)₃ | I |
| 1314 | — | — | CH₂ | 0 | 3 | H | CH₃CO | CH₂ | CH₂ | I |
| 1315 | — | — | CH₂ | 0 | 3 | Me | CH₃CO | CH₂ | CH₂ | I |
| 1316 | — | — | CH₂ | 0 | 3 | Et | CH₃CO | CH₂ | CH₂ | I |
| 1317 | — | — | CH₂ | 0 | 3 | COCH₃ | CH₃CO | CH₂ | CH₂ | I |
| 1318 | — | — | CH₂ | 0 | 3 | COC₆H₅ | CH₃CO | CH₂ | CH₂ | I |
| 1319 | — | — | CH₂ | 0 | 3 | H | H | CH₂ | CH₂ | I |
| 1320 | — | — | CH₂ | 0 | 3 | H | Me | CH₂ | CH₂ | I |
| 1321 | — | — | CH₂ | 0 | 3 | H | C₆H₅CO | CH₂ | CH₂ | I |
| 1322 | — | — | CH₂ | 0 | 4 | H | CH₃CO | CO | (CH₂)₃ | I |
| 1323 | — | — | CH₂ | 0 | 4 | Me | CH₃CO | CO | (CH₂)₃ | I |
| 1324 | — | — | CH₂ | 0 | 4 | Et | CH₃CO | CO | (CH₂)₃ | I |
| 1325 | — | — | CH₂ | 0 | 4 | COCH₃ | CH₃CO | CO | (CH₂)₃ | I |
| 1326 | — | — | CH₂ | 0 | 4 | COC₆H₅ | CH₃CO | CO | (CH₂)₃ | I |
| 1327 | — | — | CH₂ | 0 | 4 | H | H | CO | (CH₂)₃ | I |
| 1328 | — | — | CH₂ | 0 | 4 | H | Me | CO | (CH₂)₃ | I |
| 1329 | — | — | CH₂ | 0 | 4 | H | C₆H₅CO | CO | (CH₂)₃ | I |
| 1330 | — | — | CH₂ | 0 | 4 | H | CH₃CO | CH₂ | CH₂ | I |
| 1331 | — | — | CH₂ | 0 | 4 | Me | CH₃CO | CH₂ | CH₂ | I |
| 1332 | — | — | CH₂ | 0 | 4 | Et | CH₃CO | CH₂ | CH₂ | I |
| 1333 | — | — | CH₂ | 0 | 4 | COCH₃ | CH₃CO | CH₂ | CH₂ | I |
| 1334 | — | — | CH₂ | 0 | 4 | COC₆H₅ | CH₃CO | CH₂ | CH₂ | I |
| 1335 | — | — | CH₂ | 0 | 4 | H | H | CH₂ | CH₂ | I |
| 1336 | — | — | CH₂ | 0 | 4 | H | Me | CH₂ | CH₂ | I |
| 1337 | — | — | CH₂ | 0 | 4 | H | C₆H₅CO | CH₂ | CH₂ | I |

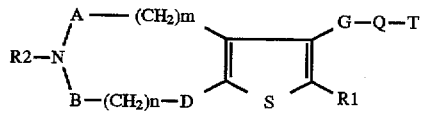

-continued

| | | | | | | | | | | |
|---|---|---|---|---|---|---|---|---|---|---|
| 1338 | — | — | CH₂ | 2 | 0 | Me | CH₃CO | CH₂ | CH₂ | II |
| 1339 | — | — | CH₂ | 2 | 0 | Me | CH₃CO | CH₂ | CH₂ | III |
| 1340 | — | — | CH₂ | 2 | 0 | Me | CH₃CO | CH₂ | CH₂ | IV |
| 1341 | — | — | CH₂ | 2 | 0 | Me | CH₃CO | CH₂ | CH₂ | V |
| 1342 | — | — | CH₂ | 2 | 0 | Me | CH₃CO | CH₂ | CH₂ | VI |
| 1343 | — | — | CH₂ | 2 | 0 | Me | CH₃CO | CH₂ | CH₂ | VII |
| 1344 | — | — | CH₂ | 2 | 0 | Me | CH₃CO | CH₂ | CH₂ | VIII |
| 1345 | — | — | CH₂ | 2 | 0 | Me | CH₃CO | CH₂ | CH₂ | IX |
| 1346 | — | — | CH₂ | 2 | 0 | Me | CH₃CO | CH₂ | CH₂ | X |

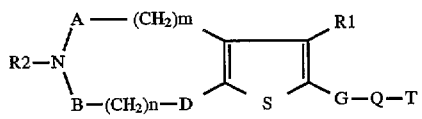

| | | | | | | | | | | |
|---|---|---|---|---|---|---|---|---|---|---|
| 1348 | — | CO | CH₂ | 0 | 2 | H | H | CH₂ | CH₂ | II |
| 1349 | — | CO | CH₂ | 0 | 2 | H | H | CH₂ | CH₂ | III |
| 1350 | — | CO | CH₂ | 0 | 2 | H | H | CH₂ | CH₂ | IV |
| 1351 | — | CO | CH₂ | 0 | 2 | H | H | CH₂ | CH₂ | V |
| 1352 | — | CO | CH₂ | 0 | 2 | H | H | CH₂ | CH₂ | VI |
| 1353 | — | CO | CH₂ | 0 | 2 | H | H | CH₂ | CH₂ | VII |
| 1354 | — | CO | CH₂ | 0 | 2 | H | H | CH₂ | CH₂ | VIII |
| 1355 | — | CO | CH₂ | 0 | 2 | H | H | CH₂ | CH₂ | IX |
| 1356 | — | CO | CH₂ | 0 | 2 | H | H | CH₂ | CH₂ | X |

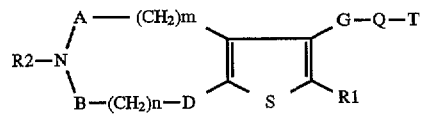

| | | | | | | | | | | |
|---|---|---|---|---|---|---|---|---|---|---|
| 1358 | — | CO | CH₂ | 0 | 2 | Me | H | CH₂ | CH₂ | II |
| 1359 | — | CO | CH₂ | 0 | 2 | Me | H | CH₂ | CH₂ | III |
| 1360 | — | CO | CH₂ | 0 | 2 | Me | H | CH₂ | CH₂ | IV |
| 1361 | — | CO | CH₂ | 0 | 2 | Me | H | CH₂ | CH₂ | V |
| 1352 | — | CO | CH₂ | 0 | 2 | Me | H | CH₂ | CH₂ | VI |
| 1363 | — | CO | CH₂ | 0 | 2 | Me | H | CH₂ | CH₂ | VII |
| 1364 | — | CO | CH₂ | 0 | 2 | Me | H | CH₂ | CH₂ | VIII |
| 1365 | — | CO | CH₂ | 0 | 2 | Me | H | CH₂ | CH₂ | IX |
| 1366 | — | CO | CH₂ | 0 | 2 | Me | H | CH₂ | CH₂ | X |

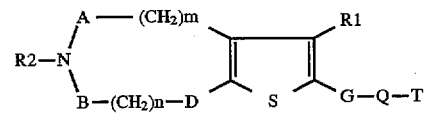

| | | | | | | | | | | |
|---|---|---|---|---|---|---|---|---|---|---|
| 1368 | — | — | CH₂ | 2 | 0 | Me | CH₃CO | CH₂ | CH₂ | II |
| 1369 | — | — | CH₂ | 2 | 0 | Me | CH₃CO | CH₂ | CH₂ | III |
| 1370 | — | — | CH₂ | 2 | 0 | Me | CH₃CO | CH₂ | CH₂ | IV |
| 1371 | — | — | CH₂ | 2 | 0 | Me | CH₃CO | CH₂ | CH₂ | V |
| 1372 | — | — | CH₂ | 2 | 0 | Me | CH₃CO | CH₂ | CH₂ | VI |
| 1373 | — | — | CH₂ | 2 | 0 | Me | CH₃CO | CH₂ | CH₂ | VII |
| 1374 | — | — | CH₂ | 2 | 0 | Me | CH₃CO | CH₂ | CH₂ | VIII |
| 1375 | — | — | CH₂ | 2 | 0 | Me | CH₃CO | CH₂ | CH₂ | IX |
| 1376 | — | — | CH₂ | 2 | 0 | Me | CH₃CO | CH₂ | CH₂ | X |
| 1378 | — | — | CH₂ | 2 | 0 | Me | CH₃CH₂CO | CH₂ | CH₂ | I |
| 1379 | — | — | CH₂ | 2 | 0 | Me | (CH₃)₂CHCO | CH₂ | CH₂ | I |
| 1380 | — | — | CH₂ | 2 | 0 | Me | Cyclopropyl-CO | CH₂ | CH₂ | I |
| 1381 | — | — | CH₂ | 2 | 0 | Me | C₆H₅CO | CH₂ | CH₂ | I |
| 1382 | — | — | CH₂ | 2 | 0 | Me | Cyclohexyl-CO | CH₂ | CH₂ | I |
| 1383 | — | — | CH₂ | 2 | 0 | Me | H | CH₂ | CH₂ | I |
| 1384 | — | — | CH₂ | 2 | 0 | Me | Me | CH₂ | CH₂ | I |

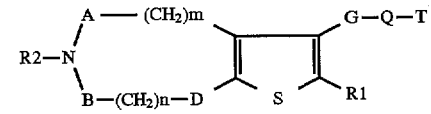

| | | | | | | | | | | |
|---|---|---|---|---|---|---|---|---|---|---|
| 1385 | — | — | CH₂ | 0 | 2 | Me | H | CH₂ | CH₂ | I |
| 1386 | — | — | CH₂ | 0 | 2 | Me | H | CO | (CH₂)₃ | I |
| 1387 | — | — | CH₂ | 1 | 1 | Me | H | CH₂ | CH₂ | I |
| 1388 | — | — | CH₂ | 1 | 1 | Me | H | CO | (CH₂)₃ | I |
| 1389 | — | — | CH₂ | 2 | 0 | Et | CH₃CO | CH₂ | CH₂ | V |

5,691,330

-continued $$R_2-N \begin{matrix} A-(CH_2)_m \\ B-(CH_2)_n-D \end{matrix} \begin{matrix} R_1 \\ S \end{matrix} G-Q-T$$

| No. | A | B | | m | n | D | R1 | S | G | Q | T |
|---|---|---|---|---|---|---|---|---|---|---|---|
| 1390 | — | — | CH₂ | 2 | 0 | H | COCH₃ | | CO | (CH₂)₃ | V |
| 1391 | — | CO | CH₂ | 0 | 2 | H | H | CH₂ | CO | CH₂ | V |

The pharmacological activities of the compound of formula (I) were examined by a series of receptor binding tests, anti-apomorphine action and anti-ergometrine action as described below.

Experiment Example 1: Affinity for dopamine 2 receptor

A specific binding of dopamine 2 ($D_2$) receptor was tested according to the method described in Eur. J. Pharmacol. 46, 377 (1977).

A synaptosome fraction was separated from corpus striatum of 9–10 week-old Wistar rats, and suspended in 50 mM Tris-HCl buffer (pH 7.1) containing 120 mM sodium chloride, 5 mM potassium chloride, 2 mM calcium chloride, 1 mM magnesium chloride, 10 μM pargyline and 0.1% ascorbic acid for the experiment.

The test compound at several concentrations and tritiated spiperone (final concentration 0.2 nM) were added to the synaptosome suspension, and each mixture was incubated at 37° C. for 20 minutes. After the incubation, the mixture was filtered with suction through Whatman GF/B (trade mark) glass filter. The filter was washed with 50 mM Tris-HCl buffer (pH 7.7), and the radioactivity of the filter was measured by a liquid scintillation counter. Non-specific binding was determined in the presence of $10^{-4}$ M (±)-sulpiride. The concentration necessary for 50% inhibition ($IC_{50}$) was determined on a graph, and inhibition constant (Ki value) was calculated. The results are shown in Table 1.

Experiment Example 2: Affinity for serotonin 2 receptor

A specific binding of serotonin 2 (5-$H_2$) receptor was tested according to the method described in Mol. Pharmacol. 21, 301 (1981).

A crude synaptosome fraction was separated from hippocampus of 9–10 week-old Wistar rats, and suspended in 50 mM Tris-HCl buffer (pH 7.7) for the experiment. The test compound at several concentration and tritiated ketanserin (final concentration 0.2 nM) were added to the synaptosome suspension, and each mixture was incubated at 37° C. for 20 minutes. After the incubation, the mixture was filtered with suction through Whatman GF/B (trade mark) glass filter. The filter was washed with 50 mM Tris-HCl buffer (pH 7.7), and the radioactivity of the filter was measured by a liquid scintillation counter. Non-specific binding was determined in the presence of $10^{-5}$M mianserin. The concentration necessary for 50% inhibition ($IC_{50}$) was determined on a graph, and inhibition constant (Ki value) was calculated. The result are shown in Table 1.

Experiment Example 3: Affinity for serotonin 1A receptor

A specific binding of serotonin 1A (5-$HT_{1A}$) receptor was tested according to the method described in J. Neurochem. 44, 1685 (1985).

A crude synaptosome fraction was separated from hippocampus of 9–10 week-old Wistar rats, and suspended in 50 mM Tris-HCl buffer (pH 7.4) containing 1 mM manganese chloride for the experiment. The test compound at several concentrations and tritiated 8-hydroxy-2-dipropyl-aminotetralin (8-OH-DPAT, final concentration 0.2 nM) were added to the synaptosome suspension, and each mixture was incubated at 37° C. for 12 minutes. After the incubation, the mixture was filtered with suction through Whatman GF/B (trade mark) glass filter. The filter was washed with 50 mM Tris-HCl buffer (pH 7.7), and the radioactivity of the filter was measured by a liquid scintillation counter. Non-specific binding was determined in the presence of $10^{-5}$ M serotonin (5-HT). The concentration necessary for 50% inhibition ($IC_{50}$) was determined on a graph, and inhibition constant (Ki value) was calculated. The results are shown in Table 1.

TABLE 1

| Test compound | Ki (nM) | | |
|---|---|---|---|
| (Example No.) | $D_2$ | 5-$HT_2$ | 5-$HT_{1A}$ |
| 15 | 0.065 | 0.32 | 1.6 |
| 22 | 0.52 | 0.21 | 15 |
| 24 | 0.46 | 0.062 | 32 |
| 32 | 0.10 | 0.086 | 54 |
| 42 | 0.23 | 0.20 | 1.1 |
| 43 | 1.5 | 0.11 | 87 |
| 53 | 0.15 | 0.043 | 3.7 |
| 73 | 0.25 | 0.082 | 0.16 |
| 84 | 0.21 | 0.18 | 0.13 |
| 85 | 0.52 | 0.38 | 0.31 |
| 86 | 0.17 | 0.092 | 0.59 |
| 145 | 3.8 | 2.8 | 0.14 |
| 147 | 0.4 | 0.86 | 0.32 |
| 148 | 2.3 | 8.6 | 0.24 |

Experiment Example 4: Anti-apomorphine action (in mouse)

Male dd mice at 3 per group were used for the experiment. The test compound was orally administered to the mice, and 60 minutes later, 0.5 mg/kg of apomorphine hydrochloride was subcutaneously administered.

the movement for 20 minutes from immediately after the administration of apomorphine hydrochloride was measured using Valimex (Columbus, USA). Each group was tested four times, and the amount of the test compound necessary to lower the movement by 50% than that of a control group was calculated from a graph and taken as $ED_{50}$. The results are shown in Table 2.

Experiment Example 5: Anti-ergometrine action

Male ddY mice at 12 per group were used for the experiment. The test compound was orally administered to the mice, and 60 minutes later, 20 mg/kg of ergometrine maleate was intraperitoneally administered. The amount of the test compound necessary to vanish the head-twitch reaction for 10 minutes from immediately after the administration of ergometrine maleate was calculated as $ED_{50}$ value by Probit method. The results are shown in Table 2.

TABLE 2

| Test compound (Example No.) | ED$_{50}$ (mg/kg, p.o.) | |
|---|---|---|
|  | anti-apomorphine | anti-ergometrine |
| 15 | 0.063 | 0.089 |
| 22 | 1.1 | 1.5 |
| 24 | 0.39 | 0.37 |
| 42 | 0.20 | 0.19 |
| 73 | 0.25 | 0.35 |
| 84 | 0.73 | 0.95 |
| 85 | 0.79 | 0.52 |
| 86 | 0.54 | 0.27 |

Experimental Example 6: Catalepsy Test

The method of Simon, P. et al (J. Pharm. Pharmacol., 22, 546, 1970) was utilized with a slight modification.

Catalepsy in rats was evaluated at the various time after oral administration of test drugs using a horizontal bar positioned 7 cm above the bench. Cataleptogenic activity was judged to be positive when the forepaws of the rats remained on the bar for more than 30 sec. Ten rats at each dose level were used to determine the ED$_{50}$ value required to induce catalepsy in 50% of the animals.

Experiment Example 7: Acute toxicity

Male ddY mice weighing 20–28 g were used at 10 per group. They were orally administered with the compound of Example 24 and observed for 5 days after the administration. The LD$_{50}$ (50% lethal dose) was 205 mg/kg.

The compounds of formula (I) were found to have high affinities for dopamine (D$_2$) receptor and serotonin (5-HT$_{1A}$, 5-HT$_2$) receptors according to the receptor binding assay using the radioligands. And they possessed D$_2$ antagonistic, 5-HT$_2$ antagonistic and 5-HT$_{1A}$ agonistic activities according to the inhibition of apomorphine-induced hyperactivity, ergometrine-induced head-twitches and forskolin-induced adenylate cyclase activity, respectively. Further they were found to have the inhibitory activity of spontaneous locomotor activity, methanphetamine-induced hyperactivity and conditioned avoidance responding. Therefore, these compounds will be effective for the positive symptoms such as hallucination and dellusion. And they were found to be effective for the forced swimming test, an indication of activation, and to have low cataleptogenic activity, an indication of the extrapyramidal side-effects. Therefore, these compounds will also be effective for the negative symptoms, such as apathy and social withdrawal. And they will be effective antipsychotic drugs with the potential for fewer extrapyramidal side-effects. The compounds of formula (II) are useful as synthetic intermediate for the compounds of formula (I).

When the compounds of formula (I) of the present invention are used as pharmaceuticals, a therapeutically effective amount of the compounds and adequate pharmacologically acceptable additives such as excipient, carrier, diluent and so on are mixed to be formulated into a form such as tablets, capsules, granules, syrups, injectable solutions, suppositories, dispersible powders or the like and are administered in the form mentioned above. The dosage may generally range about 5 to about 500 mg per day for an adult in a single dose or divided doses in the case of oral administration.

DESCRIPTION OF THE PREFERRED EMBODIMENTS

The present invention will be explained in more detail by the following examples, but these examples are not to be construed as limiting the present invention. The following compounds obtained can be identified by the various analysis such as NMR, IR, elemental analysis, mass spectrometry and so on.

Reference Example 1

To a solution of 171 g of 2-methylthiophene in 1500 ml of methylene chloride were added dropwise 500 g of tin(IV) chloride and 300 g of ethyl succinyl chloride under ice-cooling and the mixture was stirred for 1.5 hours. The mixture was poured into water, extracted with chloroform and the organic layer was washed with water, dried over magnesium sulfate and distilled away. To the residue was added isopropyl ether and the precipitated crystals were collected by filtration to give 299 g of white crystals. The resulting crystals were dissolved in 1600 ml of diethylene glycol and 264 g of 100% hydrazine monohydrate was add thereto and the mixture was stirred at 110° C. for 45 minutes. After cooling to 60° C., 445 g of potassium hydroxide was added thereto and the mixture was stirred at 140° C. for 1.5 hours. The mixture was poured into water, acidified with hydrochloric acid and extracted with ethyl acetate. The organic layer was dried over magnesium sulfate and the solvent was distilled away. The residue was dissolved in 500 ml of acetic anhydride, 5 ml of phosphoric acid was added thereto and the mixture was refluxed with stirring for 80 minutes. The mixture was poured into water, made alkaline with potassium carbonate and extracted with ethyl acetate. The organic layer was washed with water, dried over magnesium sulfate and concentrated in vacuo. The mixture of 164 g of the residue, 103 g of hydroxylamine hydrochloride and 124 g of sodium hydrogencarbonate in 500 ml of ethanol was refluxed with stirring for 1.5 hours. The mixture was concentrated in vacuo, water was added to the residue and extracted with ethyl acetate. The organic layer was washed with water, dried and distilled away. The residue was recrystallized from ethanol to give 152 g of white crystals. The resulting crystals were portionwise added to polyphosphoric acid at 60° C. The mixture was poured into water and extracted with chloroform. The extract was washed with water, dried over magnesium sulfate and concentrated in vacuo. The residue was chromatographed on a silica gel to give 30 g of 2-methyl-4,6,7,8-tetrahydro-5H-thieno[3,2-b]azepin-5-one (m.p. 133°–135° C.) and 93 g of 2-methyl-5,6,7,8-tetrahydro-4H-thieno[3,2-c]azepin-4-one (m.p. 119°–120° C.).

Reference Example 2

To a mixture of 61 g of thiophene in 800 ml of tetrahydrofuran was added 500 ml of n-butyllithium dropwise at −25° C. and the mixture was stirred for an hour. To the mixture was added 24.4 g of sulfur at −25° C., the mixture was stirred for 1.5 hours and 111.1 g of 3-bromopropionic acid in 50.1 g of potassium carbonate solution was added dropwise thereto, and then the mixture was stirred at room temperature for 4 hours. The aqueous layer was collected fractionally, washed with toluene, acidified with hydrochloric acid and extracted with chloroform. The organic layer was washed with water, dried and concentrated to give 135 g of a pale yellow oil. To a solution of 125 g of the oil in 1200 ml of toluene was added 153.6 g of trifluoroacetic anhydride dropwise, the mixture was stirred at room temperature for an hour and stirred at 40° C. for further 2 hours. The mixture was poured into ice-cold water and neutralized with sodium hydroxide solution. The toluene layer was washed with water, dried and concentrated in vacuo to give 103 g of a brown oil. To a solution of 103 g of the oil in 1000 ml of ethanol were added 49.9 g of hydroxylamine hydrochloride and 60.3 g of sodium hydrogencarbonate and the mixture was refluxed with stirring for 2 hours. Inorganic substances were filtered off and the filtrate was concentrated. To the residue was added isopropyl ether and the crystals were collected by filtration to give 77 g of white crystals. The resulting crystals were added portionwise to 100% polyphosphoric acid at 70° C. and the mixture was stirred at 80° C. for an hour. After the mixture was poured into water, the precipitated crystals were collected by filtration and recrystallized from ethanol to give 63 g of 2,3-dihydrothieno[3,2-f][1,4]thiazepin-5(4H)-one as pale brown crystals, m.p. 157°–158° C.

EXAMPLE 1

To a mixture of 13 g of 2,3-dihydrothieno[3,2-f][1,4]thiazepin-5(4H)-one and 21.5 g of 4-chlorobutyryl chloride in 200 ml of dichloroethane was added 21.5 g of aluminum chloride under cooling and the mixture was stirred for 3 hours. The mixture was poured into ice-cold water and extracted with chloroform. The organic layer was washed with saline solution, dried over magnesium sulfate and concentrated. The residue was recrystallized from ethanol to give 12 g of 7-(4-chlorobutyryl)-2,3-dihydrothieno[3,2-f][1,4]thiazepin-5(4H)-one as white crystals, m.p. 124°–125° C.

EXAMPLE 2

To a mixture of 5 g of 2-methyl-5,6,7,8-tetrahydro-4H-thieno[3,2-c]azepin-4-one and 5 g of 4-chlorobutyryl chloride in 50 ml of dichloroethane was added 8.6 g of aluminum chloride under ice-cooling and the mixture was stirred for 3 hours. The mixture was poured into ice-cold water and extracted with chloroform. The organic layer was washed with saline solution, dried over magnesium sulfate and concentrated. The residue was recrystallized from ethanol to give 1.2 g of 3-(4-chlorobutyryl)-2-methyl-5,6,7,8-tetrahydro-4H-thieno[3,2-c]azepin-4-one as white crystals, m.p. 113°–115° C.

EXAMPLE 3

To a mixture of 5 g of 2-methyl-5,6,7,8-tetrahydro-4H-thieno[3,2-b]azepin-5-one and 4.5 g of 3-chloropropionyl chloride in 50 ml of dichloroethane was added 9.2 g of aluminum chloride and the mixture was stirred for 3 hours. The mixture was poured into ice-cold water and extracted with chloroform. The organic layer was washed with saline solution, dried over magnesium sulfate and concentrated. The residue was recrystallized from ethanol to give 5.6 g of 3-(3-chloropropionyl)-2-methyl-5,6,7,8-tetrahydro-4H-thieno[3,2-b]azepin-5-one as white crystals, m.p. 86°–87° C.

EXAMPLE 4

The mixture of 1.0 g of 4-(1,2-benzisothiazol-3-yl)piperazine hydrochloride, 1.5 g of 7-(4-chlorobutyryl)-2,3-dihydrothieno[3,2-f][1,4]thiazepin-5(4H)-one, 2.5 g of potassium carbonate and 0.8 g of potassium iodide in 25 ml of N,N-dimethylformamide and 25 ml of toluene was stirred at 100° C. for 24 hours. After the mixture was cooled in a water bath, water was added thereto and the mixture was extracted with ethyl acetate. The organic layer was washed with saline solution, dried over magnesium sulfate and concentrated. The residue was purified by column chromatography on a silica gel, dissolved in isopropyl alcohol and oxalic acid was added thereto to make oxalate. The resulting crystals were recrystallized from isopropyl alcohol to give 0.12 g of 7-(4-(4-(1,2-benzisothiazol-3-yl)piperazin-1-yl)butyryl)-2,3-dihydrothieno[3,2-f][1,4]thiazepin-5(4H)-one oxalate ½ hydrate as white crystals, m.p. 118°–120° C.

EXAMPLE 5

The mixture of 2.0 g of 4-(1,2-benzisothiazol-3-yl)piperazine hydrochloride, 2.0 g of 3-(4-chlorobutyryl)-2-methyl-5,6,7,8-tetrahydro-4H-thieno[3,2-c]azepin-4-one, 2.1 g of potassium carbonate and 1.2 g of potassium iodide in 15 ml of N,N-dimethylformamide and 15 ml of toluene was stirred at 60° C. for 3 hours. After the mixture was cooled in a water bath, water was added thereto and the mixture was extracted with ethyl acetate. The organic layer was washed with saline solution, dried over magnesium sulfate and concentrated. The residue was purified by column chromatography on a silica gel, dissolved in isopropyl alcohol and ethanol-maleic acid was added thereto to make meleate. The resulting crystals were recrystallized from ethanol to give 0.90 g of 3-(4-(4-(1,2-benzisothiazol-3-yl)piperazin-1-yl)butyryl)-2-methyl-5,6,7,8-tetrahydro-4H-thieno[3,2-c]azepin-4-one maleate as white crystals, m.p. 150°–152° C.

EXAMPLE 6

The mixture of 2.1 g of 4-(1,2-benzisothiazol-3-yl)piperazine hydrochloride, 2.0 g of 3-(3-chloropropionyl)-2-methyl-4,6,7,8-tetrahydro-5H-thieno[3,2-b]azepin-5-one, 2,2 g of potassium carbonate and 1.2 g of potassium iodide in 15 ml of N,N-dimethylformamide and 15 ml of toluene was stirred at 60° C. for 5 hours. After the mixture was cooled in a water bath, water was added thereto and the mixture was extracted with ethyl acetate. The organic layer was washed with saline solution, dried over magnesium sulfate and concentrated. The residue was purified by column chromatography on a silica gel, dissolved in isopropyl alcohol and crystallized from isopropyl alcohol-isopropyl ether. The resulting crystals were recrystallized from ethanol to give 1.30 g of 3-(3-(4-(1,2-benzisothiazol-3-yl)piperazin-1-yl)propionyl)-2-methyl-4,6,7,8-tetrahydro-5H-thieno[3,2-b]azepin-5-one as white crystals, m.p. 146°–147° C.

EXAMPLE 7

The mixture of 2.4 g of 4-(bis(4-chlorophenyl)methyl)piperazine, 2.0 g of 7-(4-chlorobutyryl)-2,3-dihydrothieno[3,2-f][1,4]thiazepin-5(4H)-one, 1.9 g of potassium carbonate and 1.2g of potassium iodide in 15 ml of N,N-dimethylformamide and 15 ml of toluene was stirred at 60° C. for 5 hours. After the mixture was cooled in a water bath, water was added thereto. The precipitated crystals were filtered off and the filtrate was extracted with toluene. The organic layer was washed with saline solution, dried over magnesium sulfate and concentrated. The residue was purified by column chromatography on a silica gel and the resulting crystals were recrystallized from isopropyl alcohol-isopropyl ether to give 0.18 g of 7-(4-(4-(bis(4-chlorophenyl)-methyl)piperazin-1-yl)butyryl)-2,3-dihydrothieno[3,2-f][1,4]thiazepin-5(4H)-one as white crystals, m.p. 185°–187° C. (decomposition).

The following compounds can be prepared in a similar manner as the above.

EXAMPLE 8

2-(4-(4-(2-methoxyphenyl)piperazin-1-yl)butyryl)-4,6,7,8-tetrahydro-5H-thieno[3,2-b]azepin-5-one, m.p. 161+–162° C.

EXAMPLE 9

2-(4-(4-(4-chlorophenyl)-4-hydroxypiperidin-1-yl)butyryl)-4,6,7,8-tetrahydro-5H-thieno[3,2-b]azepin-5-one, m.p. 192°–194° C.

EXAMPLE 10

2-(3-(4-(2-methoxyphenyl)piperazin-1-yl)propionyl)-4,6,7,8-tetrahydro-5H-thieno[3,2-b]azepin-5-one, m.p. 161°–162° C.

EXAMPLE 11

2-(3-(4-(3-trifluoromethylphenyl)piperazin-1-yl)propionyl)-4,6,7,8-tetrahydro-5H-thieno[3,2-b]azepin-5-one, m.p. 137°–138° C.

EXAMPLE 12

7-(4-(4-(2-methoxyphenyl)piperazin-1-yl)butyryl)-2,3-dihydrothieno[3,2-f][1,4]thiazepin-5(4H)-one, m.p. 197°–198° C.

EXAMPLE 13

2-methyl-3-(4-(4-(2-methoxyphenyl)piperazin-1-yl)butyryl)-5,6,7,8-tetrahydro-4H-thieno[3,2-c]azepin-4-one hydrochloride, m.p. 220°–222° C.

EXAMPLE 14

7-(4-(4-(6-fluoro-1,2-benzisoxazol-3-yl)piperidin-1-yl)butyryl)-2,3-dihydrothieno[3,2-f][1,4]thiazepin-5(4H)-one, m.p. 186°–187° C.

EXAMPLE 15

2-(2-(4-(6-fluoro-1,2-benzisoxazol-3-yl)piperidin-1-yl)ethyl)-4,6,7,8-tetrahydro-5H-thieno[3,2-b]azepin-5-one, m.p. 210°–212° C. (decomposition).

EXAMPLE 16

2,4-dimethyl-3-(2-(4-(6-fluoro-1,2-benzisoxazol-3-yl)piperidin-1-yl)ethyl)-4,6,7,8-tetrahydro-5H-thieno[3,2-b]azepin-5-one hydrochloride, m.p. 250° C. (decomposition).

EXAMPLE 17

3-(4-(4-(6-fluoro-1,2-benzisoxazol-3-yl)piperidin-1-yl)butyryl)-2-methyl-4,6,7,8-tetrahydro-5H-thieno[3,2-b]azepin-5-one oxalate 3/2hydrate, m.p. 115°–118° C.

EXAMPLE 18

2-(4-(4-(6-fluoro-1,2-benzisoxazol-3-yl)piperidin-1-yl)butyryl)-3-methyl-4,6,7,8-tetrahydro-5H-thieno[3,2-b]azepin-5-one, m.p. 172°–175° C.

EXAMPLE 19

3-(2-(4-(6-fluoro-1,2-benzisoxazol-3-yl)piperidin-1-yl)ethyl)-2-methyl-4,6,7,8-tetrahydro-5H-thieno[3,2-b]azepin-5-one hydrochloride, m.p. 184°–186° C. (decomposition).

EXAMPLE 20

3-(4-(4-(6-fluoro-1,2-benzisoxazol-3-yl)piperidin-1-yl)butyryl)-2-methyl-5,6,7,8-tetrahydro-4H-thieno[3,2-c]azepin-4-one oxalate, m.p. 114°–117° C.

EXAMPLE 21

3-(4-(4-(6-fluoro-1,2-benzisoxazol-3-yl)piperidin-1-yl)acetyl)-2-methyl-4,6,7,8-tetrahydro-5H-thieno[3,2-b]azepin-5-one hydrochloride ½hydrate, m.p. 208°–210° C. (decomposition).

EXAMPLE 22

3-(2-(4-(6-fluoro-1,2-benzisoxazol-3-yl)piperidin-1-yl)ethyl)-2-methyl-4,6,7,8-tetrahydro-5H-thieno[3,2-b]azepin-5-one, m.p. 165°–167° C.

EXAMPLE 23

2-(2-(4-(6-fluoro-1,2-benzisoxazol-3-yl)piperidin-1-yl)ethyl)-5,6,7,8-tetrahydro-4 H-thieno[3,2-c]azepin-4-one, m.p. 182°–184° C.

- 2-(4-(4-(6-fluoro-1,2-benzisoxazol-3-yl)piperidin-1-yl)butyryl)-4,6,7,8-tetrahydro-5H-thieno[3,2-c]azepin-4-one
- 2-(4-(4-(6-fluoro-1,2-benzisoxazol-3-yl)piperidin-1-yl)butyryl)-4,6,7,8,-tetrahydro-5H-thieno[3,2-b]azepin-5-one
- 7-(4-(4-(6-fluoro-1,2-benzisoxazol-3-yl)piperidin-1-yl)butyryl)-2,3-dihydrothieno[3,2-f][1,4]thiazepin-5(4H)-one
- 7-(4-(4-(6-fluoro-1,2-benzisoxazol-3-yl)piperidin-1-yl)butyryl)-3,4-dihydrothieno[2,3-b][1,4]thiazepin-2(1H)-one
- 2-(4-(4-(6-fluoro-1,2-benzisoxazol-3-yl)piperidin-1-yl)-1-hydroxybutyl)-5,6,7,8-tetrahydro-4H-thieno[3,2-c]azepin-4-one
- 2-(4-(4-(6-fluoro-1,2-benzisoxazol-3-yl)piperidin-1-yl)butyl)-5,6,7,8-tetrahydro-4H-thieno[3,2-c]azepin-4-one
- 2-(2-(4-(6-fluoro-1,2-benzisoxazol-3-yl)piperidin-1-yl)acetyl)-5,6,7,8-tetrahydro-4H-thieno[3,2-c]azepin-4-one
- 2-(2-(4-(6-fluoro-1,2-benzisoxazol-3-yl)piperidin-1-yl)acetyl)-4,6,7,8-tetrahydro-5H-thieno[3,2-b]azepin-5-one
- 2-(2-(4-(6-fluoro-1,2-benzisoxazol-3-yl)piperidin-1-yl)ethyl)-5,6,7,8-tetrahydro-4H-thieno[3,2-c]azepin-4-one
- 2-(2-(4-(6-fluoro-1,2-benzisoxazol-3-yl)piperidin-1-yl)ethyl)-4,6,7,8-tetrahydro-5H-thieno[3,2-b]azepin-5-one
- 2-(4-(N,N-dimethylamino)butyryl)-5,6,7,8-tetrahydro-4H-thieno[3,2-c]azepin-4-one
- 2-(4-(N,N-dimethylamino)butyryl)-4,6,7,8-tetrahydro-5H-thieno[3,2-b]azepin-5-one
- 2-(2-(N,N-dimethylamino)acetyl)-5,6,7,8-tetrahydro-4H-thieno[3,2-c]azepin-4-one
- 2-(2-(N,N-dimethylamino)acetyl)-4,6,7,8-tetrahydro-5H-thieno[3,2-b]azepin-5-one
- 2-(3-(4-(6-fluoro-1,2-benzisoxazol-3-yl)piperidin-1-yl)propylthio)-5,6,7,8-tetrahydro-4H-thieno[3,2-c]azepin-4-one
- 2-(3-(4-(6-fluoro-1,2-benzisoxazol-3-yl)piperidin-1-yl)propylsulfinyl)-5,6,7,8-tetrahydro-4H-thieno[3,2-c]azepin-4-one
- 2-(3-(4-(6-fluoro-1,2-benzisoxazol-3-yl)piperidin-1-yl)propylsulfonyl)-5,6,7,8-tetrahydro-4H-thieno[3,2-c]azepin-4-one
- 2-(3-(4-(6-fluoro-1,2-benzisoxazol-3-yl)piperidin-1-yl)propylthio)-4,6,7,8-tetrahydro-5H-thieno[3,2-b]azepin-5-one
- 2-(3-(4-(6-fluoro-1,2-benzisoxazol-3-yl)piperidin-1-yl)propylsulfinyl)-4,6,7,8-tetrahydro-5H-thieno[3,2-b]azepin-5-one
- 2-(3-(4-(6-fluoro-1,2-benzisoxazol-3-yl)piperidin-1-yl)propylsulfonyl)-4,6,7,8-tetrahydro-5H-thieno[3,2-b]azepin-5-one
- 2-(4-(4-(6-fluoro-1,2-benzisoxazol-3-yl)piperidin-1-yl)butyryl)-4,5-dihydrothieno[2,3-b]pyridin-6(7H)-one
- 2-(4-(4-(6-fluoro-1,2-benzisoxazol-3-yl)piperidin-1-yl)butyryl)-4,5-dihydrothieno[2,3-c]pyridin-7(6H)-one ⊚ 2-(4-(4-(6-fluoro-1,2-benzisoxazol-3-yl)piperidin-1-yl)butyryl)-4,5-dihydro-7H-thieno[3,2-c]pyridin-6-one ⊚ 2-(4-(4-(6-fluoro-1,2-benzisoxazol-3-yl)piperidin-1-yl)butyryl)-6,7-dihydro-4H-thieno[2,3-c]pyridin-5-one ⊚ 2-(2-(4-(6-fluoro-1,2-benzisoxazol-3-yl)piperidin-1-yl)acetyl)-4,5-dihydro-7H-thieno[3,2-c]pyridin-6-one ⊚ 2-(2-(4-(6-fluoro-1,2-benzisoxazol-3-yl)piperidin-1-yl)acetyl)-6,7-dihydro-4H-thieno[2,3-c]pyridin-5-one ⊚ 2-(3-(4-(6-fluoro-1,2-benzisoxazol-3-yl)piperidin-1-yl)propylthio)-6,7-dihydro-4H-thieno[2,3-c]pyridin-5-one ⊚ 2-(3-(4-(6-fluoro-1,2-benzisoxazol-3-yl)piperidin-1-yl)propylsulfinyl)-6,7-dihydro-4H-thieno[2,3-c]pyridin-5-one ⊚ 2-(3-(4-(6-fluoro-1,2-benzisoxazol-3-yl)piperidin-1-yl)propylsulfonyl)-6,7-dihydro-4H-thieno[2,3-c]pyridin-5-one.

Reference Example 3

A mixture of 50 g of 5-methyl-2-thiophenealdehyde and 42 g of aminoacetoaldehyde dimethyl acetal was stirred at 60°–70° C. for an hour and concentrated to give 71 g of oil. The resulting oil was dissolved in 450 ml of methanol, 25 g of sodium borohydride was added thereto under cooling and the mixture was stirred for 10–20 minutes, and then concentrated. To the residue was added water and extracted with chloroform. The extract was washed with water, dried over magnesium sulfate and concentrated. To the residue were added 264 ml of water and 132 ml of conc. hydrochloric acid and the mixture was stirred at 50° C. for 2 hours. After cooling, 50 ml of conc. hydrochloric acid and 265 g of tin(II) chloride dihydrate were added thereto and the mixture was stirred at 60° C. for 2 hours. The mixture was poured into water, made alkaline with 40% sodium hydroxide solution and extracted with chloroform. The organic layer was washed with water, dried over magnesium sulfate and concentrated. The residue was dissolved in 200 ml of tetrahydrofuran, and 80 ml of triethylamine and 40 ml of acetic anhydride were added thereto under cooling, and then the mixture was stirred for an hour. The mixture was poured into water, extracted with ethyl acetate and the extract was washed with water, dried and concentrated. The residue was subjected to column chromatography to give 27 g of 6-acetyl-4,5,6,7-tetrahydro-2-methylthieno[2,3-c]pyridine.

Reference Example 4

To a solution of 20 g of 4,5,6,7-tetrahydrothieno[3,2-c]pyridine as an oil obtained by a known method in 100 ml of tetrahydrofuran were added 30 ml of triethylamine and 15 ml of acetic anhydride under cooling. The mixutre was stirred for an hour, poured into water and extracted with ethyl acetate. The extract was washed with water, dried and concentrated to give 10 g of 5-acetyl-4,5,6,7-tetrahydrothieno[3,2-c]pyridine.

Preparative Example 1

To a mixture of 27 g of 6-acetyl-4,5,6,7-tetrahydro-2-methylthieno[2,3-c]pyridine and 16 g of acetyl chloride in 250 ml of dichloroethane was added 42 g of aluminum chloride under cooling and the mixture was stirred for 30 minutes. The mixture was poured into water and extracted with chloroform. The organic layer was washed with water, dried over magnesium sulfate and concentrated. The residue was dissolved in 300 ml of methanol, 20 g of bromine was added thereto at 30° C. and the mixture was stirred for 2 hours. The mixture was poured into water and extracted with ethyl acetate. The organic layer was washed with water, dried and concentrated to give 28 g of 6-acetyl-3-bromoacetyl-4,5,6,7-tetrahydro-2-methylthieno[2,3-c]pyridine.

Preparative Example 2

A mixture of 28 g of 6-acetyl-3-bromoacetyl-4,5,6,7-tetrahydro-2-methylthieno[2,3-c]pyridine in 42 ml of triethylsilane and 140 ml of trifluoroacetic acid was stirred at room temperature for 5 hours. The mixture was poured into water, made alkaline and extracted with ethyl acetate. The organic layer was washed with water, dried and concentrated. To the residue was added isopropyl ether and the precipitated crystals were collected by filtration to give 14 g of 6-acetyl-3-(2-bromoethyl)-4,5,6,7-tetrahydro-2-methylthieno[2,3-c]pyridine as white crystals, m.p. 93°–95° C.

The following compounds were prepared in a similar manner as the above. Figures mean δ value of $^1$H-NMR (CDCl$_3$).

⊚ 5-acetyl-2-(2-bromoethyl)-4,5,6,7-tetrahydrothieno[3,2-c]pyridine 6.66(s, 1H), 4.60(d,2H), 4.00–3.00(m,6H), 2.80(b,2H), 2.15(s,3H)

⊚ 6-acetyl-3-(3-chloropropyl)-4,5,6,7-tetrahydro-2-methylthieno[2,3-c]pyridine 4.66(d,2H), 4.00–3.30(m,4H), 2.50(b,4H), 2.33(s,3H), 2.15(s,3H), 1.50(m,2H)

⊚ 6-acetyl-2-(2-chloroethyl)-4,5,6,7-tetrahydro-3-methylthieno[2,3-c]pyridine 4.60(d,2H), 4.00–3.40(m,4H), 3.15(t,2H), 2.50(b,4H), 2.15(s,3H), 2.05(s,3H)

⊚ 6-acetyl-3-(4-chlorobutyl)-4,5,6,7-tetrahydro-2-methylthieno[2,3-c]pyridine 4.66(d,2H), 4.00–3.40(m,4H), 2.70–2.30(b,4H), 2.33(s,3H), 2.15(s,3H), 2.00–1.30(m,4H), ⊚ 6-acetyl-2-(2-bromoethyl)-4,5,6,7-tetrahydrothieno[2,3-c]pyridine 6.70(s,1H), 4.60(d,2H), 4.00–3.00(m,6H), 2.66(b,2H), 2.10(s,3H)

⊚ 6-acetyl-3-(2-chloroethyl)-4,5,6,7-tetrahydro-2-methylthieno[2,3-c]pyridine 4.65(d,2H), 4.05–3.40(m+t,4H), 2.95(t,2H), 2.65(b,2H), 2.40(s,3H), 2.20(s,3H)

⊚ 3,6-bisacetyl-2-(2-chloroethyl)-4,5,6,7-tetrahydro[2,3-c]pyridine 4.66(d,2H), 4.00–3.50(m+t,4H), 3.40(t,2H), 2,85(b,2H), 2.50(s,3H), 2.15(s,3H)

⊚ 6-acetyl-3-(2-chloroethyl)-4,5,6,7-tetrahydro-2-propylthieno[2,3-c]pyridine 4.66(d,2H), 4.00–3.33(m+t,4H), 3.00–2.33(m,6H), 2.15(s, 3H), 1.65(m,2H), 1.00(t,3H)

⊚ 6-acetyl-3-chloroacetyl-4,5,6,7-tetrahydro-2-methylthieno[2,3-c]pyridine 4.75(d,2H), 4.50(s,2H), 3.75(t,2H), 2.65(t,2H), 2.50(s,3H), 2.20(s,3H).

EXAMPLE 24

A mixture of 5.9 g of 6-acetyl-3-(2-bromoethyl)-4,5,6,7-tetrahydro-2-methylthieno[2,3-c]pyridine, 5 g of 4-(6-fluoro-1,2-benzisoxazol-3-yl)piperidine hydrochloride, 6.7 g of potassium carbonate and 3.2 g of potassium iodide in 50 ml of dimethylformamide and 50 ml of toluene was stirred at 50° C. for 7 hours and poured into water. The toluene layer was washed with water, dried over magnesium sulfate and concentrated. The residue was purified by column chromatography on a silica gel and crystallized from isopropyl ether. The resulting crystals were recrystallized from acetonitrile to give 6-acetyl-3-(2-(4-(6-fluoro-1,2-benzisoxazol-3-yl)piperidin-1-yl)ethyl)- 4,5,6,7-tetrahydro-2-methylthieno[2,3-c]pyridine, m.p. 70°–75° C.

EXAMPLE 25

A mixture of 4 g of 6-acetyl-3-(2-(4-(6-fluoro-1,2-benzisoxazol-3-yl)piperidin-1-yl)ethyl)-4,5,6,7-tetrahydro-2-methylthieno[2,3-c]pyridine in 4ml of conc. sulfuric acid and 80 ml of water was refluxed under heating for 3 hours. The mixture was poured into water, made alkaline and extracted with chloroform. The organic layer was washed with water, dried over magnesium sulfate and concentrated. To the residue was added isopropyl ether and the crystals were collected by filtration to give 3-(2-(4-(6-fluoro-1,2-benzisoxazol-3-yl)piperidin-1-yl)ethyl)-4,5,6,7-tetrahydro-2-methylthieno[2,3-c]pyridine, m.p. 88°–90° C.

EXAMPLE 26

To a mixture of 0.5 g of 3-(2-(4-(6-fluoro-1,2-benzisoxazol-3-yl)piperidin-1-yl)ethyl)-4,5,6,7-tetrahydro-2-methylthieno[2,3-c]pyridine in 0.5 ml of triethylamine and 10 ml of chloroform was added 0.18 g of benzoyl chloride under cooling and the mixture was stirred for an hour, and then poured into water. The organic layer was washed with water, dried and concentrated. The residue was purified by column chlomatogaphy to give 0.4 g of 6-benzoyl-3-(2-(4-(6-fluoro-1,2-benzisoxazol-3-yl)piperidin-1-yl)ethyl)-4,5,6,7-tetrahydro-2-methylthieno[2,3-c]pyridine as an oil, m.p. 192°–195° C. as oxalate ¼hydrate thereof.

EXAMPLE 27

The reaction and procedure were conducted in a similar manner as in Example 24 using 0.48 g of 6-acetyl-3-(2-bromoethyl)-4,5,6,7-tetrahydro-2-methylothieno[2,3-c]pyridine and 0.5 g of 4-((6,7-dimethoxy-1,2-benzisoxazol-3-yl)methyl)piperidine hydrochloride to give 0.4 g of 6-acetyl-3-(2-(4-((6,7-dimethoxy-1,2-benzisoxazol-3-yl)methyl)piperidin-1-yl)ethyl)-4,5,6,7-tetrahydro-2-methylthieno[2,3-c]pyridine as an oil, m.p. 197°–200° C. as oxalate thereof.

EXAMPLE 28

The reaction and procedure were conducted in a similar manner as in Example 26 using 0.19 g of cyclohexanecarbonyl chloride in stead of benzoyl chloride to give 0.06 g of 6-cyclohexylcarbonyl-3-(2-(4-(6-fluoro-1,2-benzisoxazol-3-yl)piperidin-1-yl)ethyl)-4,5,6,7-tetrahydro-2-methylthieno[2,3-c]pyridine as an oil, m.p. 205°–208° C. as oxalate ½hydrate thereof.

EXAMPLE 29

The reaction and procedure were conducted in a similar manner as in Example 24 using 1.4 g of 6-acetyl-3-(4-chlorobutyryl)-4,5,6,7-tetrahydro-2-methylthieno[2,3-c]pyridine and 1.3 g of 4-(6-fluoro-1,2-benzisoxazol-3-yl)piperidine hydrochloride to give 1.4 g of 6-acetyl-3-(4-(4-(6-fluoro-1,2-benzisoxazol-3-yl)piperidin-1-yl)butyryl)-4,5,6,7-tetrahydro-2-methylthieno[2,3-c]pyridine as an oil.

$^1$H-NMR(CDCl$_3$) δ:1.85–2.30(m,8H), 2.15(s,3H), 2.30–2.70(m,2H), 2.60(s,3H) 2.70–3.30(m,5H), 3.65(m, 4H), 4.60(d,2H), 7.05(dt,1H), 7.25(dd,1H), 7.70(dd,1H).

EXAMPLE 30

The reaction and procedure were conducted in a similar manner as in Example 24 using 1.5 g of 6-acetyl-3-(4-chlorobutyryl-4,5,6,7-tetrahydro-2-ethylthieno[2,3-c]pyridine and 1.2 g of 4-(6-fluoro-1,2-benzisoxazol-3-yl)piperidine hydrochloride to give 0.7 g of 6-acetyl-3-(4-(4-(6-fluoro-1,2-benzisoxazol-3-yl)piperidin-1-yl)butyryl)-4,5,6,7-tetrahydro-2-ethylthieno[2,3-c]pyridine as an oil, m.p. 93°–95° C. as oxalate ¼hydrate thereof.

EXAMPLE 31

The reaction and procedure were conducted in a similar manner as in Example 24 using 4.0 g of 6-acetyl-3-(2-bromoethyl)-4,5,6,7-tetrahydrothieno[2,3-c]pyridine and 3.0 g of 4-(6-fluoro-1,2-benzisoxazol-3-yl)piperidine hydrochloride to give 3.3 g of 6-acetyl-2-(2-(4-(6-fluoro-1,2-benzisoxazol-3-yl)piperidin-1-yl)ethyl)-4,5,6,7-tetrahydrothieno[2,3-c]pyridine as white crystals, m.p. 130°–132° C.

EXAMPLE 32

The reaction and procedure were conducted in a similar manner as in Example 24 using 2.5 g of 6-acetyl-3-(2-bromoethyl)-2-ethyl-4,5,6,7-tetrahydrothieno[2,3-c]pyridine and 2.0 g of 4-(6-fluoro-1,2-benzisoxazol-3-yl)piperidine hydrochloride to give 2.2 g of 6-acetyl-2-ethyl-3-(2-(4-(6-fluoro-1,2-benzisoxazol-3-yl)piperidin-1-yl)ethyl)-4,5,6,7-tetrahydrothieno[2,3-c]pyridine as an oil, m.p. 191°–201° C. as oxalate ½hydrate thereof.

EXAMPLE 33

The reaction and procedure were conducted in a similar manner as in Example 24 using 0.7 g of 5-acetyl-2-(2-bromoethyl)-4,5,6,7-tetrahydrothieno[2,3-c]pyridine and 0.61 g of 4-(6-fluoro-1,2-benzisoxazol-3-yl)piperidine hydrochloride to give 0.7 g of 5-acetyl-2-(2-(4-(6-fluoro-1,2-benzisoxazol-3-yl)piperidin-1-yl)ethyl)-4,5,6,7-tetrahydrothieno[2,3-c]pyridine as an oil, m.p. 170°–172° C. as oxalate thereof.

EXAMPLE 34

The reaction and procedure were conducted in a similar manner as in Example 24 using 0.7 g of 6-acetyl-3-(2-chloroethyl)-4,5,6,7-tetrahydro-2-methylthieno[2,3-c]pyridine and 0.6 g of 4-(bis(4-fluorophenyl)-methylene)piperidine to give 0.5 g of 6-acetyl-3-(2-(4-(bis(4-fluorophenyl)methylene)piperidin-1-yl)ethyl)-4,5,6,7-tetrahydro-2-methylthieno[2,3-c]pyridine as an oil, m.p. 209°–211° C. as axalate thereof.

EXAMPLE 35

The reaction and procedure were conducted in a similar manner as in Example 24 using 1.0 g of 6-acetyl-3-chloroacetyl-4,5,6,7-tetrahydro-2-methylthieno[2,3-c]pyridine and 0.95 g of 4-(6-fluoro-1,2-benzisoxazol-3-yl)piperidine hydrochloride to give 0.9 g of 6-acetyl-3-(2-(4-(6-fluoro-1,2-benzisoxazol-3-yl)piperidin-1-yl)-1-oxoethyl)-4,5,6,7-tetrahydro-2-methylthieno[2,3-c]pyridine as an oil, m.p. 92°–94° C. as 3/2oxalate ½hydrate thereof.

EXAMPLE 36

The reaction and procedure were conducted in a similar manner as in Example 24 using 1.7 g of 6-acetyl-3-(2-chloroethyl)-4,5,6,7-tetrahydro-2-propylthieno[2,3-c]pyridine and 1.0 g of 4-(6-fluoro-1,2-benzisoxazol-3-yl)piperidine hydrochloride to give 0.7 g of 6-acetyl-2-propyl-3-(2-(4-(6-fluoro-1,2-benzisoxazol-3-yl)piperidin-1-yl)

ethyl)-4,5,6,7-tetrahydrothieno[2,3-c]pyridine as an oil, m.p. 178°–180° C. (decomposition) as oxalate ½hydrate thereof.

EXAMPLE 37

The reaction and procedure were conducted in a similar manner as in Example 24 using 1.0 g of 6-acetyl-3-(4-chlorobutyl)-4,5,6,7-tetrahydro-2-methylthieno[2,3-c]pyridine and 0.9 g of 4-(6-fluoro-1,2-benzisoxazol-3-yl)piperidine hydrochloride to give 0.5 g of 6-acetyl-3-(4-(4-(6-fluoro-1,2-benzisoxazol-3-yl)piperidin-1-yl)butyl)-4,5,6,7-tetrahydro-2-methylthieno[2,3-c]pyridine as an oil, m.p. 158°–160° C. as 3/2oxalate thereof.

EXAMPLE 38

The reaction and procedure were conducted in a similar manner as in Example 24 using 2.0 g of 6-acetyl-(3-chloropropyl)-4,5,6,7-tetrahydro-2-methylthieno[2,3-c]pyridine and 2.0 g of 4-(6-fluoro-1,2-benzisoxazol-3-yl)piperidine hydrochloride to give 0.5 g of 6-acetyl-3-(3-(4-(6-fluoro-1,2-benzisoxazol-3-yl)piperidin-1-yl)propionyl)-4,5,6,7-tetrahydro-2-methylthieno[2,3-c]pyridine as an oil, m.p. 180°–182° C. as oxalate thereof.

EXAMPLE 39

To a solution of 0.5 g of 3-(2-(4-(6-fluoro-1,2-benzisoxazol-3-yl)piperidin-1-yl)ethyl)-4,5,6,7-tetrahydro-2-methylthieno[2,3-c]pyridine hydrochloride in ethanol was added 0.3 ml of 37% formaldehyde solution and the mixture was stirred at room temperature for an hour. To the mixture was added 0.2 g of sodium cyanoborohydride, the mixture was stirred for an hour, and then concentrated. To the residue was added water and extracted with chloroform. The extract was washed with water, dried and concentrated in vacuo. The residue was purified by column chromatography and recrystallized from isopropyl ether to give 2,6-dimethyl-3-(2-(4-(6-fluoro-1,2-benzisoxazol-3-yl)piperidin-1-yl)ethyl)-4,5,6,7-tetrahydrothieno[2,3-c]pyridine ½hydrate as white crystals, m.p. 100°–103° C.

EXAMPLE 40

A mixture of 0.8 g of 6-acetyl-3-(2-chloroethyl)-4,5,6,7-tetrahydro-2-methylthieno[2,3-c]pyridine and 20 ml of 16.8% dimethylamine-ethanol solution in a pressure bottle was stirred at 80° C. for 5 hours and then the solvent was distilled away. To the residue was added water and extracted with ethyl acetate. The extract was washed with water, dried and concentrated in vacuo to give 0.4 g of 6-acetyl-3-(2-dimethylaminoethyl)-4,5,6,7-tetrahydro-2-methylthieno[2,3-c]pyridine as an oil.

$^1$H-NMR(CDCl$_3$) δ:2.17(s,3H), 2.30(s,6H), 2.40(s,3H), 2.50–2.80 (m,6H), 3.80(m,2H), 4.66(d,2H).

EXAMPLE 41

The reaction and procedure were conducted in a similar manner as in Example 40 using 2.3 g of 5-acetyl-2-(2-chloroethyl)-4,5,6,7-tetrahydrothieno[3,2-c]pyridine to give 5-acetyl-2-(2-dimethylaminoethyl)-4,5,6,7-tetrahydrothieno[3,2-c]pyridine hydrochloride ¼hydrate, m.p. 201°–203° C. (decomposition).

EXAMPLE 42

The reaction and procedure were conducted in a similar manner as in Example 24 using 1.0 g of 6-acetyl-2-(2-chloroethyl)-4,5,6,7-tetrahydro-3-methylthieno[2,3-c]pyridine and 1.0 g of 4-(6-fluoro-1,2-benzisoxazol-3-yl)piperidine hydrochloride to give 6-acetyl-2-(2-(4-(6-fluoro-1,2-benzisoxazol-3-yl)piperidin-1-yl)ethyl)-4,5,6,7-tetrahydro-3-methylthieno[2,3-c]pyridine as an oil.

$^1$H-NMR(CDCl$_3$) δ:1.80–3.50(m,15H), 2.10(s,3H), 2.25(s,3H), 3.80(m,2H), 4.70(d,2H), 7.10(dt,1H), 7.30(dd,1H), 7.75(dd,1H).

EXAMPLE 43

The reaction and procedure were conducted in a similar manner as in Example 24 using 2.2 g of 6-acetyl-2-(4-chlorobutyryl)-4,5,6,7-tetrahydrothieno[2,3-c]pyridine and 2.0 g of 4-(6-fluoro-1,2-benzisoxazol-3-yl)piperidine hydrochloride to give 1.3 g of 6-acetyl-2-(4-(4-(6-fluoro-1,2-benzisoxazol-3-yl)piperidin-1-yl)butyryl)-4,5,6,7-tetrahydrothieno[2,3-c]pyridine as white crystals, m.p. 145°–147° C.

EXAMPLE 44

The reaction and procedure were conducted in a similar manner as in Example 26 using 0.12 g of propionyl chloride instead of benzoyl chloride to give 0.4 g of 3-(2-(4-(6-fluoro-1,2-benzisoxazol-3-yl)piperidin-1-yl)ethyl)-4,5,6,7-tetrahydro-2-methyl-6-propionylthieno[2,3-c]pyridine as an oil, m.p. 192°–195° C. (decomposition) as oxalate ½ hydrate thereof.

EXAMPLE 45

The reaction and procedure were conducted in a similar manner as in Example 26 using 0.15 g of isobutyryl chloride instead of benzoyl chloride to give 0.4 g of 3-(2-(4-(6-fluoro-1,2-benzisoxazol-3-yl)piperidin-1-yl)ethyl)-4,5,6,7-tetrahydro-6-isobutyryl-2-methylthieno[2,3-c]pyridine as an oil, m.p.200° C. (decomposition) as oxalate ⅓hydrate thereof.

EXAMPLE 46

The reaction and procedure were conducted in a similar manner as in Example 26 using 0.14 g of cyclopropylcarbonyl chloride instead of benzoyl chloride to give 0.4 g of 6-cyclopropylcarbonyl-3-(2-(4-(6-fluoro-1,2-benzisoxazol-3-yl)piperidin-1-yl)ethyl)-4,5,6,7-tetrahydro-2-methylthieno[2,3-c]pyridine as an oil, m.p. 188°–190° C. (decomposition) as oxalate ¼hydrate thereof.

EXAMPLE 47

The reaction and procedure were conducted in a similar manner as in Example 24 using 1.5 g of 3,6-diacetyl-2-(2-chloroethyl)-4,5,6,7-tetrahydrothieno[2,3-c]pyridine and 1.3 g of 4-(6-fluoro-1,2-benzisoxazol-3-yl)piperidine hydrochloride to give 3,6-diacetyl-2-(2-(4-(6-fluoro-1,2-benzisoxazol-3-yl)piperidin-1-yl)ethyl-4,5,6,7-tetrahydrothieno[2,3-c]pyridine as an oil.

$^1$H-NMR(CDCl$_3$) δ:1.80–2.60(m,7H), 2.20(s,3H), 2.50(s, 3H), 2.60–3.40 (m,8H), 3.65(m,2H), 4.60(d,2H), 7.05(dt, 1H), 7.25(dd,1H), 7.70(dd,1H).

EXAMPLE 48

The reaction and procedure were conducted in a similar manner as in Example 24 using 2.0 g of 5-acetyl-3-(2-chloroethyl)-4,5,6,7-tetrahydro-2-methylthieno[3,2-c]pyridine and 1.0 g of 4-(6-fluoro-1,2-benzisoxazol-3-yl)piperidine hydrochloride to give 0.25 g of 5-acetyl-3-(2-(4

-(6-fluoro-1,2-benzisoxazol-3-yl)piperidin-1-yl)ethyl)-4,5,6,7-tetrahydro-2-methylthieno[3,2-c]pyridine as an oil.

¹H-NMR(CDCl₃) δ:1.60–2.50(m,8H), 2.20(s,3H), 2.40(s, 3H), 2.50–2.90 (m,4H), 3.16(m,3H), 3.80(m,2H), 4.50(d, 2H), 7.05(dt,1H), 7.25(dd,1H), 7.70(dd,1H).

EXAMPLE 49

The reaction and procedure were conducted in a similar manner as in Example 24 using 1.4 g of 6-acetyl-3-(2-chloroethyl)-4,5,6,7-tetrahydro-2-methylthieno[2,3-c]pyridine and 0.9 g of 4-(1,2-benzisothiazol-3-yl)piperazine to give 1.0 g of 6-acetyl-3-(2-(4-(1,2-benzisothiazol-3-yl)piperazin-1-yl)ethyl)-4,5,6,7-tetrahydro-2-methylthieno[2,3-c]pyridine as an oil, m.p. 190°–192° C. (decomposition) as oxalate thereof.

EXAMPLE 50

The reaction and procedure were conducted in a similar manner as in Example 24 using 1.6 g of 5-acetyl-3-(4-chlorobutyryl)-4,5,6,7-tetrahydro-2-methylthieno[3,2-c]pyridine and 1.4 g of 4-(6-fluoro-1,2-benzisoxazol-3-yl)piperidine hydrochloride to give 0.6 g of 5-acetyl-3-(4-(6-fluoro-1,2-benzisoxazol-3-yl)piperidin-1-yl)butyryl)-4,5,6,7-tetrahydro-2-methylthieno[3,2-c]pyridine as an oil.

¹H-NMR(CDCl₃) δ:1.80–3.30(m,16H), 2.02(s,3H), 2.18 (s,3H), 3.75(m,3H), 4.70(d,2H). 7.04(dd,2H), 7.70(dd,1H).

EXAMPLE 51

A mixture of 334 mg of 6-acetyl-3-(2-bromoethyl)-4,5,6,7-tetrahydro-2-methylthieno[2,3-c]pyridine, 420 mg of 4-(6-fluoro-1-(4-fluorophenyl)-1H-indazol-3-yl)piperidine hydrochloride, 500 mg of potassium carbonate and 216 mg of potassium iodide in 10 ml of dimethylformamide and 10 ml of toluene was stirred at 8520 C. for 8 hours and concentrated in vacuo. To the residue were added ethyl acetate and water, and separated. The ethyl acetate layer was washed with water, dried over magnesium sulfate and concentrated in vacuo. The residue was purified by column chromatography on a silica gel to give 360 mg of 6-acetyl-3-(2-(4-(6-fluoro-1-(4-fluorophenyl)-1H-indazol-3-yl)piperidin-1-yl)ethyl)-4,5,6,7-tetrahydro-2-methylthieno[2,3-c]pyridine as an oil, m.p. 193°–196° C. as oxalate thereof.

EXAMPLE 52

A mixture of 334 mg of 6-acetyl-3-(2-bromoethyl)-4,5,6,7-tetrahydro-2-methylthieno[2,3-c]pyridine, 308 mg of 4-(5-fluoro-1,2-benzisoxazol-3-yl)piperidine hydrochloride, 500 mg of potassium carbonate and 220 mg of potassium iodide in 10 ml of dimethylformamide and 10 ml of toluene was stirred at 90° C. for 25 hours and concentrated in vacuo. To the residue were added ethyl acetate and water and separated. The ethyl acetate layer was washed with water, dried over magnesium sulfate and concentrated in vacuo. The residue was purified by column chromatography on a silica gel to give 100 mg of 6-acetyl-3-(2-(4-(5-fluoro-1,2-benzisoxazol-3-yl)piperidin-1-yl)ethyl)-4,5,6,7-tetrahydro-2-methylthieno[2,3-c]pyridine as an oil, m.p. 167°–172° C. as oxalate thereof.

EXAMPLE 53

A mixture of 210 mg of 6-acetyl-3-(2-bromoethyl)-4,5,6,7-tetrahydro-2-methylthieno[2,3-c]pyridine, 200 mg of 4-(6-fluorobenzo(b)thiophen-3-yl)piperidine hydrochloride, 250 mg of potassium carbonate and 140 mg of potassium iodide in 5 ml of dimethylformamide and 5 ml of toluene was stirred at 90° C. for 22 hours and concentrated in vacuo. To the residue were added ethyl acetate and water, and separated. The ethyl acetate layer was washed with water, dried over magnesium sulfate and concentrated in vacuo. The residue was purified by column chromatography on a silica gel to give 160 mg of 6-acetyl-3-(2-(4-(6-fluorobenzo(b)thiophen-3-yl)piperidin-1-yl)ethyl)-4,5,6,7-tetrahydro-2-methylthieno[2,3-c]pyridine as an oil.

¹H-NMR(CDCl₃) δ:2.20(s,3H), 2.40(s,3H), 3.10(m,2H), 1.8–2.8 (m,13H), 3.75(m,2H), 4.60(d,2H), 7.02(s,1H), 7.10 (dt,1H), 7.50 (dd,1H), 7.70(dd,1H) m.p. 223°–225° C. as oxalate thereof.

EXAMPLE 54

A mixture of 514 mg of 6-acety-3-(2-bromoethyl)-4,5,6,7-tetrahydro-2-methylthieno[2,3-c]pyridine, 511 mg of 4-(6-fluoro-1H-indazol-3-yl)piperidine hydrochloride, 690 mg of potassium carbonate and 365 mg of potassium iodide in 10 ml of dimethylformamide and 10 ml of toluene was stirred at 90° C. for 22 hours and concentrated in vacuo. To the residue were added ethyl acetate and water, and separated. The ethyl acetate layer was washed with water, dried over magnesium sulfate and concentrated in vacuo. The residue was purified by column chromatography on a silica gel and recrystallized from the mixture of diisopropyl ether and isopropyl alcohol to give 170 mg of 6-acetyl-3-(2-(4-(6-fluoro-1H-indazol-3-yl)piperidin-1-yl)ethyl-4,5,6,7-tetrahydro-2-methylthieno[2,3-c]pyridine monohydrate, m.p. 116°–119° C.

EXAMPLE 55

A mixture of 590 mg of 6-acetyl-3-(2-bromoethyl)-4,5,6,7-tetrahydro-2-methylthieno[2,3-c]pyridine, 580 mg of 4-(6-fluoro-1-methyl-1H-indazol-3-yl) piperidine, 780 mg of potassium carbonate and 415 mg of Potassium iodide in 10 ml of dimethylformamide and 10 ml of toluene was stirred at 90° C. for 22 hours and concentrated in vacuo. To the residue were added ethyl acetate and water, and separated. The ethyl acetate layer was washed with water, dried over magnesium sulfate and concentrated in vacuo. The residue was purified by column chromatography on a silica gel to give 540 mg of 6-acetyl-3-(2-(4-(6-fluoro-1-methyl-1H-indazol-3-yl)piperidin-1-yl) ethyl)-4,5,6,7-tetrahydro-2-methylthieno[2,3-c]pyridine as an oil, m.p. 213°–216° C. as oxalate thereof.

EXAMPLE 56

To a solution of 2 g of 4,5,6,7-tetrahydro-5H-thieno[2,3-c]azepin-8-one and 2 g of chloroacetyl chloride in 25 ml of dichloromethane was added 4.8 g of aluminum chloride. The mixture was stirred for 30 minutes, refluxed under heating for an hour and then poured into water. The precipitated crystals were collected by filtration and washed with isopropyl alcohol to give 2 g of 2-chloroacetyl-4,5,6,7-tetrahydro-8H-thieno[2,3-c]azepin-8-one, m.p. 221°–223° C. (decomposition).

EXAMPLE 57

A mixture of 1.9 g of 2-chloroacetyl-4,5,6,7-tetrahydro-8H-thieno[2,3-c]azepin-8-one in 5.4 ml of triethylsilane and 15 ml of trifluoroacetic acid was stirred at 50° C. for 12 hours. The mixture was poured into water, alkali fled and extracted with ethyl acetate. The exract was washed with water, dried and concentrated. The residue was purified by column chromatography on a silica gel to give 0.85 g of 2-chloroethyl-4,5,6,7-tetrahydro-8H-thieno[2,3-c]azepin-8-one as white crystals, m.p. 156°–158° C.

EXAMPLE 58

A mixture of 800 mg of 2-chloroethyl-4,5,6,7-tetrahydro-8H-thieno[2,3-c]azepin-8-one, 920 mg of 4-(6-fluoro-1,2-benzisoxazol-3-yl)piperidine hydrochloride, 1.45 g of potassium carbonate and 580 mg of potassium iodide in 10 ml of dimethylformamide and 10 ml of toluene was stirred at 90° C. for 22 hours and concentrated in vacuo. To the residue were added ethyl acetate and water, and separated. The ethyl acetate layer was washed with water, dried over magnesium sulfate and concentrated in vacuo. The residue was purified by column chromatography on a silica gel and recrystallized from ethyl acetate to give 0.65 g of 2-(2-(4-(6-fluoro-1,2-benzisoxazol-3-yl)piperidin-1-yl)ethyl)-4,5,6,7-tetrahydro-8H-thieno[2,3-c]azepin-8-one, m.p. 192°–194° C.

EXAMPLE 59

To a solution of 2 g of 4,5,6,7-tetrahydro-8H-thieno[2,3-c]azepin-8-one and 2.5 g of 4-chlorobutyryl chloride in 25 ml of dichloromethane was added 4.8 g of aluminum chloride under cooling. The mixture was stirred for 80 minutes, refluxed under heating and poured into water, and then extracted with chloroform. The extract was washed with water, dried over magnesium sulfate and concentrated. The residue was crystallized from ethyl acetate-isopropyl ether to give 1.2 g of 2-(4-chlorobutyryl)-4,5,6,7-tetrahydro-8H-thieno[2,3-c]azepin-8-one as white crystals, m.p. 163°14 165° C.

EXAMPLE 60

A mixture of 1.1 g of 2-(4-chlorobutyryl)-4,5,6,7-tetrahydro-8H-thieno[2,3-c]azepin-8-one, 1.1 g of 4-(6-fluoro-1,2-benzisoxazol-3-yl)piperidine hydrochloride, 1.68 g of potassium carbonate and 670 mg of potassium iodide in 10 ml of dimethylformamide and 10 ml of toluene was stirred at 90° C. for 22 hours and concentrated in vacuo. To the residue were added ethyl acetate and water, and separated. The ethyl acetate layer was washed with water, dried over magnesium sulfate and concentrated in vacuo. The residue was purified by column chromatography on a silica gel and recrystallized from ethyl acetate-isopropyl ether to give 0.55 g of 2-(4-(4-(6-fluoro-1,2-benzisoxazol-3-yl)piperidin-1-yl)butyryl)-4,5,6,7-tetrahydro-8H-thieno[2,3-c]azepin-8-one ½hydrate, m.p. 186°–187° C.

EXAMPLE 61

To a mixture of 6.7 g of 4,5,6,7-tetrahydro-8H-thieno[2,3-c]azepin-8-one and 4.5 g of sodium borohydride in 70 ml of tetrahydrofuran was added boron trifluoride-ether complex dropwise under ice-cooling and the mixture was refluxed under heating for an hour. The mixture was poured into water, washed with chloroform, made alkaline with 10% potassium hydroxide solution and extracted with chloroform. The extract was washed with water, dried and concentrated to give 4.1 g of 5,6,7,8-tetrahydro-4H-thieno[2,3-c]azepine as an oil.

EXAMPLE 62

To a mixture of 4 g of 5,6,7,8-tetrahydro-4H-thieno[2,3-c]azepine and 4 g of pyridine in 20 ml of chloroform was added 4.1 g of acetic anhydride under ice-cooling and the mixture was stirred at room temperature for an hour. The mixture was poured into water and extracted with chloroform. The extract was washed with water, dried and concentrated to give 4 g of 7-acetyl-5,6,7,8-tetrahydro-4H-theino[2,3-c]azepine as an oil.

EXAMPLE 63

To a solution of 2 g of 7-acetyl-5,6,7,8-tetrahydro-4H-thieno[2,3-c]azepine and 1.7 g of chloroacetyl chloride in 25 ml of dichloromethane was added 4.8 g of aluminum chloride under ice-cooling. The mixture was stirred for 30 minutes and refluxed under heating for an hour. The mixture was poured into water and extracted with chloroform. The extract was washed with water, dried over magnesium sulfate and concentrated to give 2.2 g of 7-acetyl-2-chloroacetyl-5,6,7,8-tetrahydro-4H-thieno[2,3-c]azepine as an oil.

EXAMPLE 64

A mixture of 2.1 g of 7-acetyl-2-chloroacetyl-5,6,7,8-tetrahydro-4H-thieno[2,3-c]azepine in 5.4 ml of triethylsilane and 15 ml of trifluoroacetic acid was stirred at room temperature for 12 hours. The mixture was poured into water, made alkaline and extracted with ethyl acetate. The exract was washed with water, dried and concentrated. The residue was purified by column chromatography on a silica gel to give 1.8 g of 7-acetyl-2-chloroethyl-5,6,7,8-tetrahydro-4H-thieno[2,3-c]azepine as an oil.

EXAMPLE 65

A mixture of 1.6 g of 7-acetyl-2-chloroethyl-5,6,7,8-tetrahydro-4H-thieno[2,3-c]azepine, 1.8 g of 4-(6-fluoro-1,2-benzisoxazol-3-yl)-piperidine hydrochloride, 2.6 g of potassium carbonate and 1 g of potassium iodide in 15 ml of dimethylformamide and 15 ml of toluene was stirred at 90° C. for 5 hours and concentrated in vacuo. To the residue were added ethyl acetate and water, and separated. The ethyl acetate layer was washed with water, dried over magnesium sulfate and concentrated in vacuo. The residue was purified by column chromatograhy on a silica gel to give 1.5 g of 7-acetyl-2-(2-(4-(6-fluoro-1,2-benzisoxazol-3-yl)piperidin-1-yl)ethyl)-5,6,7,8-tetrahydro-4H-thieno[2,3-c]azepine as an oil. The oil was treated with hydrochloric acid in isopropyl alcohol and recrystallized from ethanol-isopropyl ether to give 7-acetyl-2-(2-(4-(6-fluoro-1,2-benzisoxazol-3-yl) piperidin-1-yl)ethyl)-5,6,7,8-tetrahydro-4H-thieno[2,3-c] azepine hydrochloride 3/2hydrate, m.p. 210° C. (decomposition).

EXAMPLE 66

To a solution of 2.5 g of 7-acetyl-5,6,7,8-tetrahydro-4H-thieno-[2,3-c]azepine and 2.7 g of 4-chlorobutyryl chloride in 25 ml of dichloromethane was added 6.0 g of aluminum chloride under ice-cooling. The mixture was stirred for 30 minutes, poured into water and extracted with chloroform. The extract was washed with water, dried over magnesium sulfate and concentrated. The residue was purified by column chromatography on a silica gel to give 2.9 g of 7-acetyl-2-(4-chlorobutyryl)-5,6,7,8-tetrahydro-4H-thieno [2,3-c]azepine as an oil.

EXAMPLE 67

A mixture of 2.8 g of 7-acetyl-2-(4-chlorobutyryl)-5,6,7, 8-tetrahydro-4H-thieno[2,3-c]azepine, 2.6 g of 4-(6-fluoro-1,2-benzisoxazol-3-yl)piperidine hydrochloride, 3.9 g of potassium carbonate and 1.55 g of potassium iodide in 30 ml of dimethylformamide and 30 ml of toluene was stirred at 70° C. for 20 hours and concentrated in vacuo. To the residue were added ethyl acetate and water, and separated. The ethyl acetate layer was washed with water, dried over magnesium sulfate and concentrated in vacuo. The residue was purified by column chromatography on a silica gel to give 3.0 g of 7-(acetyl-2-(4-(4-(6-fluoro-1,2-benzisoxazol-3-yl) piperidin-1-yl)butyryl)-5,6,7,8-tetrahydro-4H-thieno[2,3-c] azepine as an oil. The oil was treated with hydrochloric acid in isopropyl alcohol and recrystallized from ethanol-ethyl acetate to give 7-acetyl-2-(4-(4-(6-fluoro-1,2-benzisoxazol-3-yl)piperidin-1-yl)butyryl)-5,6,7,8-tetrahydro-4H-thieno[2,3-c]azepin hydrochloride, m.p. 230° C. (decomposition).

EXAMPLE 68

The reaction and procedure were conducted in a similar manner as in Example 24 using 1.6 g of 5-acetyl-3-(4-chlorobutyryl)-4,5,6,7-tetrahydro-2-methylthieno[3,2-c] pyridine and 1.4 g of 4-(6-fluoro-1,2-benzisoxazol-3-yl) piperidine hydrochloride to give 0.6 g of 5-acetyl-3-(4-(4-(6-fluoro-1,2-benzisoxazol-3-yl)piperidin-1-yl)butyryl)-4,5, 6,7-tetrahydro-2-methylthieno[3,2-c]pyridine as an oil, m.p. 116°–118° C. as an oxalate monohydrate thereof.

EXAMPLE 69

The reaction and procedure were conducted in a similar manner as in Example 14 using 1.0 g of 6-acetyl-3-(2-chloroethyl)-4,5,6,7-tetrahydro-2-methylthieno[2,3-c] pyridine and 0.88 g of 1-(1,2-benzoisothiazol-3-yl) piperazine to give 1.0 g of 6-acetyl-3-(2-(4-(1,2-benzisothiazol-3-yl)piperazin-1-yl)ethyl)-4,5,6,7-tetrahydro-2-methylthieno[2,3-c]pyridine as an oil, m.p. 190°–192° C. (decomposition) as an oxalate ½hydrate thereof.

EXAMPLE 70

The reaction and procedure were conducted in a similar manner as in Example 24 using 0.9 g of 6-acetyl-2-(2-chloroethyl)-4,5,6,7-tetrahydrothieno[2,3-c]pyridine and 1.0 g of 4-(5-chloro-1,2-benzisoxazol-3-yl)piperidine hydrochloride to give 0.7 g of 6-acetyl-2-(2-(4-(5-chloro-1, 2-benzisoxazol-3-yl)piperidin-1-yl)ethyl)-4,5,6,7-tetrahydrothieno[2,3-c]pyridine as an oil, m.p. 122°–124° C. (decomposition) as a hydrochloride thereof.

EXAMPLE 71

The reaction and procedure were conducted in a similar manner as in Example 24 using 0.2 g of 6-acetyl-3-(2-chloroethyl)-4,5,6,7-tetrahydro-2-methylthieno[2,3-c] pyridine and 0.2 g of 1-(6-chlorobenzothiazol-2-yl) piperazine to give 0.04 g of 6-acetyl-3-(2-(4-(6-chlorobenzothiazol-2-yl)piperazin-1-yl)ethyl)-4,5,6,7-tetrahydro-2-methylthieno[2,3-c]pyridine as an oil, m.p. 180° C. (decomposition) as an oxalate thereof.

EXAMPLE 72

The reaction and procedure were conducted in a similar manner as in Example 24 using 2.0 g of 5-acetyl-3-(2-chloroethyl)-4,5,6,7-tetrahydro-2-methylthieno[3,2-c] pyridine and 1.0 g of 4-(6-fluoro-1,2-benzisoxazol-3-yl) piperidine hydrochloride to give 0.25 g of 5-acetyl-3-(2-(4-(6-fluoro-1,2-benzisoxazol-3-yl)piperidin-1-yl)ethyl)-4,5,6, 7-tetrahydro-2-methylthieno[3,2-c]pyridine as an oil, m.p. 198°–200° C. (decomposition) as an oxalate thereof.

EXAMPLE 73

The reaction and procedure were conducted in a similar manner as in Example 24 using 0.7 g of 6-acetyl-2-(2-chloroethyl)-3-ethyl-4,5,6,7-tetrahydrothieno[2,3-c] pyridine and 0.67 g of 4-(6-fluoro-1,2-benzisoxazol-3-yl) piperidine hydrochloride to give 0.5 g of 6-acetyl-2-(2-(4-(6-fluoro-1,2-benzisoxazol-3-yl)piperidin-1-yl)ethyl)-3-ethyl-4,5,6,7-tetrahydrothieno[2,3-c]pyridine as an oil, m.p. 165°–167° C. (decomposition) as hydrochloride dihydrate thereof.

EXAMPLE 74

The reaction and procedure were conducted in a similar manner as in Example 24 using 1.8 g of 5-acetyl-2-(4-chlorobutyryl)-4,5,6,7-tetrahydrothieno[3,2-c]pyridine and 1.6 g of 4-(6-fluoro-1,2-benzisoxazol-3-yl)piperidine hydrochloride to give 1.0 g of 5-acetyl-2-(4-(4-(6-fluoro-1,2-benzisoxazol-3-yl)piperidin-1-yl)butyryl)-4,5,6,7-tetrahydro-thieno[3,2-c]pyridine as an oil, m.p. 235° C. as hydrochloride ½hydrate thereof.

EXAMPLE 75

The reaction and procedure were conducted in a similar manner as in Example 24 using 1.1 g of 2-(4-chlorobutyryl) -5,6,7,8-tetrahydro-4H-thieno[3,2-c]azepin-4-one and 1.0 g of 4-(6-fluoro-1,2-benzisoxazol-3-yl)piperidine hydrochloride to give 0.21 g of 2-(4-(4-(6-fluoro-1,2-benzisoxazol-3-yl)piperidin-1-yl)butyryl)-5,6,7,8-tetrahydro-4H-thieno[3, 2-c]azepin-4-one, m.p. 142°–143° C.

EXAMPLE 76

To a solution of 0.4 g of 3-(2-(4-(6-fluoro-1,2-benzisoxazol-3-yl)piperidin-1-yl)acetyl)-2-methyl-5,6,7,8-tetrahydro-4H-thieno[3,2-c]azepin-4-one (m.p. 175°–176° C. as oxalate thereof) in 20 ml of methanol was added 0.5 g of sodium borohydride under cooling. The mixture was stirred for 10 minutes and concentrated. Water was added thereto and the solution was extracted with ethyl acetate. The extract was washed with water, dried and the solvent was distilled away. The residue was treated with fumaric acid in ethanol and recrystallized from ethanol to give 0.22 g of 3-(2-(4-(6-fluoro-1,2-benzisoxazol-3-yl)piperidin-1-yl) -1-hydroxyethyl)-2-methyl-5,6,7,8-tetrahydro-4H-thieno[3, 2-c]azepin-4-one difumarate monohydrate, m.p. 116°–118° C.

EXAMPLE 77

The reaction and procedure were conducted in a similar manner as in Example 24 using 0.5 g of 6-acetyl-3-bromo-2-(2-chloroethyl)-4,5,6,7-tetrahydrothieno[2,3-c]pyridine and 0.4 g of 4-(6-fluoro-1,2-benzisoxazol-3-yl)piperidine hydrochloride to give 0.05 g of 6-acetyl-3-bromo-2-(2-(4-(6-fluoro-1,2-benzisoxazol-3-yl)piperidin-1-yl)ethyl)-4,5,6, 7-tetrahydrothieno[2,3-c]pyridine as an oil, m.p. 114°–117° C. as an oxalate thereof.

EXAMPLE 78

The reaction and procedure were conducted in a similar manner as in Example 24 using 0.5 g of 2-(2-chloroethyl)-4,6,7,8-tetrahydro-5H-thieno[3,2-b]azepin-5-one and 0.5 g of 4-(6-fluorobenzo(b)thiophen-3-yl)piperidine hydrochloride to give 0.2 g of 2-(2-(4-(6-fluorobenzo(b)thiophen-3-yl)piperidin-1-yl)ethyl)-4,6,7,8-tetrahydro-5H-thieno[3,2-b] azepin-5-one, m.p. 191°–193° C.

EXAMPLE 79

The reaction and procedure are conducted in a similar manner as in Example 24 using 6-acetyl-3-(2-chloroethyl)-

4,5,6,7-tetrahydro-2-ethylthieno[2,3-c]pyridine and 4-(6-fluorobenzo(b)thiophen-3-yl)piperidine hydrochloride to give 6-acetyl-3-(2-(4-(6-fluorobenzo(b)thiophen-3-yl) piperidin-1-yl)ethyl)-4,5,6,7-tetrahydro-2-ethylthieno[2,3-c]pyridine.

EXAMPLE 80

The reaction and procedure are conducted in a similar manner as in Example 24 using 6-acetyl-2-(4-chlorobutyryl)-4,5,6,7-tetrahydrothieno[2,3-c]pyridine and 4-(6-fluorobenzo(b)thiophen-3-yl)piperidine hydrochloride to give 6-acetyl-2-(4-(4-(6-fluorobenzo(b)thiophen-3-yl) piperidin-1-yl)butyryl)-4,5,6,7-tetrahydrothieno[2,3-c] pyridine.

EXAMPLE 81

The reaction and procedure are conducted in a similar manner as in Example 24 using 6-acetyl-2-(2-chloroethyl)-4,5,6,7-tetrahydro-3-methylthieno[2,3-c]pyridine and 4-(6-fluorobenzo(b)thiophen-3-yl)piperidine hydrochloride to give 6-acetyl-2-(2-(4-(6-fluorobenzo(b)thiophen-3-yl) piperidin-1-yl)ethyl)-4,5,6,7-tetrahydro-3-methylthieno[2,3-c]pyridine.

EXAMPLE 82

A mixture of 0.5 g of 2-((3-chloropropyl)thio)-4-oxo-4,5,6,7-tetrahydrobenzo(b)thiophene, 0.5 g of 4-(6-fluoro-1,2-benzisoxazol-3-yl)piperidine hydrochloride, 0.6 g of potassium carbonate and 0.4 g of potassium iodide in 10 ml of dimethylformamide and 10 ml of toluene was mixed at 100° C. for 4 hours and poured into water. The toluene layer was washed with water, dried over magnesium sulfate and concentrated. The residue was purified by column chromatography on a silica gel to give 0.5 g of 2-(3-(4-(6-fluoro-1,2-benzisoxazol-3-yl)piperidin-1-yl)propylthio)-4-oxo-4,5,6,7-tetrahydrobenzo(b)-thiophene. The resulting compound was dissolved in 20 ml of ethanol, and 0.1 g of hydroxylamine hydrochloride and 0.12 g of sodium hydrogencarbonate were added thereto. After the mixture was refluxed for 3 hours, the solvent was distilled away in vacuo and water was added to the residue, and then extracted with ethyl acetate. The extract was washed with water, dried over magnesium sulfate and concentrated. To the residue was added isopropyl ether to give 0.5 g of an oxime compound as crystals. A mixture of 0.35 g of the oxime compound and 3.5 g of 115% polyphosphoric acid was stirred at 100° C. for 5 hours, poured into water and extracted with chloroform. The extract was washed with water, dried and concentrated. The residue was separated and purified by column chromatography on a silica gel and each of resulting crystals was recrystallized from isopropyl ether to give 0.06 g of 2-(3-(4-(6-fluoro-1,2-benzisoxazol-3-yl)piperidin-1-yl) propylthio)-5,6,7,8-tetrahydro-4H-thieno[3,2-c]azepin-4-one, m.p. 119°–121° C. and 0.019 g of 2-(3-(4-(6-fluoro-1,2-benzisoxazol-3-yl)piperidin-1-yl)propylthio)-4,6,7,8-tetrahydro-5H-thieno[3,2-b]azepin-5-one, m.p. 125°–127° C.

EXAMPLE 83

A mixture of 1.0 g of 2-(2-chloroethyl)-3-ethyl-4,6,7,8-tetrahydro-5H-thieno[3,2-b]azepin- 5-one, 1.0 g of 4-(6-fluoro-1,2-benzisoxazol-3-yl)piperidine hydrochloride, 4.0 g of potassium carbonate and 1.5 g of potassium iodide in 25 ml of dimethylformamide and 25 ml of toluene was stirred at 100° C. for 3 hours and poured into water. The toluene layer was washed with water, dried over magnesium sulfate and concentrated. The residue was purified by column chromatography on a silica gel and recrystallized from isopropyl alcohol to give 0.45 g of 3-ethyl-2-(2-(4-(6-fluoro-1,2-benzisoxazol-3-yl)piperidin-1-yl)ethyl)-4,6,7,8-tetrahydro-5H-thieno[3,2-b]azepin-5-one ¾hydrate, m.p. 115°–117° C.

EXAMPLE 84

A mixture of 0.7 g of 6-acetyl-2-(2-chloroethyl)-3-ethyl-4,5,6,7-tetrahydrothieno[2,3-c]pyridine, 0.7 g of 4-(6-fluorobenzo(b)thiophen-3-yl)piperidine hydrochloride, 1.8 g of potassium carbonate and 0.6 g of potassium iodide in 25 ml of dimethylformamide and 25 ml of toluene was stirred at 70° C. for 7 hours and poured into water. The toluene layer was washed with water, dried over magnesium and concentrated. The residue was purified by column chromatography on a silica gel and dissolved in ethanol to convert hydrochloride thereof, and then recrystallized from methanol to give 0.45 g of 6-acetyl-3-ethyl-2-(2-(4-(6-fluorobenzo-(b) thiophen-3-yl)piperidin-1-yl)ethyl)-4,5,6,7-tetrahydrothieno[2,3-c]pyridine hydrochloride, m.p. 240° C. (decomposition).

EXAMPLE 85

A mixture of 1.0 g of 6-acetyl-2-(2-chloroethyl)-3-ethyl-4,5,6,7-tetrahydrothieno[2,3-c]pyridine, 0.95 g of 4-(6-fluorobenzo(b)furan-3-yl)piperidine hydrochloride, 3.0 g of potassium carbonate and 1.0 g of potassium iodide in 25 ml of dimethylformamide and 25 ml of toluene was stirred at 70° C. for 7 hours and poured into water. The toluene layer was washed with water, dried over magnesium sulfate and concentrated. The residue was purified by column chromatography on a silica gel and dissolved in ethanol to convert hydrochloride thereof, and then recrystallized from isopropyl alcohol to give 0.5 g of 6-acetyl-3-ethyl-2-(2-(4-(6-fluorobenzo(b)furan-3-yl)piperidin-1-yl)ethyl)-4,5,6,7-tetrahydro-thieno[2,3-c]pyridine hydrochloride, m.p. 205° C. (decomposition).

EXAMPLE 86

A mixture of 0.5 g of 6-acetyl-2-(2-chloroethyl)-3-ethyl-4,5,6,7-tetrahydrothieno[2,3-c]pyridine, 0.5 g of 4-(6-fluoro-1,2-benzisothiazol-3-yl)piperidine hydrochloride, 1.5 g of potassium carbonate and 0.5 g of potassium iodide in 25 ml of dimethylformamide and 25 ml of toluene was stirred at 70° C. for 7 hours and poured into water. The toluene layer was washed with water, dried over magnesium sulfate and concentrated. The residue was purified by column chromatography on a silica gel to give 0.5 g of 6-acetyl-3-ethyl-2-(2-(4-(6-fluoro-1,2-benzisothiazol-3-yl)piperidin-1-yl) ethyl)-4,5,6,7-tetrahydrothieno[2,3-c]pyridine as an oil.

$^1$H-NMR (CDCl$_3$) δ:1.10 (t,3H), 2.00–2.40 (m,4H), 2.20 (d,3H), 2.50 (q,2H), 2.60–2.70 (m,4H), 3.00 (m,2H), 3.15 (m,1H), 3.20 (m,4H), 3.80 (dt,2H), 4.50 (d,2H), 7.20 (dt, 1H), 7.60(dd,1H), 7.95 (dd,1H) m.p. 156°–160° C. as oxalate ⅓ hydrate thereof.

The following compounds can be prepared in a similar manner as the above.

EXAMPLE 87

6-formyl-3-isobutyl-2-(2-(4-(6-fluoro-1,2-benzisoxazol-3-yl)piperidin-1-yl)ethyl)-4,5,6,7-tetrahydrothieno[2,3-c] pyridine oxalate ¼hydrate, m.p. 165°–167° C.

EXAMPLE 88

6-formyl-2-(2-(4-(6-fluoro-1,2-benzisoxazol-3-yl) piperidin-1-yl)ethyl)-4,5,6,7-tetrahydrothieno[2,3-c]

pyridine hydrochloride ½hydrate, m.p. 220° C. (decomposition).

EXAMPLE 89

3-ethyl-6-formyl-2-(2-(4-(6-fluoro-1,2-benzisoxazol-3-yl)piperidin-1-yl)ethyl)-4,5,6,7-tetrahydrothieno[2,3-c]pyridine oxalate ¼hydrate, m.p. 188°–190° C.

EXAMPLE 90

6-acetyl-3-(2-(4-(6-fluorobenzo(b)furan-3-yl)piperidin-1-yl)ethyl)-4,5,6,7-tetrahydro-2-methylthieno[2,3-c]pyridine oxalate ⅓hydrate, m.p. 210°–212° C.

EXAMPLE 91

6-acetyl-3-ethyl-2-(2-(4-(4-fluoro-2-methoxybenzoyl)piperidin-1-yl)ethyl)4,5,6,7-tetrahydrothieno[2,3-c]pyridine oxalate, m.p. 134°–136° C.

EXAMPLE 92

6-acetyl-2-(3-(4-(6-fluoro-1,2-benzisoxazol-3-yl)piperidin-1-yl)propionyl)-4,5,6,7-tetrahydrothieno[2,3-c]pyridine hydrochloride, m.p. 215° C. (decomposition).

EXAMPLE 93

6-acetyl-2-(4-(4-(6-fluoro-1,2-benzisoxazol-3-yl)piperidin-1-yl)butyl)-4,5,6,7-tetrahydrothieno[2,3-c]pyridine oxalate ¼hydrate, m.p. 186°–188° C.

EXAMPLE 94

6-acetyl-2-(3-(4-(6-fluoro-1,2-benzisoxazol-3-yl)piperidin-1-yl)propyl)-4,5,6,7-tetrahydrothieno[2,3-c]pyridine oxalate, m.p. 150°–152° C.

EXAMPLE 95

6-acetyl-2-(2-(4-(6-fluoro-1,2-benzisoxazol-3-yl)piperidin-1-yl)acetyl)-4,5,6,7-tetrahydrothieno[2,3-c]pyridine, m.p. 141°–144° C.

EXAMPLE 96

6-acetyl-3-ethyl-2-(2-(4-(2,4-difluorobenzoyl)piperidin-1-yl)ethyl)-4,5,6,7-tetrahydrothieno[2,3-c]pyridine ½ oxalate ½ hydrate, m.p. 128°–131° C.

EXAMPLE 97

6-acetyl-2-(2-(4-(6-fluoro-1,2-benzisoxazol-3-yl)piperidin-1-yl)ethyl)-4,5,6,7-tetrahydro-3-propylthieno[2,3-c]pyridine fumarate, m.p. 197°–199° C. (decomposition).

EXAMPLE 98

6-acetyl-3-(2-(4-(6-fluoro-1,2-benzisothiazol-3-yl)piperidin-1-yl)ethyl)-4,5,6,7-tetrahydro-2-methylthieno[2,3-c]pyridine 3/2oxalate, m.p. 218° C. (decomposition).

EXAMPLE 99

6-acetyl-3-ethyl-2-(2-(4-(6-fluoro-1H-indazol-3-yl)piperidin-1-yl)ethyl)-4,5,6,7-tetrahydrothieno[2,3-c]pyridine oxalate, m.p. 129°–131° C.

EXAMPLE 100

6-acetyl-3-(1-hydroxyethyl)-2-(2-(4-(6-fluoro-1,2-benzisoxazol-3-yl)piperidin-1-yl)ethyl)-4,5,6,7-tetrahydrothieno[2,3-c]pyridine oxalate monohydrate, m.p. 168°–170° C.

EXAMPLE 101

6-acetyl-3-ethyl-2-(2-(4-(2-acetyl-6-fluorobenzo(b)thiophen-3-yl)piperidin-1-yl)ethyl)-4,5,6,7-tetrahydrothieno[2,3-c]pyridine oxalate, m.p. 232° C. (decomposition).

EXAMPLE 102

6-acetyl-3-ethyl-2-(2-(4-(2-ethyl-6-fluorobenzo(b)thiophen-3-yl)piperidin-1-yl)ethyl)-4,5,6,7-tetrahydrothieno[2,3-c]pyridine $^1$H-NMR(CDCl$_3$)δ:1.10 (t,3H), 1.30 (t,3H), 1.60–2.00 (m,4H), 2.10 (s,3H), 2.20–3.40 (m, 14H), 3.50–3.90 (m, 3H), 4.63 (d,2H), 7.00 (dt,1H), 7.36 (dd,1H), 7.80 (dd,1H).

EXAMPLE 103

6-acetyl-3-ethyl-2-(2-(4-(2-ethyl-6-fluorobenzo(b)furan-3-yl)piperidin-1-yl)ethyl)-4,5,6,7-tetrahydrothieno[2,3-c]pyridine oxalate, m.p. 232° C. (decomposition).

EXAMPLE 104

6-acetyl-3-ethyl-2-(2-(4-(2-methyl-6-fluorobenzo(b)thiophen-3-yl)piperidin-1-yl)ethyl)-4,5,6,7-tetrahydrothieno[2,3-c]pyridine.

EXAMPLE 105

6-acetyl-3-ethyl-2-(2-(4-(2-methyl-6-fluorobenzo(b)furan-3-yl)piperidin-1-yl)ethyl)-4,5,6,7-tetrahydrothieno[2,3-c]pyridine hydrochloride dihydrate, m.p. 205° C. (decomposition).

EXAMPLE 106

5-acetyl-3-ethyl-2-(2-(4-(2-ethyl-6-fluorobenzo(b)thiophen-3-yl)piperidin-1-yl)ethyl)-4,5,6,7-tetrahydrothieno[3,2-c]pyridine.

EXAMPLE 107

6-acetyl-3-ethyl-2-(2-(4-(1,2-benzisoxazol-3-yl)piperidin-1-yl)ethyl)-4,5,6,7-tetrahydrothieno[2,3-c]pyridine oxalate monohydrate, m.p. 152°–155° C.

EXAMPLE 108

6-acetyl-3-ethyl-2-(2-(4-(4-fluorobenzoyl)piperidin-1-yl)ethyl)-4,5,6,7-tetrahydrothieno[2,3-c]pyridine.

EXAMPLE 109

6-acetyl-3-ethyl-2-(2-(4-(6-methoxybenzo(b)furan-3-yl)piperidin-1-yl)ethyl)-4,5,6,7-tetrahydrothieno[2,3-c]pyridine.

EXAMPLE 110

6-acetyl-3-ethyl-2-(2-(4-(6-hydroxybenzo(b)furan-3-yl)piperidin-1-yl)ethyl)-4,5,6,7-tetrahydrothieno[2,3-c]pyridine.

EXAMPLE 111

5-acetyl-3-ethyl-2-(2-(4-(2-methyl-6-fluorobenzo(b)thiophen-3-yl)piperidin-1-yl)ethyl)-4,5,6,7-tetrahydrothieno[3,2-c]pyridine.

EXAMPLE 112

5-acetyl-3-ethyl-2-(2-(4-(2-methyl-6-fluorobenzo(b)furan-3-yl)piperidin-1-yl)ethyl-4,5,6,7-tetrahydrothieno[3,2-c]pyridine.

EXAMPLE-113

5-acetyl-3-ethyl-2-(2-(4-(6-fluoro-1,2-benzisoxazol-3-yl) piperidin-1-yl)ethyl)-4,5,6,7-tetrahydrothieno[3,2-c] pyridine.

EXAMPLE 114

5-acetyl-3-ethyl-2-(2-(4-(6-fluoro-1,2-benzisothiazol-3-yl)piperidin- 1-yl)ethyl)-4,5,6,7-tetrahydrothieno[3,2-c] pyridine.

EXAMPLE 115

5-acetyl-3-ethyl-2-(2-(4-(1,2-benzisoxazol-3-yl) piperidin-1-yl)ethyl)-4,5,6,7-tetrahydrothieno[3,2-c] pyridine.

EXAMPLE 116

5-acetyl-3-ethyl-2-(2-(4-(2-ethyl-6-fluorobenzo(b)furan-3-yl)piperidin-1-yl)ethyl-4,5,6,7-tetrahydrothieno[3,2-c] pyridine.

EXAMPLE 117

5-acetyl-3-ethyl-2-(2-(4-(4-fluorobenzoyl)piperidin-1-yl) ethyl)-4,5,6,7-tetrahydrothieno[3,2-c]pyridine.

EXAMPLE 118

5-acetyl-3-ethyl-2-(2-(4-(6-methoxybenzo(b)furan-3-yl) piperidin-1-yl)ethyl)-4,5,6,7-tetrahydrothieno[3,2-c] pyridine.

EXAMPLE 119

5-acetyl-3-ethyl-2-(2-(4-(6-hydroxybenzo(b)furan-3-yl) piperidin-1-yl)ethyl)-4,5,6,7-tetrahydrothieno[3,2-c] pyridine.

EXAMPLE 120

5-acetyl-3-ethyl-2-(2-(4-(5-fluoro-1,2-benzisoxazol-3-yl) piperidin-1-yl)ethyl)-4,5,6,7-tetrahydrothieno[3,2-c] pyridine.

EXAMPLE 121

5-acetyl-3-ethyl-2-(2-(4-(5-chloro-1,2-benzisoxazol-3-yl)piperidin-1-yl)ethyl)-4,5,6,7-tetrahydrothieno[3,2-c] pyridine.

EXAMPLE 122

5-acetyl-3-ethyl-2-(2-(4-(benzo(b)furan-2-yl)piperidin-1-yl)ethyl-4,5,6,7-tetrahydrothieno[3,2-c]pyridine.

EXAMPLE 123

5-acetyl-3-ethyl-2-(2-(4-(benzo(b)thiophen-2-yl) piperidin-1-yl)ethyl)-4,5,6,7-tetrahydrothieno[3,2-c] pyridine.

EXAMPLE 124

5-acetyl-3-ethyl-2-(2-(4-(6-fluorobenzo(b)furan-2-yl) piperidin-1-yl)ethyl)-4,5,6,7-tetrahydrothieno[3,2-c] pyridine hydrochloride, m.p. 218° C. (decomposition).

EXAMPLE 125

5-acetyl-3-ethyl-2-(2-(4-(6-fluorobenzo(b)thiophen-2-yl) piperidin-1-yl)ethyl)-4,5,6,7-tetrahydrothieno[3,2-c] pyridine.

EXAMPLE 126

5-acetyl-3-ethyl-2-(2-(4-(7-bromo-5-methoxybenzo(b) furan-2-yl)piperidin-1-yl)ethyl)-4,5,6,7-tetrahydrothieno[3, 2-c]pyridine.

EXAMPLE 127

6-acetyl-3-ethyl-2-(2-(4-(benzo(b)furan-2-yl)piperidin-1-yl)ethyl)-4,5,6,7-tetrahydrothieno[2,3-c]pyridine.

EXAMPLE 128

6-acetyl-3-ethyl-2-(2-(4-(benzo(b)thiophen-2-yl) piperidin-1-yl)ethyl)-4,5,6,7-tetrahydrothieno[2,3-c] pyridine.

EXAMPLE 129

6-acetyl-3-ethyl-2-(2-(4-(6-fluorobenzo(b)furan-2-yl) piperidin-1-yl)ethyl)-4,5,6,7-tetrahydrothieno[2,3-c] pyridine.

EXAMPLE 130

6-acetyl-3-ethyl-2-(2-(4-(6-fluorobenzo(b)thiophen-2-yl) piperidin-1-yl)ethyl)-4,5,6,7-tetrahydrothieno[2,3-c] pyridine.

EXAMPLE 131

6-acetyl-3-ethyl-2-(2-(4-(7-bromo-5-methoxybenzo(b) furan-2-yl)piperidin- 1-yl)ethyl)-4,5,6,7-tetrahydrothieno[2, 3-c]pyridine.

EXAMPLE 132

6-acetyl-3-ethyl-2-(2-(4-(6,7-difluoro-1,2-benzisoxazol-3-yl)piperidin-1-yl)ethyl)-4,5,6,7-tetrahydrothieno[2,3-c] pyridine.

EXAMPLE 133

6-acetyl-3-ethyl-2-(2-(4-(5,6-difluoro-1,2-benzisoxazol-3-yl)piperidin-1-yl)ethyl)-4,5,6,7-tetrahydrothieno[2,3-c] pyridine.

EXAMPLE 134

6-acetyl-3-ethyl-2-(2-(4-(6-methyl-1,2-benzisoxazol-3-yl)piperidin-1-yl)ethyl)-4,5,6,7-tetrahydrothieno[2,3-c] pyridine.

EXAMPLE 135

6-acetyl-3-ethyl-2-(2-(4-(6-hydroxy-1,2-benzisoxazol-3-yl)piperidin-1-yl)ethyl)-4,5,6,7-tetrahydrothieno[2,3-c] pyridine.

EXAMPLE 136

6-acetyl-3-ethyl-2-(2-(4-(6,7-dihydroxy-1,2-benzisoxazol-3-yl)piperidin-1-yl)ethyl)-4,5,6,7-tetrahydrothieno[2,3-c]pyridine.

EXAMPLE 137

6-acetyl-3-ethyl-2-(2-(4-(5,6-dihydroxy-1,2-benzisoxazol-3-yl)piperidin-1-yl)ethyl)-4,5,6,7-tetrahydrothieno[2,3-c]pyridine.

EXAMPLE 138

N-ethyl-3-ethyl-2-(2-(4-(6-fluoro-1,2-benzisoxazol-3-yl) piperidin-1-yl)ethyl)-4,5,6,7-tetrahydrothieno[2,3-c] pyridine-6-carboxamide oxalate ½hydrate, m.p. 159°–162° C.

EXAMPLE 139

6-acetyl-3-ethyl-2-(2-(4-(6-fluoro-1,1-dioxobenzo(b) thiophen-3-yl)piperidin-1-yl)ethyl)-4,5,6,7-tetrahydrothieno[2,3-c]pyridine hydrochloride dihydrate, m.p. 240° C. (decomposition).

EXAMPLE 140

3-ethyl-2-(2-(4-(6-fluorobenzo(b)furan-3-yl)piperidin-1-yl)ethyl)-4,5,6,7-tetrahydrothieno[2,3-c]pyridine dihydrochloride ¼hydrate, m.p. 240°–243° C.

EXAMPLE 141

6-acetyl-3-ethyl-2-(2-(4-(6-methoxy-1,2-benzisoxazol-3-yl)piperidin-1-yl)ethyl)-4,5,6,7-tetrahydrothieno[2,3-c]pyridine.

EXAMPLE 142

3-ethyl-2-(2-(4-(6-fluorobenzo(b)furan-3-yl)piperidin-1-yl)ethyl)-4,6,7,8-tetrahydro-5H-thieno[3,2-b]azepin-5-one.

EXAMPLE 143

3-ethyl-2-(2-(4-(6-fluorobenzo(b)furan-3-yl)piperidin-1-yl)ethyl)-4,6,7,8-tetrahydro-5H-4-methylthieno[3,2-b]azepin-5-one.

EXAMPLE 144

3-ethyl-2-(2-(4-(6-fluorobenzo(b)furan-3-yl)piperidin-1-yl)ethyl)-4,5,6,7-tetrahydro-8H-thieno[2,3-c]azepin-8-one.

EXAMPLE 145

A mixture of 5.0 g of 6-acetyl-2-(2-chloroethyl)-3-ethyl-4,5,6,7-tetrahydrothieno[2,3-c]pyridine, 4.9 g of 4-(5-methylbenzo(b)furan-3-yl)piperidine hydrochloride, 2.5 g of potassium carbonate, 3.0 g of potassium iodide, 30 ml of dimethylformamide and 30 ml of toluene was stirred at 70° C. for 7 hours and then poured into water. The toluene layer was washed with water, dried over anhydrous magnesium sulfate and concentrated. The residue was purified by column chromatography on a silica gel and then dissolved into ethanol to make a hydrochloride. The resulting crystals were recrystallized from isopropyl alcohol to give 6-acetyl-3-ethyl-2-(2-(4-(5-methylbenzo(b)-furan-3-yl)piperidin-1-yl) ethyl)-4,5,6,7-tetrahydrothieno[2,3-c]pyridine hydrochloride, m.p. 222°–225° C.

EXAMPLE 146

A mixture of 0.9 g of 6-acetyl-2-(2-chloroethyl)-3-ethyl-4,5,6,7-tetrahydrothieno[2,3-c]pyridine, 1.0 g of 4-(4,6-dichlorobenzo(b)furan-3-yl)piperidine hydrochloride, 0.5 g of potassium carbonate, 0.5 g of potassium iodide, 25 ml of dimethylformamide and 25 ml of toluene was stirred at 80° C. for 6 hours and then poured into water. The toluene layer was washed with water, dried over anhydrous magnesium sulfate and concentrated. The residue was purified by column chromatography on a silica gel and then dissolved into ethanol to make a hydrochloride. The resulting crystals were recrystallized from isopropyl alcohol to give 6-acetyl-2-(2-(4-(4,6-dichlorobenzo(b)furan-3-yl)piperidin-1-yl)ethyl)-3-ethyl-4,5,6,7-tetrahydrothieno[2,3-c]pyridine hydrochloride, m.p. 260° C. (decomposition).

EXAMPLE 147

A mixture of 2.0 g of 2-(2-chloroethyl)-4,6,7,8-tetrahydro-5H-thieno[3,2-b]azepin-5-one, 2.2 g of 4-(6-fluorobenzo(b)furan-3-yl)piperidine hydrochloride, 2.6 g of potassium carbonate, 1.44 g of potassium iodide, 20 ml of dimethylformamide and 20 ml of toluene was stirred at 80° C. for 8 hours and then poured into water. The toluene layer was washed with water, dried over anhydrous magnesium sulfate and concentrated. The residue was recrystallized from ethyl acetate to give 2-(2-(4-(6-fluorobenzo(b)furan-3-yl)piperidin-1-yl)ethyl)-4,6,7,8-tetrahydro-5 H-thieno[3,2-b]azepin-5-one, m.p. 176°–178° C.

EXAMPLE 148

A mixture of 2.0 g of 2-(2-chloroethyl)-4,6,7,8-tetrahydro-5H-thieno[3,2-b]azepin-5-one, 2.1 g of 4-(5-methylbenzo(b)furan-3-yl)piperidine hydrochloride, 2.6 g of potassium carbonate, 1.5 g of potassium iodide, 20 ml of dimethylformamide and 20 ml of toluene was stirred at 80° C. for 8 hours and then poured into water. The toluene layer was washed with water, dried over anhydrous magnesium sulfate and concentrated. The residue was recrystallized from ethyl acetate to give 2-(2-(4-(5-methylbenzo(b)furan-3-yl)piperidin-1-yl)ethyl)-4,6,7,8-tetrahydro-5H-thieno[3,2-b]azepin-5-one, m.p. 156°–158° C.

EXAMPLE 149

6-acetyl-3-ethyl-2-(2-(4-(6-fluoro-1,1-dioxobenzo(b) thiophen-3-yl)piperidin-1-yl)ethyl)-4,5,6,7-tetrahydrothieno[2,3-c]pyridine hydrochloride dihydrate, m.p. 240° C. (decomposition).

EXAMPLE 150

3-ethyl-2-(2-(4-(6-fluoro-1,2-benzoisoxazol-3-yl) piperidin-1-yl)ethyl)-4,5,6,7-tetrahydrothieno[2,3-c] pyridine-6-carboxylic acid ethyl amide oxalate ½ hydrate, m.p. 159°–162° C.

EXAMPLE 151

3-ethyl-2-(2-(4-(6-fluorobenzo(b)furan-3-yl)piperidin-1-yl)ethyl)-4,5,6,7-tetrahydrothieno[2,3-c]pyridine dihydrochloride ¼ hydrate, m.p. 240°–243° C.

EXAMPLE 152

6-acetyl-3-ethyl-2-(2-(4-(6-fluoro-2-methylbenzo(b) furan-3-yl)piperidin-1-yl)ethyl)-4,5,6,7-tetrahydrothieno[2, 3-c]pyridine hydrochloride dihydrate, m.p. 205° C. (decomposition).

EXAMPLE 153

6-acetyl-3-ethyl-2-(2-(4-(1,2-benzoisoxazol-3-yl) piperidin-1-yl)ethyl)-4,5,6,7-tetrahydrothieno[2,3-c] pyridine oxalate monohydrate, m.p. 152°–155° C.

EXAMPLE 154

3-ethyl-2-(2-(4-(6-fluorobenzo(b)furan-3-yl)piperidin-1-yl)ethyl)-4,6,7,8-tetrahydro-5H-thieno[3,2-b]azepin-5-one, m.p. 160°–162° C.

EXAMPLE 155

6-acetyl-3-ethyl-2-(2-(4-(5-chlorobenzo(b)furan-3-yl) piperidin-1-yl)ethyl)-4,5,6,7-tetrahydrothieno[2,3-c] pyridine hydrochloride dihydrate, m.p. 209°–211° C. (decomposition).

EXAMPLE 156

5-acetyl-3-ethyl-2-(2-(4-(5-fluorobenzo(b)furan-3-yl) piperidin-1-yl)ethyl)-4,5,6,7-tetrahydrothieno[3,2-c] pyridine oxalate ½ hydrate, m.p. 148°–151° C.

EXAMPLE 157

6-acetyl-3-ethyl-2-(2-(4-(5-methoxybenzo(b)furan-3-yl) piperidin-1-yl)ethyl)-4,5,6,7-tetrahydrothieno[2,3-c] pyridine oxalate ½ hydrate, m.p. 109°–112° C.

EXAMPLE 158

5-acetyl-3-ethyl-2-(2-(4-(6-fluorobenzo(b)furan-3-yl) piperidin-1-yl)ethyl)-4,5,6,7-tetrahydrothieno[3,2-c] pyridine hydrochloride, m.p. 218° C. (decomposition).

EXAMPLE 159

6-acetyl-3-ethyl-2-(2-(4-(5-bromobenzo(b)furan-3-yl) piperidin-1-yl)ethyl)-4,5,6,7-tetrahydrothieno[2,3-c] pyridine oxalate, m.p. 124°–126° C.

EXAMPLE 160

6-acetyl-3-ethyl-2-(2-(4-(5,6-dimethylbenzo(b)furan-3-yl)piperidin-1-yl)ethyl)-4,5,6,7-tetrahydrothieno[2,3-c] pyridine hydrochloride ¼ hydrate, m.p. 210 C. (decomposition).

EXAMPLE 161

6-acetyl-3-ethyl-2-(2-(4-(bis(4-fluorophenyl)methylene) piperidin-1-yl)ethyl)-4,5,6,7-tetrahydrothieno[2,3-c] pyridine oxalate, m.p. 212°–213° C.

EXAMPLE 162

6-acetyl-3-ethyl-2-(2-(4 -(4-hydroxy-2,6-dimethylbenzoyl)piperidin-1-yl)ethyl)-4,5,6,7-tetrahydrothieno[2,3-c]pyridine oxalate ½ hydrate, m.p. 198°–200° C.

EXAMPLE 163

6-acetyl-3-ethyl-2-(2-(4-(5-chloro-6-methylbenzo(b) furan-3-yl)piperidin-1-yl)ethyl)-4,5,6,7-tetrahydrothieno[3,2-c]pyridine hydrochloride ½ hydrate, m.p. 230° C. or above (decomposition).

EXAMPLE 164

6-acetyl-3-ethyl-2-(2-(4-(5-fluorobenzo(b)furan-3-yl) piperidin-1-yl)ethyl)-4,5,6,7-tetrahydrothieno[2,3-c] pyridine hydrochloride ¼ hydrate, m.p. 200° C. (decomposition).

EXAMPLE 165

3-ethyl-2-(2-(4-(6-fluorobenzo(b)furan-3-yl)piperidin-1-yl)ethyl)- 5,6,7,8-tetrahydrothieno[3,2-c]azepin-4-one hydrochloride, m.p. 260° C. or above (decomposition).

EXAMPLE 166

7-acetyl-3-ethyl-2-(2-(4 -(6-fluorobenzo(b)furan-3-yl) piperidin-1-yl)ethyl)-4,5,6,7-tetrahydro-8H-thieno[2,3-c] azepine hydrochloride monohydrate, m.p. 201°–203° C.

EXAMPLE 167

7-acetyl-3-ethyl-2-(2-(4-(5-chloro-6-methylbenzo(b) furan-3-yl)piperidin-1-yl)ethyl)-4,5,6,7-tetrahydro-8H-thieno[2,3-c]azepine hydrochloride ½ hydrate, m.p. 203°–205° C.

EXAMPLE 168

6-acetyl-3-ethyl-2-(2-(4-(5-methoxybenzo(b)furan-2-yl) piperidin-1-yl)ethyl)-4,5,6,7-tetrahydrothieno[2,3-c] pyridine hydrochloride monohydrate, m.p. 215°–218° C.

EXAMPLE 169

6-acetyl-3-ethyl-2-(4-(4-(6-fluorobenzo(b)furan-3-yl) piperidin-1-yl)butyryl)-4,5,6,7-tetrahydrothieno[2,3-c] pyridine hydrochloride 3/2 hydrate $^1$H-NMR (CDCl$_3$): 1.20–1.40 (m, 3H), 2.05–2.50 (m, 6H), 2.50–3.18 (m, 13H), 3.64–3.92 (m, 5H), 4.60–4.83 (m, 2H), 7.05 (dd, 1H), 7.19 (d, 1H), 7.48 (s, 1H), 7.65–7.80 (b, 1H).

EXAMPLE 170

3,6-diacetyl-2-(2-(4-(6-fluorobenzo(b)furan-3-yl) piperidin-1-yl)ethyl)-4,5,6,7-tetrahydrothieno[2,3-c] pyridine hydrochloride, m.p. 233°–235° C. (decomposition).

EXAMPLE 171

6-acetyl-3-(1-hydroxyethyl)-2-(2-(4-(6-fluorobenzo(b) furan-3-yl)piperidin-1-yl)ethyl)-4,5,6,7-tetrahydrothieno[2, 3-c]pyridine oxalate, m.p. 193°–196° C.

EXAMPLE 172

6-acetyl-3-ethyl-2-(2-(4-(6-methylbenzo(b)furan-3-yl) piperidin-1-yl)ethyl)-4,5,6,7-tetrahydrothieno[2,3-c] pyridine hydrochloride, m.p. 255° C. or above (decomposition).

EXAMPLE 173

6-acetyl-3-ethyl-2-(2-(4-(5-chloro-2-hydroxybenzoyl) piperidin-1-yl)ethyl)-4,5,6,7-tetrahydrothieno[2,3-c] pyridine oxalate monohydrate, m.p. 172°–175° C.

EXAMPLE 174

6-acetyl-3-ethyl-2-(2-(4-(7-methylbenzo(b)furan-3-yl) piperidin-1-yl)ethyl)-4,5,6,7-tetrahydrothieno[2,3-c] pyridine hydrochloride, m.p. 229°–231° C.

EXAMPLE 175

6-acetyl-3-ethyl-2-(2-(4-(5,7-dimethylbenzo(b)furan-3-yl)piperidin-1-yl)ethyl)-4,5,6,7-tetrahydrothieno[2,3-c] pyridine hydrochloride, m.p. 242°–245° C.

EXAMPLE 176

6-acetyl-3-ethyl-4,5,6,7-tetrahydro-2-(2-(4-(4,6-dimethylbenzo(b)furan-3-yl)piperidin-1-yl)ethyl)thieno[2, 3-c]pyridine hydrochloride ¼ hydrate, m.p. 230° C. or above.

EXAMPLE 177

6-acetyl-3-ethyl-4,5,6,7-tetrahydro-2-(2-(4-(2-hydroxy-5-methylbenzoyl)piperidin-1-yl)ethyl)thieno[2,3-c]pyridine fumarate ½ hydrate, m.p. 218°–220° C. (decomposition).

EXAMPLE 178

2-(2-(4-(7-methylbenzo(b)furan-3-yl)piperidin-1-yl) ethyl)-4,6,7,8-tetrahydro-5H-thieno[3,2-b]azepin-5-one, m.p. 188°–190° C.

EXAMPLE 179

2-(2-(4-(benzo(b)furan-3-yl)piperidin-1-yl)ethyl)-4,6,7, 8-tetrahydro-5H-thieno[3,2-b]azepin-5-one.

EXAMPLE 180

2-(2-(4-(4-methylbenzo(b)furan-3-yl)piperidin-1-yl) ethyl)-4,6,7,8-tetrahydro-5H-thieno[3,2-b]azepin-5-one.

EXAMPLE 181

2-(2-(4-(6-methylbenzo(b)furan-3-yl)piperidin-1-yl)ethyl)-4,6,7,8-tetrahydro-5H-thieno[3,2-b]azepin-5-one.

EXAMPLE 182

2-(2-(4-(4-methylbenzo(b)thiophen-3-yl)piperidin-1-yl)ethyl)-4,6,7,8-tetrahydro-5H-thieno[3,2-b]azepin-5-one.

EXAMPLE 183

2-(2-(4-(5-methylbenzo(b)thiophen-3-yl)piperidin-1-yl)ethyl)-4,6,7,8-tetrahydro-5H-thieno[3,2-b]azepin-5-one.

EXAMPLE 184

2-(2-(4-(6-methylbenzo(b)thiophen-3-yl)piperidin-1-yl)ethyl)-4,6,7,8-tetrahydro-5H-thieno[3,2-b]azepin-5-one.

EXAMPLE 185

2-(2-(4-(7-methylbenzo(b)thiophen-3-yl)piperidin-1-yl)ethyl)-4,6,7,8-tetrahydro-5H-thieno[3,2-b]azepin-5-one.

EXAMPLE 186

2-(2-(4-(4-fluorobenzo(b)furan-3-yl)piperazin-1-yl)ethyl)-4,6,7,8-tetrahydro-5H-thieno[3,2-b]azepin-5-one.

EXAMPLE 187

2-(2-(4-(5-fluorobenzo(b)furan-3-yl)piperazin-1-yl)ethyl)-4,6,7,8-tetrahydro-5H-thieno[3,2-b]azepin-5-one.

EXAMPLE 188

2-(2-(4-(6-fluorobenzo(b)furan-3-yl)piperazin-1-yl)ethyl)-4,6,7,8-tetrahydro-5H-thieno[3,2-b]azepin-5-one.

EXAMPLE 189

2-(2-(4-(7-fluorobenzo(b)furan-3-yl)piperazin-1-yl)ethyl)-4,6,7,8-tetrahydro-5H-thieno[3,2-b]azepin-5-one.

EXAMPLE 190

2-(2-(4-(4-methylbenzo(b)furan-3-yl)piperazin-1-yl)ethyl)-4,6,7,8-tetrahydro-5H-thieno[3,2-b]azepin-5-one.

EXAMPLE 191

2-(2-(4-(5-methylbenzo(b)furan-3-yl)piperazin-1-yl)ethyl)-4,6,7,8-tetrahydro-5H-thieno[3,2-b]azepin-5-one.

EXAMPLE 192

2-(2-(4-(6-methylbenzo(b)furan-3-yl)piperazin-1-yl)ethyl)-4,6,7,8-tetrahydro-5H-thieno[3,2-b]azepin-5-one.

EXAMPLE 193

2-(2-(4-(7-methylbenzo(b)furan-3-yl)piperazin-1-yl)ethyl)-4,6,7,8-tetrahydro-5H-thieno[3,2-b]azepin-5-one.

EXAMPLE 194

2-(2-(4-(4-fluorobenzo(b)thiophen-3-yl)piperazin-1-yl)ethyl)-4,6,7,8-tetrahydro-5H-thieno[3,2-b]azepin-5-one.

EXAMPLE 195

2-(2-(4-(5-fluorobenzo(b)thiophen-3-yl)piperazin-1-yl)ethyl)-4,6,7,8-tetrahydro-5H-thieno[3,2-b]azepin-5-one.

EXAMPLE 196

2-(2-(4-(6-fluorobenzo(b)thiophen-3-yl)piperazin-1-yl)ethyl)-4,6,7,8-tetrahydro-5H-thieno[3,2-b]azepin-5-one.

EXAMPLE 197

2-(2-(4-(7-fluorobenzo(b)thiophen-3-yl)piperazin-1-yl)ethyl)-4,6,7,8-tetrahydro-5H-thieno[3,2-b]azepin-5-one.

EXAMPLE 198

2-(2-(4-(4-methylbenzo(b)thiophen-3-yl)piperazin-1-yl)ethyl)-4,6,7,8-tetrahydro-5H-thieno[3,2-b]azepin-5-one.

EXAMPLE 199

2-(2-(4-(5-methylbenzo(b)thiophen-3-yl)piperazin-1-yl)ethyl)-4,6,7,8-tetrahydro-5H-thieno[3,2-b]azepin-5-one.

EXAMPLE 200

2-(2-(4-(6-methylbenzo(b)thiophen-3-yl)piperazin-1-yl)ethyl)-4,6,7,8-tetrahydro-5H-thieno[3,2-b]azepin-5-one.

EXAMPLE 201

2-(2-(4-(7-methylbenzo(b)thiophen-3-yl)piperazin-1-yl)ethyl)-4,6,7,8-tetrahydro-5H-thieno[3,2-b]azepin-5-one.

EXAMPLE 202

6-acetyl-3-ethyl-2-(2-(4-(benzo(b)furan-3-yl)piperidin-1-yl)ethyl)-4,5,6,7-tetrahydrothieno[2,3-c]pyridine.

EXAMPLE 203

6-acetyl-3-ethyl-2-(2-(4-(4-methylbenzo(b)furan-3-yl)piperidin-1-yl)ethyl)- 4,5,6,7-tetrahydrothieno[2,3-c]pyridine.

EXAMPLE 204

6-acetyl-3-ethyl-2-(2-(4-(4-methylbenzo(b)thiophen-3-yl)piperidin-1-yl)ethyl)-4,5,6,7-tetrahydrothieno[2,3-c]pyridine.

EXAMPLE 205

6-acetyl-3-ethyl-2-(2-(4-(5-methylbenzo(b)thiophen-3-yl)piperidin-1-yl)ethyl)-4,5,6,7-tetrahydrothieno[2,3-c]pyridine.

EXAMPLE 206

6-acetyl-3-ethyl-2-(2-(4-(6-methylbenzo(b)thiophen-3-yl)piperidin-1-yl)ethyl)-4,5,6,7-tetrahydrothieno[2,3-c]pyridine.

EXAMPLE 207

6-acetyl-3-ethyl-2-(2-(4-(7-methylbenzo(b)thiophen-3-yl)piperidin-1-yl)ethyl)-4,5,6,7-tetrahydrothieno[2,3-c]pyridine.

EXAMPLE 208

6-acetyl-3-ethyl-2-(2-(4-(4-fluorobenzo(b)furan-3-yl)piperazin-1-yl)ethyl)-4,5,6,7-tetrahydrothieno[2,3-c]pyridine.

EXAMPLE 209

6-acetyl-3-ethyl-2-(2-(4-(5-fluorobenzo(b)furan-3-yl)piperazin-1-yl)ethyl)-4,5,6,7-tetrahydrothieno[2,3-c]pyridine.

EXAMPLE 210

6-acetyl-3-ethyl-2-(2-(4-(6-fluorobenzo(b)furan-3-yl)piperazin-1-yl)ethyl)-4,5,6,7-tetrahydrothieno[2,3-c]pyridine.

EXAMPLE 211

6-acetyl-3-ethyl-2-(2-(4-(7-fluorobenzo(b)furan-3-yl)piperazin-1-yl)ethyl)-4,5,6,7-tetrahydrothieno[2,3-c]pyridine.

EXAMPLE 212

6-acetyl-3-ethyl-2-(2-(4-(4-methylbenzo(b)furan-3-yl)piperazin-1-yl)ethyl)-4,5,6,7-tetrahydrothieno[2,3-c]pyridine.

EXAMPLE 213

6-acetyl-3-ethyl-2-(2-(4-(5-methylbenzo(b)furan-3-yl)piperazin-1-yl)ethyl)-4,5,6,7-tetrahydrothieno[2,3-c]pyridine.

EXAMPLE 214

6-acetyl-3-ethyl-2-(2-(4-(6-methylbenzo(b)furan-3-yl)piperazin-1-yl)ethyl)-4,5,6,7-tetrahydrothieno[2,3-c]pyridine.

EXAMPLE 215

6-acetyl-3-ethyl-2-(2-(4-(7-methylbenzo(b)furan-3-yl)piperazin-1-yl)ethyl)-4,5,6,7-tetrahydrothieno[2,3-c]pyridine.

EXAMPLE 216

6-acetyl-3-ethyl-2-(2-(4-(4-fluorobenzo(b)thiophen-3-yl)piperazin-1-yl)ethyl)-4,5,6,7-tetrahydrothieno[2,3-c]pyridine.

EXAMPLE 217

6-acetyl-3-ethyl-2-(2-(4-(5-fluorobenzo(b)thiophen-3-yl)piperazin-1-yl)ethyl)-4,5,6,7-tetrahydrothieno[2,3-c]pyridine.

EXAMPLE 218

6-acetyl-3-ethyl-2-(2-(4-(6-fluorobenzo(b)thiophen-3-yl)piperazin-1-yl)ethyl)-4,5,6,7-tetrahydrothieno[2,3-c]pyridine.

EXAMPLE 219

6-acetyl-3-ethyl-2-(2-(4-(7-fluorobenzo(b)thiophen-3-yl)piperazin-1-yl)ethyl)-4,5,6,7-tetrahydrothieno[2,3-c]pyridine.

EXAMPLE 220

6-acetyl-3-ethyl-2-(2-(4-(4-methylbenzo(b)thiophen-3-yl)piperazin-1-yl)ethyl)-4,5,6,7-tetrahydrothieno[2,3-c]pyridine.

EXAMPLE 221

6-acetyl-3-ethyl-2-(2-(4-(5-methylbenzo(b)thiophen-3-yl)piperazin-1-yl)ethyl)-4,5,6,7-tetrahydrothieno[2,3-c]pyridine.

EXAMPLE 222

6-acetyl-3-ethyl-2-(2-(4-(6-methylbenzo(b)thiophen-3-yl)piperazin-1-yl)ethyl)-4,5,6,7-tetrahydrothieno[2,3-c]pyridine.

EXAMPLE 223

6-acetyl-3-ethyl-2-(2-(4-(7-methylbenzo(b)thiophen-3-yl)piperazin-1-yl)ethyl)-4,5,6,7-tetrahydrothieno[2,3-c]pyridine.

EXAMPLE 224

2-(2-(4-(6-fluorobenzo(b)thiophen-3-yl)piperidin-1-yl)ethyl)-4,5,6,7-tetrahydro-8H-thieno[2,3-c]azepin-8-one.

EXAMPLE 225

2-(2-(4-(6-fluorobenzo(b)furan-3-yl)piperidin-1-yl)ethyl)-4,5,6,7-tetrahydro-8H-thieno[2,3-c]azepin-8-one.

EXAMPLE 226

2-(2-(4-(5-methylbenzo(b)furan-3-yl)piperidin-1-yl)ethyl)-4,5,6,7-tetrahydro-8H-thieno[2,3-c]azepin-8-one.

EXAMPLE 227

2-(2-(4-(6-methylbenzo(b)furan-3-yl)piperidin-1-yl)ethyl)-4,5,6,7-tetrahydro-8H-thieno[2,3-c]azepin-8-one.

Formulation Example 1

Tablets containing 10 mg of a compound of the formula (I) are prepared in accordance with the following formulation:

| | |
|---|---|
| Compound of formula (I) | 10.0 mg |
| Lactose | 58.5 mg |
| Corn starch | 25.0 mg |
| Crystalline cellulose | 20.0 mg |
| Polyvinylpyrrolidone K-30 | 2.0 mg |
| Talc | 4.0 mg |
| Magnesium stearate | 0.5 mg |
| | 120.0 mg |

The compound of the formula (I) is pulverized by an atomizer into fine powders below 10 µ in average particle diameter, which are admixed with lactose, corn starch and crystalline cellulose sufficiently in a kneading machine, and further kneaded with polyvinylpyrrolidone paste. The kneaded mixture is passed through a sieve of 200 mesh, dried at 50° C. and passed through a sieve of 24 mesh. Talc and magnesium stearate are mixed therewith and the mixture is compressed into 120.0 mg tablets with a punch of 8 mm in diameter. These tablets are, if desired, subjected to sugar-coating or film-coating.

While the present invention has been adequately and sufficiently described in the foregoing specification including examples, the description can be changed or modified within the spirit and scope of this invention.

What is claimed is:

1. A condensed thiophene compound represented by the following formula (I) or a pharmaceutically acceptable salt thereof:

$$\begin{array}{c} R^2 \diagdown \phantom{N} \diagup A-(CH_2)m \\ N \\ | \\ B \\ \diagdown (CH_2)n - D \end{array} \begin{array}{c} \phantom{x} \diagdown \phantom{R^1} \\ S \\ \diagup \phantom{x} \diagdown G-Q-T \end{array} \quad (I)$$

wherein the ring S is selected from the group consisting of the following fused thiophenes:

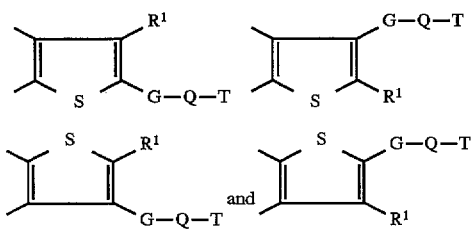

wherein R¹ represents a hydrogen atom, a halogen atom, an alkyl group, an acyl group or a hydroxyalkyl group;

R² represents a hydrogen atom, an alkyl group, an acyl group, a carbamoyl group, a substituted carbamoyl group, an aryl group or an arylalkyl group;

G represents a —CH₂— group, a —CH(OR³)— group, a —CO— group or a —S(O)$_t$— group; wherein R³ represents a hydrogen atom, an alkyl group or an acyl group and t is 0, 1, or 2;

Q represents a straight alkylene group or a branched chain alkylene group;

T represents a tertiary amino group;

D represents a —CH₂ group or a —S(O)$_u$— group; wherein u is 0, 1 or 2;

either (i) A is absent and B represents a carbonyl group or a thiocarbonyl group, or (ii) both A and B are absent;

when A is absent and B is a carbonyl group or a thiocarbonyl group, m is 0 and n is 0, 1 or 2; when both A and B are absent, m is 0 and n is 0 or an integer of 1 to 4.

2. The compound of claim 1 selected from the group consisting of:

2-(2-(4-(6-fluoro-1,2-benzisoxazol-3-yl)piperidin-1-yl)ethyl)-4,6,7,8-tetrahydro-5H-thieno[3,2-b]azepin-5-one, 3-(2-(4-(6-fluoro-1,2-benzisoxazol-3-yl)piperidin-1-yl)ethyl)-2-methyl-4,6,7,8-tetrahydro-5H-thieno[3,2-b]azepin-5-one, or a pharmaceutically acceptable salt thereof.

3. The compound of claim 1 selected from the group consisting of:

2-(2-(4-(6-fluorobenzo(b)furan-3-yl)piperidin-1-yl)ethyl)-4,6,7,8-tetrahydro-5H-thieno[3,2-b]azepin-5-one, 2-(2-(4-(5-methylbenzo(b)furan-3-yl)piperidin-1-yl)ethyl)-4,6,7,8-tetrahydro-5H-thieno[3,2-b]azepin-5-one, 2-(2-(4-(6-fluorobenzo(b)furan-3-yl)piperazin-1-yl)ethyl)-4,6,7,8-tetrahydro-5H-thieno[3,2-b]azepin-5-one, 2-(2-(4-(4-methylbenzo(b)furan-3-yl)piperazin-1-yl)ethyl)-4,6,7,8-tetrahydro-5H-thieno[3,2-b]azepin-5-one, 2-(2-(4-(6-methylbenzo(b)furan-3-yl)piperazin-1-yl)ethyl)-4,6,7,8-tetrahydro-5H-thieno[3,2-b]azepin-5-one, 2-(2-(4-(6-methylbenzo(b)thiophen-3-yl)piperazin-1-yl)ethyl)-4,6,7,8-tetrahydro-5H-thieno[3,2-b]azepin-5-one, 2-(2-(4-(6-fluorobenzo(b)thiophen-3-yl)piperidin-1-yl)ethyl)-4,6,7,8-tetrahydro-5H-thieno[3,2-b]azepin-5-one, 2-(2-(4-(6-fluorobenzo(b)thiophen-3-yl)piperidin-1-yl)ethyl)-4,5,6,7-tetrahydro-8H-thieno[2,3-c]azepin-8-one, 2-(2-(4-(6-fluorobenzo(b)furan-3-yl)piperidin-1-yl)ethyl)-4,5,6,7-tetrahydro-8H-thieon[2,3 -c]azepin-8 -one, 2-(2-(4-(5-methylbenzo(b)furan-3-yl)piperidin-1-yl)ethyl)-4,5,6,7-tetrahydro-8H-thieno[2,3-c]azepin-8-one, 2-(2-(4-(6-methylbenzo(b)furan-3-yl)piperidin-1-yl)ethyl)-4,5,6,7-tetrahydro-8H-thieno[2,3-c]azepin-8-one or a pharmaceutically acceptable salt thereof.

4. A condensed thiophene compound of the formula:

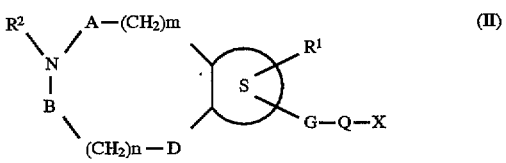

(II)

wherein X is hydroxyl, halogen, methanesulfonyloxy or p-toluenesulfonyloxy, and other symbols are as defined in claim 1.

5. A pharmaceutical composition comprising a compound of claim 1 and pharmaceutical additives.

6. An antipsychotic drug containing a compound of claim 1 as an effective ingredient.

7. The compound of claim 1 or a pharmaceutically acceptable salt thereof, wherein T is a tertiary amino of -N(Rb)(Rc), wherein Rb and Rc are the same or different and each is an alkyl group, or Rb and Rc together with the adjacent nitrogen atom form a cyclic amino group represented by the following formulae:

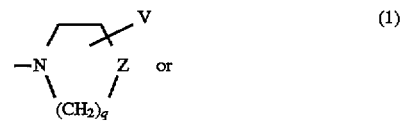 (1)

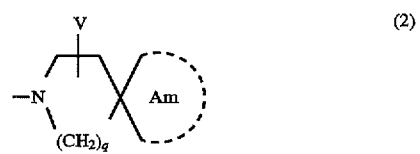 (2)

wherein q is an integer of 1 to 4; Z is methylene or N-R⁵, wherein R⁵ is selected from the group consisting of an aryl group, a diarylalkyl group, a heteroaryl group and a heteroarylalkyl group; V is selected from the group consisting of a hydrogen atom, a hydroxyl group, a heteroaryl group, a heteroarylalkyl group and a bisarylmethylene group and the number of V is 1 to 4; the cyclic amino group of formula (1) may contain a carbonyl group in the cycle and may be condensed with an aryl group or a heteroaryl group; and Am of formula (2) may contain an amido bond in the cycle and may contain an oxygen atom, a sulfur atom, a carbonyl group and/or N-R⁶ in the ring, wherein R⁶ is a hydrogen atom, an alkyl group or a phenyl group.

* * * * *